US009309496B2

(12) United States Patent
Ma

(10) Patent No.: US 9,309,496 B2
(45) Date of Patent: Apr. 12, 2016

(54) METHOD FOR EXPANSION OF STEM CELLS AND THE USE OF SUCH CELLS

(75) Inventor: Yupo Ma, Setauket, NY (US)

(73) Assignee: The Research Foundation for The State University of New York, Albany, NY (US)

(*) Notice: Subject to any disclaimer, the term of this patent is extended or adjusted under 35 U.S.C. 154(b) by 72 days.

(21) Appl. No.: 13/817,726

(22) PCT Filed: Aug. 23, 2011

(86) PCT No.: PCT/US2011/048819
§ 371 (c)(1),
(2), (4) Date: May 15, 2013

(87) PCT Pub. No.: WO2012/027376
PCT Pub. Date: Mar. 1, 2012

(65) Prior Publication Data
US 2013/0315879 A1 Nov. 28, 2013

Related U.S. Application Data

(60) Provisional application No. 61/376,122, filed on Aug. 23, 2010.

(51) Int. Cl.
*C12N 5/0789* (2010.01)
*C07K 14/475* (2006.01)
*A61K 35/28* (2015.01)
*C12N 5/0775* (2010.01)
*C07K 14/47* (2006.01)

(52) U.S. Cl.
CPC ............. *C12N 5/0663* (2013.01); *A61K 35/28* (2013.01); *C07K 14/47* (2013.01); *C12N 5/0647* (2013.01); *C12N 2501/40* (2013.01)

(58) Field of Classification Search
CPC .... A61K 35/28; C12N 5/0647; C07K 14/475; C07K 14/4705
See application file for complete search history.

(56) References Cited

U.S. PATENT DOCUMENTS

2009/0227032 A1   9/2009   Yamanaka et al.

FOREIGN PATENT DOCUMENTS

WO   WO 2008/151035 A2   12/2008
WO   WO 2010/042800 A1   4/2010

OTHER PUBLICATIONS

Tsubooka et al., Genes to Cells, 2009 14(6):683-694.*
Sakaki-Yumoto et al., (Development. Aug. 2006;133(15):3005-3013).*
Lim et al., (Cell Stem Cell 3: 543-554, (2008)).*
Yang et al., (PLOS One May 21, 2010 5(5):e10766. DOI:10.1371/journal.pone.*
Eminli et al., (Nat Genet. Sep. 2009 ; 41(9): 968-976).*
Zhang et al. (2006). SalI4 modulates embryonic stem cell pluripotency and early embryonic development by the transcriptional regulation of Pou5f1. *Nature Cell Biology*, 8(10), 1114-1123.
Yang et al. (2008). Genome-wide analysis reveals SalI4 to be a major regulator of pluripotency in murine-embryonic stem cells. *Proc Natl Aced Sci USA*, 105(50), 19756-19761.
Yang et al. (2008). SALL4 is a key regulator of survival and apoptosis in human leukemic cells. *Blood*, 112(3), 805-813.
Aguila et al. (2011). SALL4 is a robust stimulator for the expansion of hematopoietic stem cells. *Blood*, 118(3), 576-585.
Notification of Transmittal of the International Search Report and the Written Opinion of the International Searching Authority, or the Declaration, including an International Search Report and Written Opinion of the International Searching Authority, mailed May 1, 2012 in connection with PCT International Application No. PCT/US2011/048819, filed Aug. 23, 2011.
Lu J. et al., "Stem Cell Factor SALL4 Represses the Transcriptions of PTEN and SALL1 Through an Epigenetic Repressor Complex", PLoS One 4(5):1-13 (May 2009).
Retrieved from EBI Accession No. UNIPROT: Q9UJQ4 (10 pages) (May 1, 2000).
Supplementary European Search Report dated Jan. 28, 2014 received from related Application No. 11820528.5.

* cited by examiner

*Primary Examiner* — Daniel C Gamett
(74) *Attorney, Agent, or Firm* — Scully, Scott, Murphy & Presser, P.C.

(57) ABSTRACT

The present invention demonstrates that SALL4A and SALL4B are strong positive regulators of hematopoetic stem cell expansion. HSCs receiving expression of SALL4A or SALL4B are able to achieve a high-level of expansion. Cultures of SALL4-transduced cells results in extensive HSC expansion with over 1000-fold higher levels than controls within 2 to 3 weeks and expanded HSCs show no or very little maturation. Moreover, the expansion occurs quite rapidly with significant HSC growth in just a few days. In addition, SALL4-induced HSC expansion exhibits no impairment of hematopoietic cell differentiation. SALL4 appears to function in the maintenance of an undifferentiated proliferation state and block cell differentiation for HSCs.

15 Claims, 48 Drawing Sheets

```
   1 MSFRQAHPG HINSEEDGGR QSPGQQTPEF ADAAPAAPAA GELGAPVNHP
  51 GNDEVASEDE ATVKRLRPEE FFSISEFLEH KDCTMPPV
 101 LIMNSEGPV PSEDFSGAVL SHQPTSFGGK DCHRENGGSS EDHEEKPDAE
 151 SVVYLKTETA LPPTPQDISY LAKGKVANTN VTLQALRGTK VAVHGPSADA
 201 LPAPVPGAND IPWLEQLLC LQQQLQQIQ LTEQIRIQVN MWASHALHSS
 251 GAGADTLKTL GSHMSQQVSA AVALLSQKAG SQGLSLDALK QAPLPHANIP
 301 SATSSLSPGL APFTLKPDGT RVLPNVMSRL PSALLPQAPG SVLFQSPFST
 351 VALDTSKKGK GKPPNISAVD VKPKDEAALY KHKCKYCSKV FGTDSSLQIH
 401 LRSHTGERPF VCSVCGHRFT TKGNLKVHFH RHPQVRANPQ LFAEFQDKVA
 451 AGNGIPYALS VDDPIDEPSL SIDSKFVLVT TSVGLPQHLS SGTHPKDLTG
 501 GELPGDLQPG PEPESGCGPT LPCVGPNTHS PRAGGPGCSG TPEPGSETLK
 551 LQQLVENIDK ATTDPNECLI CHRVLSCQSS LKHHYRTHTG ERPFVCKICG
 601 RAFSTKGNLE THLGVHRTNT SIKTQERCPI CQKTFTNAVM LQQHIRMHMG
 651 CQIRNTPLPE NPCDFPCSEP MTVGRGSTG AICHDDYIES IDVFEVSSQL
 701 APSSSKVPT PLPSIHSASP TLGFAMHHSL DRPGKVGRAP FNLQPGGRE
 751 MGSVESDGLT NDSSSLRGDG ETQRPSPDIL ETTSFQLLSP AMSQAESTES
 801 KSPLAGGRLE GSFNGHYTMF GRSSLPSTFI NFS SASALQIHER VPGTFVGPST
 851 LSPGMTPLLA AQFRRQAKQH GCTNGGRNFS SASALQIHER THGEKPFVC
 901 HICGRAFTTK GSLKVHYHTH CAMNNSAERG PKLAIENTMA LLGTDGKRVS
 951 EITPKEILAP SVNTDPVVHN QFTSMLNGGL AVTNEISVI QSGVYTLPV
1001 SLCATSVVNN ATVSKMDGSQ SGISADVEKP SATDGVPKHQ FPHFLEENKI
1051 KVS
```

Peptides of His-TAT-SALL4B identified by LC-MS/MS are in black text

SEQUENCE LISTING

```
<160> NUMBER OF SEQ ID NOS: 12

<210> SEQ ID NO 1
<211> LENGTH: 5143
<212> TYPE: DNA
<213> ORGANISM: Homo sapiens

<400> SEQUENCE: 1
ttattctgcc ccagctgatg tttgagccag catgtcgcgg aggaagcaag cgaagcctca        60
acatttccaa tccgaccccg aagtggcctc gctccccgg cgagatggag acacagaaaa       120
gggtcaaccg agtcgcccta ctaagagcaa ggatgccac gtctgtggcc ggtgctgtgc       180
cgagttcttt gaattatcag atcttctgct ccacaagaag aactgtacta aaaatcaatt       240
agttttaatc gtaaatgaaa atccagcctc cccaccgaa accttctccc ccagccccc       300 tcctgataat cctgatgaac aaatgaatga cacagttaac aaaacagatc aagtggactg       360
```

```
cagcgacctt tcagaacaca acggacttga cagggaagag tccatggagg tggaggcccc    420
ggttgctaac aaaagcggca gcggcacttc agcggcagc cacagcagta ccgcccaag     480 cagcagcagc agcagcagca gcagcagcgg cggcggcggc agctcctcca caggtacctc    540
agcgatcaca acctctctac ctcaactcgg ggacctgaca cactgggca acttctccgt     600 aatcaacagc aacgtcatca tcgagaacct ccagagcacc aaggtggcgg tggcccagtt    660
ctcccaggaa gcgaggtgcg gcggggcctc tgggggcaag ctggccgtcc cagccctcat    720
ggaacaactc ctagctctgc agcagcagca gatccaccag ctgcaattga tcgaacagat    780
tcgtcaccaa atattgctgt tggcttctca gaatgcagac ttgccaacat cttctagtcc    840
ttctcaaggt actttacgaa catctgccaa ccccttgtcc acgctaagtt cccatttatc    900
tcagcagctg gcagcagcag ctggattggc acagagcctc gccagccaat ctgccagcat    960
tagtggtgtg aaacagctac ccccaatcca gctacctcag agcagttctg caacaccat    1020 cattccatcc aacagcggct cttctcccaa tatgaacata ttggcagcgg cagttaccac    1080
cccgtcctct gaaaaagtgg cttcaagtgc tggggcctcc catgtcagca cccagcggt    1140 ctcatcatcg tcctcaccag cttttgcaat aagcagttta ttaagtcctg cgtctaatcc    1200
acttctacct cagcaagcct ccgctaactc ggttttcccc agccctttgc ccaacatcgg    1260
aacaactgca gaggatttaa actccttgtc tgccttggcc cagcaaagaa aaagcaagcc    1320
accaaatgtc actgcctttg aagcgaaaag tacttccgat gaggcattct tcaaacacaa    1380
gtgcaggttc tgcgcgaagg tctttgggag tgacagtgcc ttgcagatcc acttgcgttc    1440
ccataccgga gagaggccat tcaagtgcaa catctgcggg aacaggttct ccaccaaggg    1500
gaatctgaaa gtccactttc agcgccacac agagaaatac cctcatatcc agatgaaccc    1560
ctatcctgtg cctgagcatt tggacaatat ccccacgagt actggcatcc catatggcat    1620
gtccatccct ccagagaagc cagtcaccag ctggctagac accaaaccag tcctgcctac    1680
tctgaccact tcagtcggcc tgccgttgcc cccaacccct ccaagcctca taccttcat    1740 caagacggaa gagccagccc ccatccccat cagccattct gccaccagcc cccaggctc    1800 agtcaaaagt gactccgggg gccctgagtc agccacaaga aacctaggtg ggctcccaga    1860
ggaagccgaa gggtccactc tgccacccctc tggtggcaaa agcgaagaga gtggcatggt    1920
caccaactca gtcccgacgg cgagcagtag cgtcctgagc tccccagcgg cagactgcgg    1980
ccccgcgggc agtgccacca ccttcaccaa ccctttgttg ccgctcatgt ccgagcagtt    2040
caaggccaag tttccttttg ggggactcct ggactcagct caggcatcag agacgtccaa    2100
gcttcagcaa ctggtagaaa acattgacaa gaaggccact gaccccaatg agtgcatcat    2160
ctgccaccgg gttctcagct gccagagcgc cttgaaaatg cactacagga cacacactgg    2220
ggagaggccc tttaagtgta gatctgtgg ccgggctttc accacgaaag ggaatcttaa    2280
aacccactac agtgtccatc gtgctatgcc ccgctcaga gtccagcatt cctgccccat    2340
ctgccagaag aagttcacga acgctgtggt cctgcagcag cacatccgaa tgcatatggg    2400
aggccagatc cccaacaccc cagtccccga cagctactct gagtccatgg agtctgacac    2460
aggttccttt gatgagaaaa attttgatga cctagacaac ttctctgatg aaaacatgga    2520
agactgtcct gagggcagca tccctgatac acctaagtct gcagacgcct cccaagacag    2580
cttatcctct tcgcctttgc ccctcgagat gtcgagcatc gctgctttgg aaaatcagat    2640
gaagatgatc aatgctggcc tggcagagca gctacaggcc agcctgaagt cagtggagaa    2700
```

```
tgggtccatc gagggggatg tcctgaccaa tgattcatcc tcagtgggtg gtgacatgga    2760
aagccaaagt gctggcagcc cagccatctc agagtctacc tcttccatgc aggctctgtc    2820
cccgtccaac agcacgcagg agttccacaa gtcacccagc attgaggaga aaccacagag    2880
agcggtccca agcgagtttg ccaatggttt gtctcccacc ccagtgaatg gtggggcttt    2940
ggatttgaca tctagtcacg cagagaaaat catcaaagaa gattctttgg ggatcctctt    3000
cccttttaga gaccggggta aatttaaaaa cactgcttgt gacatttgtg gcaaaacatt    3060
tgcttgtcag agtgccttgg acattcacta tagaagtcat accaaagaga gaccatttat    3120
ttgcacagtt tgcaatcgtg gcttttccac aaagggtaat ttgaagcagc acatgttgac    3180
acatcagatg cgagatctgc catcccagct ctttgagccc agttccaacc ttggccccaa    3240
tcagaactca gcggtgattc ccgccaactc gttgtcatct ctcatcaaga cagaggtcaa    3300
cggcttcgtg catgtttctc ctcaggacag taaggacacc cccaccagtc acgtcccgtc    3360
tgggcctctg tcttcctctg ccacatcccc agttctgctc cctgctctgc ccaggagaac    3420
tcccaagcag cactactgca acacatgtgg caaaaccttc tcctcatcga gtgccctgca    3480
gattcacgag agaactcaca ctggagagaa acccttgct tgcactattt gtggaagagc    3540
tttcacgact aaaggcaatc ttaaggtaca catgggcact cacatgtgga atagcacccc    3600
tgcacgacgg ggtcggcggc tctctgtgga tggccccatg acatttctag gaggcaatcc    3660
cgtcaagttc ccagaaatgt tccagaagga tttggcggca agatcaggaa gtggggatcc    3720
ttccagcttc tggaatcagt atgcagcagc gctctccaac gggctggcga tgaaggccaa    3780
cgagatctcc gtcattcaga acggtggcat ccctccaatt cctggaagcc tcggcagtgg    3840
gaacagctca cctgttagtg ggctgacggg aaacctggag aggctccaga actcagagcc    3900
caatgctccc ctggccggcc tggagaaaat ggcaagcagt gagaacggaa ccaacttccg    3960
cttcacccgc ttcgtggagg acagcaagga gatcgtcacg agttaaagca gctcgggctg    4020
gagacatagc attcattcct gttcagaatg cgacctatgg tggcctccta ctccttgccc    4080
cccaccccgc ccgccccctt ccttctgttc cccagatcta tgaactacaa cattatgaag    4140
acattctttt gtaccttgtt caactttaga gttctaagaa agcttattta ttagcgatat    4200
aaccttgctt tgcaaacaga atgcaagcgt taactttggt cttctgtatt ttggactaaa    4260
tactaattga ctagagtgct gtaaacttgc tgtaacattt atggcaattg caagttgccc    4320
tgctaggcag ttgtaatctg gcattaactt attttctata tccagtttaa tatgaatctg    4380
gtgttgatgc aatgcctcag tgatgcatta gatctctaat aaagtctgta tatacatgta    4440
cactttgatc ctgctggaaa attttatcag caaacacatt gtctaatctt tcaaaacaga    4500
tttaaggaaa ggactgaaag tacagactga acagtgtggt tctttgaaag gtttggtttt    4560
ttaattttta ttctaaaatt caaccttttt ttttgtcgat ttaaccattt ccattttgaa    4620
ctgctatttg tattgtgctt tttacttgag tcgtcttcaa tgttaataag tttctgtaca    4680
gtaataagca cgcagaattc tttagagaaa aagaaaacaa gcgttgtttt ggtagttgaa    4740
actgagacgt aacattttgc cttgtaggta tattcacgat agaaaatgtg tgctggaatt    4800
tcacaatgct gctaagtata gcatcttgaa caaccttcag tggagaaaat gtagatgctc    4860
ttgtatatac aataagaaat atcactttca ttcaaatgta catatgttcc ttacaagagc    4920
aaatgcttct tcttgatcaa gagagcaggt atagtgtttg tttatttgt cttaggtatg    4980 gaagaaaaaa attggactgt tacatgcact ttccttggaaa gttgaaagga aagggggggt    5040
ccaatttctt taacatttaa tacttactaa caacagagat actgtaattt tactcaagta    5100
```

| atcaaataca ttttttttgc aacagataaa acaaaatact gtg | 5143 |

<210> SEQ ID NO 2
<211> LENGTH: 5253
<212> TYPE: DNA
<213> ORGANISM: Homo sapiens

<400> SEQUENCE: 2

| ctttggaggt tcagagctgc aagaagatgg ggactggtgt cggggcgcca gcgcctgacc | 60 |
| cgctggggtt gcggccgggg tggagagtgc tgctggccgc cagttgttcc ggagacggtg | 120 |
| caaacggacg gggaaagtgt cggggtctgg ctcgcaaaat ttatctccgc atctcttccc | 180 |
| acaacacttg caccctctgc cccccaaaat ctttctggag acacagaaaa gggtcaaccg | 240 |
| agtcgcccta ctaagagcaa ggatgccacg tctgtggcc ggtgctgtgc cgagttcttt | 300 |
| gaattatcag atcttctgct ccacaagaag aactgtacta aaaatcaatt agttttaatc | 360 |
| gtaaatgaaa atccagcctc cccacccgaa accttctccc ccagcccccc tcctgataat | 420 |
| cctgatgaac aaatgaatga cacagttaac aaaacagatc aagtggactg cagcgacctt | 480 |
| tcagaacaca acggacttga cagggaagag tccatggagg tggaggcccc ggttgctaac | 540 |
| aaaagcggca gcggcacttc cagcggcagc cacagcagta ccgccccaag cagcagcagc | 600 |
| agcagcagca gcagcagcgg cggcggcggc agctcctcca caggtacctc agcgatcaca | 660 |
| acctctctac ctcaactcgg ggacctgaca acactgggca acttctccgt aatcaacagc | 720 |
| aacgtcatca tcgagaacct ccagagcacc aaggtggcgg tggcccagtt ctcccaggaa | 780 |
| gcgaggtgcg gcggggcctc tgggggcaag ctggccgtcc cagccctcat ggaacaactc | 840 |
| ctagctctgc agcagcagca gatccaccag ctgcaattga tcgaacagat tcgtcaccaa | 900 |
| atattgctgt tggcttctca gaatgcagac ttgccaacat cttctagtcc ttctcaaggt | 960 |
| actttacgaa catctgccaa ccccttgtcc acgctaagtt cccatttatc tcagcagctg | 1020 |
| gcagcagcag ctggattggc acagagcctc gccagccaat ctgccagcat tagtggtgtg | 1080 |
| aaacagctac ccccaatcca gctacctcag agcagttctg gcaacaccat cattccatcc | 1140 |
| aacagcggct cttctcccaa tatgaacata ttggcagcgg cagttaccac cccgtcctct | 1200 |
| gaaaaagtgg cttcaagtgc tggggcctcc catgtcagca acccagcggt ctcatcatcg | 1260 |
| tcctcaccag cttttgcaat aagcagttta ttaagtcctg cgtctaatcc acttctacct | 1320 |
| cagcaagcct ccgctaactc ggttttcccc agccctttgc ccaacatcgg aacaactgca | 1380 |
| gaggatttaa actccttgtc tgccttggcc cagcaaagaa aaagcaagcc accaaatgtc | 1440 |
| actgcctttg aagcgaaaag tacttccgat gaggcattct tcaaacacaa gtgcaggttc | 1500 |
| tgcgcgaagg tctttgggag tgacagtgcc ttgcagatcc acttgcgttc ccataccgga | 1560 |
| gagaggccat tcaagtgcaa catctgcggg aacaggttct ccaccaaggg gaatctgaaa | 1620 |
| gtccactttc agcgccacaa agagaaatac cctcatatcc agatgaaccc ctatcctgtg | 1680 |
| cctgagcatt tggacaatat ccccacgagt actggcatcc catatggcat gtccatccct | 1740 |
| ccagagaagc cagtcaccag ctggctagac accaaaccag tcctgcctac tctgaccact | 1800 |
| tcagtcggcc tgccgttgcc cccaacccc ccaagcctca tacccttcat caagacggaa | 1860 |
| gagccagccc ccatccccat cagccattct gccaccagcc cccaggctc agtcaaaagt | 1920 |
| gactccgggg gccctgagtc agccacaaga aacctaggtg ggctcccaga ggaagccgaa | 1980 |
| gggtccactc tgccaccctc tggtggcaaa agcgaagaga gtggcatggt caccaactca | 2040 |

```
gtcccgacgg cgagcagtag cgtcctgagc tccccagcgg cagactgcgg ccccgcgggc    2100
agtgccacca ccttcaccaa ccctttgttg ccgctcatgt ccgagcagtt caaggccaag    2160
tttccttttg ggggactcct ggactcagct caggcatcag agacgtccaa gcttcagcaa    2220
ctggtagaaa acattgacaa gaaggccact gaccccaatg agtgcatcat ctgccaccgg    2280
gttctcagct gccagagcgc cttgaaaatg cactacagga cacacactgg ggagaggccc    2340
tttaagtgta agatctgtgg ccgggctttc accacgaaag ggaatcttaa aacccactac    2400
agtgtccatc gtgctatgcc cccgctcaga gtccagcatt cctgccccat ctgccagaag    2460
aagttcacga acgctgtggt cctgcagcag cacatccgaa tgcatatggg aggccagatc    2520
cccaacaccc cagtccccga cagctactct gagtccatgg agtctgacac aggttccttt    2580
gatgagaaaa attttgatga cctagacaac ttctctgatg aaaacatgga agactgtcct    2640
gagggcagca tccctgatac acctaagtct gcagacgcct cccaagacag cttatcctct    2700
tcgcctttgc ccctcgagat gtcgagcatc gctgctttgg aaaatcagat gaagatgatc    2760
aatgctggcc tggcagagca gctacaggcc agcctgaagt cagtggagaa tgggtccatc    2820 gaggggggatg tcctgaccaa tgattcatcc tcagtgggtg gtgacatgga aagccaaagt    2880
gctggcagcc cagccatctc agagtctacc tcttccatgc aggctctgtc cccgtccaac    2940
agcacgcagg agttccacaa gtcacccagc attgaggaga aaccacagag agcggtccca    3000
agcgagtttg ccaatggttt gtctcccacc ccagtgaatg tggggctttt ggatttgaca    3060
tctagtcacg cagagaaaat catcaaagaa gattctttgg ggatcctctt cccttttaga    3120
gaccggggta aatttaaaaa cactgcttgt gacatttgtg gcaaaacatt tgcttgtcag    3180
agtgccttgg acattcacta tagaagtcat accaaagaga gaccatttat ttgcacagtt    3240
tgcaatcgtg gcttttccac aaagggtaat ttgaagcagc acatgttgac acatcagatg    3300
cgagatctgc catcccagct cttttgagccc agttccaacc ttggccccaa tcagaactca    3360
gcggtgattc ccgccaactc gttgtcatct ctcatcaaga cagaggtcaa cggcttcgtg    3420
catgtttctc ctcaggacag taaggacacc cccaccagtc acgtcccgtc tgggcctctg    3480
tcttcctctg ccacatcccc agttctgctc cctgctctgc caggagaaac tcccaagcag    3540
cactactgca acacatgtgg caaaaccttc tcctcatcga gtgccctgca gattcacgag    3600
agaactcaca ctggagagaa acccttttgct tgcactattt gtggaagagc tttcacgact    3660
aaaggcaatc ttaaggtaca catgggcact cacatgtgga atagcacccc tgcacgacgg    3720
ggtcggcggc tctctgtgga tggccccatg acatttctag gaggcaatcc cgtcaagttc    3780
ccagaaatgt tccagaagga tttggcggca agatcaggaa gtggggatcc ttccagcttc    3840
tggaatcagt atgcagcagc gctctccaac gggctggcga tgaaggccaa cgagatctcc    3900
gtcattcaga acggtggcat ccctccaatt cctggaagcc tcggcagtgg gaacagctca    3960
cctgttagtg ggctgacggg aaacctggag aggctccaga actcagagcc caatgctccc    4020
ctggccggcc tggagaaaat ggcaagcagt gagaacggaa ccaacttccg cttcacccgc    4080
ttcgtggagg acagcaagga gatcgtcacg agttaaagca gctcgggctg gagacatagc    4140
attcattcct gttcagaatg cgacctatgg tggcctccta ctccttgccc ccacccccgc    4200 cccgccccttt ccttctgttc cccagatcta tgaactacaa cattatgaag acattcttttt    4260 gtaccttgtt caacttttaga gttctaagaa agcttattta ttagcgatat aaccttgctt    4320
tgcaaacaga atgcaagcgt taactttggt cttctgtatt ttggactaaa tactaattga    4380
ctagagtgct gtaaacttgc tgtaacattt atggcaattg caagttgccc tgctaggcag    4440
```

```
ttgtaatctg gcattaactt attttctata tccagtttaa tatgaatctg gtgttgatgc    4500
aatgcctcag tgatgcatta gatctctaat aaagtctgta tatacatgta cactttgatc    4560
ctgctggaaa attttatcag caaacacatt gtctaatctt tcaaaacaga tttaaggaaa    4620
ggactgaaag tacagactga acagtgtggt tctttgaaag gtttggtttt ttaattttta    4680
ttctaaaatt caaccttttt ttttgtcgat ttaaccattt ccattttgaa ctgctatttg    4740
tattgtgctt tttacttgag tcgtcttcaa tgttaataag tttctgtaca gtaataagca    4800
cgcagaattc tttagagaaa aagaaaacaa gcgttgtttt ggtagttgaa actgagacgt    4860
aacattttgc cttgtaggta tattcacgat agaaaatgtg tgctggaatt cacaatgct     4920 gctaagtata gcatcttgaa caaccttcag tggagaaaat gtagatgctc ttgtatatac    4980
aataagaaat atcactttca ttcaaatgta catatgttcc ttacaagagc aaatgcttct    5040
tcttgatcaa gagagcaggt atagtgtttg tttattttgt cttaggtatg gaagaaaaaa    5100
attggactgt tacatgcact ttcttggaaa gttgaaagga aagggggggt ccaatttctt    5160
taacatttaa tacttactaa caacagagat actgtaattt tactcaagta atcaaataca    5220
ttttttttgc aacagataaa acaaaatact gtg                                  5253

<210> SEQ ID NO 3
<211> LENGTH: 4931
<212> TYPE: DNA
<213> ORGANISM: Homo sapiens

<400> SEQUENCE: 3
gagctgcaga agcgtaggga agaagctgaa gaaaaaaagg gggcgtctcc cctttaaaga      60
cttgcaaaga ttgagagaga aagagagaga gtcaagaaca gagaatcaga gagagagaga    120
gagtctgtgt ctctgggaaa gaagaacatc tctgcttcac agtgatttgc gctgggggag    180
aggcatcaat tggcttcgga cccaaggggg agacgagacc aggtcacccc ggttaagacc    240
aagtgagcgt tgcccctccc tctcccaact ctctacccgg gaatgtctcg gcgaaagcag    300
cggaaacccc aacagttaat ctcggactgc gaaggtccca gcgcgtctga gaacggtgat    360
gctagcgagg aggatcaccc ccaagtctgt gccaagtgct gcgcacaatt cactgaccca    420
actgaattcc tcgcccacca gaacgcatgt tctactgacc ctcctgtaat ggtgataatt    480
gggggccagg agaaccccaa caactcttcg gcctcctctg aacccggcc tgagggtcac     540 aataatcctc aggtcatgga cacagagcat agcaaccccc cagattctgg gtcctccgtg    600
cccacggatc ccacctgggg cccagagagg agaggagagg agtctccagg gcatttcctg    660
gtcgctgcca caggtacagc ggctggggga ggcgggggcc tgatcttggc cagtcccaag    720
ctgggagcaa cccccattacc tccagaatcg acccctgcac cccctcctcc tccaccaccc    780
cctccgcccc caggggtagg cagtggccac ttgaatatcc ccctgatctt ggaagagcta    840
cgggtgctgc agcagcggca gatccatcag atgcagatga ctgagcaaat ctgcaggcag    900
gtgctgttgc ttggctcctt aggccagacg gtgggtgccc ctgccagtcc ctcagagcta    960
cctgggacag ggactgcctc ttccaccaag cccctactac ccctcttcag ccccatcaag    1020
cctgtccaaa ccagcaagac actggcatct tcctcctcct cctcctcttc ctcttcaggg    1080
gcagaaacgc ccaagcaggc cttcttccac ctttaccacc cactggggtc acagcatcct    1140
ttctctgctg gaggggttgg gcgaagccac aaacccaccc ctgcccttc ccagccttg      1200 ccaggcagca cagatcagct gattgcctcg cctcatctgg cattcccaag caccacggga    1260
```

```
ctactggcag cacagtgtct tggggcagcc cgaggccttg aggccactgc ctccccaggg    1320
ctcctgaagc caaagaatgg aagtggtgag ctgagctacg agaagtgat gggtcccttg     1380
gagaagcctg gtggaaggca caaatgccgc ttctgtgcca aagtatttgg cagtgacagt    1440
gccctgcaga tccaccttcg ttcccacacg ggtgagaggc cctataagtg caatgtctgt    1500
ggaaaccgtt ttaccacccg tggcaacctc aaagtgcatt ccaccggca tcgtgagaag    1560
tacccacatg tgcagatgaa cccacaccca gtaccagagc acctagacta tgtcattacc    1620
agcagtggct tgccttatgg tatgtccgtg ccaccagaga aggccgagga ggaggcagcc    1680
actccaggtg gaggggttga gcgcaagcct ctggtggcct ccacaacagc actcagtgcc    1740
acagagagcc tgactctgct ctccaccagt gcaggcacag ccacggctcc aggactccct    1800
gctttcaata agtttgtgct catgaaagca gtggaaccca gaataaagc tgatgaaaac    1860
acccccccag ggagtgaggg ctcagccatc agtggagtgg cagaaagtag cacggcaact    1920
cgcatgcaac taagtaagtt ggtgacttca ctaccaagct gggcactgct taccaaccac    1980
ttcaagtcca ctggcagctt ccccttcccc tatgtgctag agcccttggg ggcctcaccc    2040
tctgagacat caaagctgca gcaactggta gaaaagattg accggcaagg agctgtggcg    2100
gtgacctcag ctgcctcagg agcccccacc acctctgccc ctgcaccttc atcctcagcc    2160
tcttctggac ctaaccagtg tgtcatctgt ctccgagtgc ttagctgtcc tcgggcccta    2220
cgccttcatt atggccaaca tggaggtgag aggcccttca aatgcaaagt gtgtggcaga    2280
gccttctcca ccaggggtaa tctgcgtgca catttcgtgg ccacaaggc cagtccagct    2340
gcccgggcac agaattcctg ccccatctgc cagaagaagt tcaccaatgc tgtcactctg    2400
cagcagcatg tccggatgca cctgggggc cagatcccca cggtggtac tgcactccct    2460
gaaggtggag gagctgctca ggagaatggc tccgagcaat ctacagtctc cggggcaggg    2520
agtttccccc agcagcagtc ccagcagcca tcaccggaag aggagttgtc tgaggaggag    2580
gaagaggagg atgaggaaga agaggaagat gtgactgatg aagattccct ggcagggaga    2640
ggctcagaga gtggaggtga gaaggcaata tcagtgagag gtgattcaga agaggcatct    2700
ggggcagagg aggaggtggg gacagtggcg gcagcagcca cagctgggaa ggagatggac    2760
agtaatgaga aaactactca acagtcttct ttgccaccac caccaccacc tgacagcctg    2820
gatcagcctc agccaatgga gcagggaagc agtggtgttt taggaggcaa ggaagagggg    2880
ggcaaaccgg agagaagctc aagtccggca tcagcactca ccccagaagg ggaagccacc    2940
agcgtgacct tggtagagga gctgagcctg caggaggcaa tgagaaagga gccaggagag    3000
agcagcagca gaaaggcctg cgaagtgtgt ggccaggcct ttccctccca ggcagctctg    3060
gaggagcatc agaagaccca ccccaaggag gggccgctct tcacttgtgt tttctgcagg    3120
cagggctttc ttgagcgggc taccctcaag aagcatatgc tcctggcaca ccaccaggta    3180
cagcccttgg cccccatgg ccctcagaat attgctgctc tttctctagt ccctggctgt    3240
tcgccttcca tcacctccac agggctctcc cctttcccc gaaaagatga ccccacgatc    3300
ccatgagcct gttttctgt acctgctgct ctttgtccca cagagcagaa acagcttcac    3360
aaaaggacct cccagagtta tgagcccctga ttttgtcttt ttctctaagt tcttaacatg    3420
ttatgtccct agtggctttt ctgtagtccc tgagcttgga aattactgtg cttacaaggg    3480
gatggccccc taaggaattt ttcttccctc ctcattcttt gtacctgagg aacatagatt    3540
ctctgcagct ttctcaaggg gaaccctctc cagcttccct ggtgtgaccc ttcttccccc    3600
tcctctctcc tctcccttc cctttggtag gtgcacctga gcacctacat ttggcattgc    3660
```

```
agcctagcca aaaagggctg gcagctgtct ctggagggcc cagtgccact cctctggggt    3720
gacctttctg ctcagctggt gggtatgggt ccctatctt tctagaacca gtatgtggca    3780
ttcctgtcaa atggcctgcc catgaagccc tggaattcca gctccacctc cactaccact    3840
ccaagcctgg ccccaccagt gctgtttggc ctaggaactg tggctgggaa ggtgcctcca    3900
acaatgggat ccagggaagc caaggagaag acagcccccc tcctatttca gcctcctgca    3960
cccaaggcag tgcctgagaa gcccatcata gacaagaagt agcaaactgt acattccttc    4020
ttcctccccc tgctccagaa ggtgccggta ctgaagatgc tccagtaatt ggtgacccaa    4080
ccctaggaag tagggagaaa tgaaggaagg cataggaaa attttcccag taaatcccct    4140
gatggtcaca ttaaggtaaa ggttttggct ggtcagtgtg ccaagacctc tccagcttct    4200
cattcatgat gacctctcaa agttgggaaa caagctgatt tcttgccaag aggtctccca    4260
ggagatattt gggaaatgtg aagttcgtat ctttaaggag cattttttggt cagcatggtt    4320 gatgaactaa tgatgagaga gttaaggaat gttgctagaa catagggctt gctggtacct    4380
atgtgactaa gaaagggaca tgatgtaagg gaaaaggcct caaattcttg tgaatgtgga    4440
cattctcgtt aatattcttt tgggctaata gtgacatagt gtgcagaggt gtaccaggga    4500
tcatggggga tttcctagca ctagtatgct tctagtttta gataactccc tcctttattc    4560 cctgcccct tgtattttcc ttatcttcct ctttcaagac ccctacccat tttgcctatc    4620
cgtaggctgg ggcttgtgtc tttgtcattg tctggttctt aagagtccca gctccaggtg    4680
gcgtcctccc tgcctctccg tcttgtaatg agttgtagta tttactctta acataggatc    4740
atttggaaca ggagttctga ggaggagaga gtgagggttt tgctattgac tgacttgaac    4800
gatggcttct cctcaagctg taggctccag agcttcctaa cctagtaaaa tgtcaagaac    4860
agacgggaga tattagtgtc tttccctcta tcattaaagg tgttttaacc aaaaaaaaaa    4920
aaaaaaaaaa a                                                        4931

<210> SEQ ID NO 4
<211> LENGTH: 4775
<212> TYPE: DNA
<213> ORGANISM: Homo sapiens

<400> SEQUENCE: 4
atgtctcggc gcaagcaggc caagccccag cacctcaagt cggacgagga gctgctgccg      60
cctgacgggg ctcccgagca cgccgccccg ggggaaggtg cggaggacgc agacagcggg     120
cccgagagcc gcagcggggg cgaggagacc agcgtgtgcg agaaatgctg cgccgagttc     180
ttcaagtggg cggacttcct ggagcaccag cggagctgca ccaagctccc gcccgtgctg     240
atcgtgcacg aggacgcgcc cgcgccgccc ccgaggact tccccgagcc ttcgcccgcc     300
agctccccca gcgagcgcgc cgaaagcgag gcggccgagg aggcgggtgc ggagggcgcg     360
gagggcgagg ccaggccggt ggagaaggag gccgagccca tggacgcgga cccgcggggg     420
gacacgcgcg cgccccggcc cccgcctgcg gcccctgcac cccaacgcc cgcctacggc     480 gcgcccagca ccaacgtgac cctggaggcg ctgctgagca ccaaggtggc ggtggcgcag     540
ttctcgcagg gcgcgcgcgc ggcaggcggc tcggagcag tggaggcgt ggcagctgca     600 gccgtgcccc tgatcctgga acagctcatg gccctgcagc agcagcagat ccaccagctg     660
cagctcatcg agcagatccg cagccaggtg gccctcatgc agcgcccgcc gcgcggcc     720 tcactcagcc ccgcggccgc cccgagcgca ccgggccccgg ccccagcca gctgcccggg     780
```

```
ctggccgcgc tcccgctgtc ggccggggcc cctgccgccg ccatcgcggg ctcgggcccc      840
gccgccccgg ccgccttcga gggcgcgcag ccgctgtccc ggcccgagtc tggcgccagc      900
accccggcg gccctgcgga gcccagcgcg cccgccgccc ccagcgccgc cctgcccccc       960
gctgcccccg ccccggcgcc agcgccgcag agcgcagcct cgtcgcagcc gcagagcgca     1020
tccacgccgc ctgccctggc cccggggtcc ctgctgggtg cggcgcccgg cctgccaagt     1080
ccgcttctac ctcagacttc cgccagcggc gtcatcttcc ccaacccgct ggtcagcatc     1140
gcggccacgg ccaacgctct ggacccgctg tccgcgctca tgaagcaccg caagggcaag     1200
ccgcccaatg tgtcggtgtt cgagcccaaa gccagcgccg aggacccgtt cttcaagcac     1260
aaatgccgct tctgcgccaa ggtcttcggc agcgacagcg cgctccagat ccacctgcgc     1320
tcgcacacag gcgagcggcc cttcaagtgc aacatctgcg ggaaccgctt ctccaccaaa     1380
ggcaacctga aggtgcactt ccagaggcac aaggagaagt accccacat ccagatgaac      1440
ccttacccgg tccccgagta cctggacaac gtgcccacct gctcgggcat cccctacggc     1500
atgtcgctgc cccccgagaa gcccgtgacc acctggctgg acagcaagcc cgtgctgccc     1560
accgtgccca cgtccgtggg gctgcaactg ccgcccactg tccctggcgc gcacggctac     1620
gccgactctc ccagcgccac cccagccagc cgctccccgc agaggccctc gcccgcctcc     1680
agcgagtgcg cctccttgtc cccaggcctc aaccacgtgg agtccggcgt gtcggccacc     1740
gccgagtccc cacagtcgct cctcggcggg ccgcccctca ctaaagccga gcccgtcagc     1800
ctgccctgca ccaacgccag ggccggggac gctcccgtgg gcgcgcaggc tagcgctgca     1860
cccacatcgg tggacggcgc acccacgagc ctcggcagcc ccgggctgcc cgccgtctcc     1920
gagcagttca aggcccagtt tccgttcggg gggctgctag actcgatgca aacgtcggaa     1980
acctcgaagc tgcagcagct ggtggagaac atcgacaaga agatgacgga cccgaaccag     2040
tgcgtcatct gccaccgggt gctgagctgc cagagcgcgc tgaagatgca ctaccggacg     2100
cacacgggg agcggccgtt caagtgcaag atctgcggcc gcgccttcac caccaagggc     2160
aacctcaaga cgcacttcgg cgtgcaccgt gcaaagccgc ccctgcgcgt gcagcactcc     2220
tgccccatct gccagaagaa gttcaccaac gccgtggtcc tgcagcagca catccgcatg     2280
cacatgggcg gccagatccc caacacgccg ctgccggagg gcttccagga tgccatggac     2340
tccgagctgg cctacgacga caagaacgcg gagaccctga gcagctacga tgacgacatg     2400
gacgagaact ccatggagga cgacgctgag ctgaaggacg cggccaccga cccggccaag     2460
ccactcctgt cctacgcggg gtcctgcccg ccctccccgc cctcggtcat ctccagcatt     2520
gccgccctgg agaaccagat gaagatgatc gactcggtca tgagctgcca gcagctgacc     2580
ggcctcaagt ccgtggagaa cgggtccggg gagagtgacc gcctgagcaa cgactcctcg     2640
tcggccgtgg gcgacctgga gagccgcagc gcgggcagcc ccgccctgtc cgagtcctcg     2700
tcctcgcagg ccctgtcgcc ggccccagc aatggtgaga gcttccgctc caagtccccg     2760
ggcctgggcg ccccggagga gccccaggaa atcccgctca agaccgagag gccggacagc     2820
ccagccgccg ccccgggcag cggaggcgcc cctggccgcg cgggcatcaa ggaggaggcg     2880
cccttcagcc tgctgttcct gagcaggag cggggtaagt gtcccagcac tgtgtgtggt      2940
gtctgtggca agccttttgc ttgcaagagc gcgttggaaa tccactaccg cagccatact     3000
aaggagcggc cattcgtctg cgcgctctgc aggcgagggt gctccactat gggtaattta     3060
aaacagcact tactgacaca cagattgaaa gagctgcctt tcagttatt tgaccccaac      3120
tttgctctag gtcccagcca aagcactcct agcctgatct ccagcgccgc acccaccatg     3180
```

-continued

```
atcaaaatgg aagtgaacgg tcacggcaag gccatggcgc tgggcgaggg tcccccgctg    3240
cccgcgggcg tccaggtccc cgccgggcct cagacagtga tgggcccggg cctggcgccc    3300
atgctggccc cccaccgcg ccggacgccc aagcagcaca actgccagtc gtgcgggaag    3360
accttctcct cggccagcgc cctgcagatc catgagcgca cgcacaccgg cgagaagccg    3420
ttcggctgca ccatctgcgg ccgggccttc accactaagg gcaacctcaa ggtgcacatg    3480
gggacacaca tgtggaataa cgcccccgcg agacgcggcc gccgcctgtc tgtggagaac    3540
cccatggctc tcctagggg tgatgccctg aagttctctg aaatgttcca aaggacctg     3600
gcagctcggg caatgaacgt cgaccccagt ttttggaacc agtatgctgc agccatcact    3660
aacgggctcg ccatgaagaa caacgagatc tccgtcatcc agaacggcgg catccccag    3720
ctccccgtga gtcttggggg cagcgccctc cccctctgg gcagcatggc cagtgggatg     3780
gacaaagcac gcactggcag tagcccaccc atcgtcagct tggacaaagc gagctcagaa    3840
acagcagcca gccgcccatt cacgcggttt atcgaggata caaggagat tggtatcaac    3900
tagccagtga ctcgctcatc tgccctgccc aggccacgt tttgaagttg gagcatcagg     3960
cctccgacct tcttgcctc ggttctcatt acactttcac ccatagcaga aaacactttg     4020
tgcggctgcc gagaggtggt cttgtaagcg ctgcatggcg ctccccttcaa cagcaagcct    4080
gactgttctc gagaactctg caatctttta aataagcttc cttcaaaaaa aaagtgcttt    4140
ggaaaaccgc cttaggaaca gaaagagctc agaccatgtc cacttccttt ctcctgaaac    4200
ctaataatct ctccgaggga gaaggggtt tctgcggta ttccagtgaa actcatttga     4260
tggtttcttt tgaattagtt agacacttga acggtgtttt ttagaactct tcatgttaaa    4320
gacgtggttt agtactccca atgctgtgta tcatgacact atcttcgtct gtagtattta    4380
tgatgttaag ataatgcggg taacagacaa tataatagcc ccgaccttaa acgaagcttt    4440
tgtactgcag aatacatctg gctgtgtgat ttttttttt aagcaagatt tgttttacta    4500
taaataagtg gattatttca atgcaggcaa aattgtgaag ttctgttggg aaagatagca    4560
tgcttttcgt gtgcaagtac ctgtcagtaa taagcctttt tttttttttt ttttaattta    4620
aatgtttgta gctgctatgt ggacagttgt tttctagtgt ggtctgtagc ccaataactg    4680
gggaacgagt tacagacaaa catcaccgta aatgactcac aacattataa acagttgtga    4740
gaaaatattt cacattatca aagctgtaca ataaa                              4775
```

<210> SEQ ID NO 5
<211> LENGTH: 3162
<212> TYPE: DNA
<213> ORGANISM: Homo sapiens

<400> SEQUENCE: 5

```
atgtcgaggc gcaagcaggc gaaaccccag cacatcaact cggaggagga ccagggcgag      60
cagcagccgc agcagcagac cccggagttt cagatgcgg cccagcggc gcccgcggcg      120
ggggagctgg gtgctccagt gaaccaccca gggaatgacg aggtggcgag tgaggatgaa      180
gccacagtaa agcggcttcg tcgggaggag acgcacgtct gtgagaaatg ctgtgcggag      240
ttcttcagca tctctgagtt cctggaacat aagaaaaatt gcactaaaaa tccacctgtc      300
ctcatcatga atgacagcga ggggcctgtg ccttcagaag acttctccgg agctgtactg      360
agccaccagc ccaccagtcc cggcagtaag gactgtcaca gggagaatgg cggcagctca      420
gaggacatga aggagaagcc ggatgcggag tctgtggtgt acctaaagac agagacagcc      480
```

-continued

```
ctgccaccca ccccccagga cataagctat ttagccaaag gcaaagtggc caacactaat      540
gtgaccttgc aggcactacg gggcaccaag gtggcggtga atcagcggag cgcggatgca      600
ctccctgccc ccgtgcctgg tgccaacagc atcccgtggg tcctcgagca gatcttgtgt      660
ctgcagcagc agcagctaca gcagatccag ctcaccgagc agatccgcat ccaggtgaac      720
atgtgggcct cccacgccct ccactcaagc ggggcagggg ccgacactct gaagaccttg      780
ggcagccaca tgtctcagca ggtttctgca gctgtggctt tgctcagcca gaaagctgga      840
agccaaggtc tgtctctgga tgccttgaaa caagccaagc tacctcacgc caacatccct      900
tctgccacca gctccctgtc cccagggctg gcacccttca ctctgaagcc ggatgggacc      960
cgggtgctcc cgaacgtcat gtcccgcctc ccgagcgctt tgcttcctca ggccccgggc     1020
tcggtgctct tccagagccc tttctccact gtggcgctag acacatccaa gaaagggaag     1080
gggaagccac cgaacatctc cgcggtggat gtcaaaccca agacgaggc ggccctctac      1140
aagcacaagt gtaagtactg tagcaaggtt tttgggactg atagctcctt gcagatccac     1200
ctccgctccc acactggaga gagacccttc gtgtgctctg tctgtggtca tcgcttcacc     1260
accaagggca acctcaaggt gcactttcac cgacatcccc aggtgaaggc aaaccccag      1320
ctgtttgccg agtccagga caaagtggcg gccggcaatg gcatcccta tgcactctct       1380
gtacctgacc ccatagatga accgagtctt tctttagaca gcaaacctgt ccttgtaacc     1440
acctctgtag ggctacctca gaatctttct tcggggacta atcccaagga cctcacgggt     1500
ggctccttgc ccggtgacct gcagcctggg ccttctccag aaagtgaggg tggacccaca    1560
ctccctgggg tgggaccaaa ctataattcc ccaagggctg gtggcttcca agggagtggg    1620
acccctgagc cagggtcaga gaccctgaaa ttgcagcagt tggtggagaa cattgacaag    1680
gccaccactg atcccaacga atgtctcatt tgccaccgag tcttaagctg tcagagctcc   1740
ctcaagatgc attatcgcac ccacaccggg gagagaccgt tccagtgtaa gatctgtggc   1800
cgagccttt ctaccaaagg taacctgaag acacaccttg gggttcaccg aaccaacaca    1860
tccattaaga cgcagcattc gtgccccatc tgccagaaga gttcactaa tgccgtgatg   1920
ctgcagcaac atattcggat gcacatgggc ggtcagattc caacacgcc cctgccagag   1980
aatccctgtg actttacggg ttctgagcca atgaccgtgg gtgagaacgg cagcaccggc    2040
gctatctgcc atgatgatgt catcgaaagc atcgatgtag aggaagtcag ctcccaggag    2100
gctcccagca gctcctccaa ggtccccacg cctcttccca gcatccactc ggcatcaccc    2160
acgctagggt ttgccatgat ggcttcctta gatgccccag ggaaagtggg tcctgccct     2220
tttaacctgc agcgccaggg cagcagagaa acggttccg tggagagcga tggcttgacc     2280
aacgactcat cctcgctgat gggagaccag gagtatcaga gccgaagccc agatatcctg    2340
gaaaccacat ccttccaggc actctccccg gccaatagtc aagccgaaag catcaagtca    2400
aagtctcccg atgctgggag caaagcagag agctccgaga acagccgcac tgagatggaa    2460
ggtcggagca gtctcccttc cacgtttatc cgagccccgc cgacctatgt caaggttgaa    2520
gttcctggca catttgtggg accctcgaca ttgtccccag gatgacccc tttgttagca     2580
gcccagccac gccgacaggc caagcaacat ggctgcacac ggtgtgggaa gaacttctcg    2640
tctgctagcg ctcttcagat ccacgagcgg actcacactg gagagaagcc ttttgtgtgc    2700
aacatttgtg gcgagctttt taccaccaaa ggcaacttaa aggttcacta catgacacac    2760
ggggcgaaca ataactcagc ccgccgtgga aggaagttgg ccatcgagaa caccatggct    2820
ctgttaggta cggacggaaa aagagtctca gaaatctttc ccaaggaaat cctggcccct    2880
```

```
tcagtgaatg tggaccctgt tgtgtggaac cagtacacca gcatgctcaa tggcggtctg    2940
gccgtgaaga ccaatgagat ctctgtgatc cagagtgggg gggttcctac cctcccggtt    3000
tccttggggg ccacctccgt tgtgaataac gccactgtct ccaagatgga tggctcccag    3060
tcgggtatca gtgcagatgt ggaaaaacca agtgctactg acggcgttcc caaacaccag    3120
tttcctcact tcctggaaga aaacaagatt gcggtcagct aa                       3162
```

<210> SEQ ID NO 6
<211> LENGTH: 1851
<212> TYPE: DNA
<213> ORGANISM: Homo sapiens
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (1317)..(1317)
<223> OTHER INFORMATION: n is a, c, g, or t
<220> FEATURE:
<221> NAME/KEY: misc_feature
<222> LOCATION: (1326)..(1326)
<223> OTHER INFORMATION: n is a, c, g, or t
<220> FEATURE:
<221> NAME/KEY: misc_feature
<222> LOCATION: (1331)..(1331)
<223> OTHER INFORMATION: n is a, c, g, or t
<220> FEATURE:
<221> NAME/KEY: misc_feature
<222> LOCATION: (1334)..(1334)
<223> OTHER INFORMATION: n is a, c, g, or t
<220> FEATURE:
<221> NAME/KEY: misc_feature
<222> LOCATION: (1367)..(1367)
<223> OTHER INFORMATION: n is a, c, g, or t
<220> FEATURE:
<221> NAME/KEY: misc_feature
<222> LOCATION: (1805)..(1805)
<223> OTHER INFORMATION: n is a, c, g, or t
<220> FEATURE:
<221> NAME/KEY: misc_feature
<222> LOCATION: (1838)..(1838)
<223> OTHER INFORMATION: n is a, c, g, or t

<400> SEQUENCE: 6

```
atgtcgaggc gcaagcaggc gaaacccag cacatcaact cggaggagga ccagggcgag      60
cagcagccgc agcagcagac cccggagttt gcagatgcgg ccccagcggc gcccgcggcg    120
ggggagctgg gtgctccagt gaaccaccca gggaatgacg aggtggcgag tgaggatgaa    180
gccacagtaa agcggcttcg tcgggaggag acgcacgtct gtgagaaatg ctgtgcggag    240
ttcttcagca tctctgagtt cctggaacat aagaaaaatt gcactaaaaa tccacctgtc    300
ctcatcatga atgacagcga ggggcctgtg ccttcanaag acttctccgg agctgtactg    360
agccaccagc ccaccagtcc cggcagtgag gactgtcaca gggagaatgg cggcagctca    420
naggacataa aggagaagcc ggatgcggag tctgtggtgt acctaaagac agagacagcc    480
ctgccaccca cccccaggga cataagctat ttagccaaag gcaaagtggc caacactaac    540
gtgaccttgc aggcactacg gggcaccaag gtggcggtga atcagcggag gcgggatgca    600
ctccctgccc ccgtgcctgg tgccaacagc atcccgtggg tcctgagcca gatcttgtgt    660
ctgcagcagc agcagctaca gcagatccag ctcaccgagc agatccgcat ccaggtgaac    720
```

```
atgtgggcct cccacgccct ccactcaagc ggggcagggg ccgacactct gaagaccttg    780
ggcagccaca tgtctcagca ggtttctgca gctgtggctt tgctcagcca gaaagctgga    840
agccaaggtc tgtctctgga tgccttgaaa caagccaagc tacctcacgc caacatccct    900
tctgccacca gctccctgtc cccagggctg gcacccttca ctctgaagcc ggatgggacc    960
cgggtgctcc cgaacgtcat gtcccgcctc ccgagcgctt tgcttcctca ggccccgggc   1020
tcggtgctct tccagagccc tttctccact gtggcgctag acacatccaa gaaagggaag   1080
gggaagccac cgaacatctc cgcggtggat gtcaaaccca agacgaggc ggccctctac   1140
aagcacaagt gtcggagcag tctccctttcc acgtttatcc gagccccgcc gacctatgtc   1200
aaggttgaag ttcctggcac atttgtggga ccctcgacat tgtccccagg gatgacccct   1260
tgttagcag cccagccacg cggacaggcc aagcaacatg gctgcacacg tgtggnaag    1320
aacttntcgt ntgntagcgc tcttcagatc cacgagcgga ctcacantgg agagaagcct   1380
tttgtgtgca acatttgtgg gcgagctttt accaccaaag gcaacttaaa ggttcactac   1440
atgacacacg gggcgaacaa taactcagcc cgccgtggaa ggaagttggc catcgagaac   1500
accatggctc tgttaggtac ggacggaaaa agagtctcag aaatctttcc caaggaaatc   1560
ctggccccct cagtgaatgt ggaccctgtt gtgtggaacc agtacaccag catgctcaat   1620
ggcggtctgg ccgtgaagac caatgagatc tctgtgatcc agagtggggg ggttcctacc   1680
ctcccggttt ccttgggggc cacctccgtt gtgaataacg ccactgtctc caagatggat   1740
ggctcccagt cgggtatcag tgcagatgtg gaaaaaccaa gtgctactga cggcgttccc   1800
aaacnccagt ttcctcactt cctggaagaa acaagantg cggtcagcta a            1851
```

<210> SEQ ID NO 7
<211> LENGTH: 1320
<212> TYPE: PRT
<213> ORGANISM: Homo sapiens

<400> SEQUENCE: 7

Met Ser Arg Arg Lys Gln Ala Lys Pro Gln His Phe Gln Ser Asp Pro
1               5                   10                  15

Glu Val Ala Ser Leu Pro Arg Arg Asp Gly Asp Thr Glu Lys Gly Gln
            20                  25                  30

Pro Ser Arg Pro Thr Lys Ser Lys Asp Ala His Val Cys Gly Arg Cys
        35                  40                  45

Cys Ala Glu Phe Phe Glu Leu Ser Asp Leu Leu Leu His Lys Lys Asn
    50                  55                  60

Cys Thr Lys Asn Gln Leu Val Leu Ile Val Asn Glu Asn Pro Ala Ser
65                  70                  75                  80

Pro Pro Glu Thr Phe Ser Pro Ser Pro Pro Asp Asn Pro Asp Glu
            85                  90                  95

Gln Met Asn Asp Thr Val Asn Lys Thr Asp Gln Val Asp Cys Ser Asp
            100                 105                 110

Leu Ser Glu His Asn Gly Leu Asp Arg Glu Glu Ser Met Glu Val Glu
        115                 120                 125

Ala Pro Val Ala Asn Lys Ser Gly Ser Gly Thr Ser Gly Ser His
    130                 135                 140

Ser Ser Thr Ala Pro Ser Ser Ser Ser Ser Ser Ser Ser Gly
145                 150                 155                 160

Gly Gly Gly Ser Ser Thr Gly Thr Ser Ala Ile Thr Thr Ser Leu
            165                 170                 175

```
Pro Gln Leu Gly Asp Leu Thr Thr Leu Gly Asn Phe Ser Val Ile Asn
            180                 185                 190

Ser Asn Val Ile Ile Glu Asn Leu Gln Ser Thr Lys Val Ala Val Ala
        195                 200                 205

Gln Phe Ser Gln Glu Ala Arg Cys Gly Gly Ala Ser Gly Gly Lys Leu
    210                 215                 220

Ala Val Pro Ala Leu Met Glu Gln Leu Leu Ala Leu Gln Gln Gln Gln
225                 230                 235                 240

Ile His Gln Leu Gln Leu Ile Glu Gln Ile Arg His Gln Ile Leu Leu
                245                 250                 255

Leu Ala Ser Gln Asn Ala Asp Leu Pro Thr Ser Ser Pro Ser Gln
        260                 265                 270

Gly Thr Leu Arg Thr Ser Ala Asn Pro Leu Ser Thr Leu Ser Ser His
        275                 280                 285

Leu Ser Gln Gln Leu Ala Ala Ala Gly Leu Ala Gln Ser Leu Ala
        290                 295                 300

Ser Gln Ser Ala Ser Ile Ser Gly Val Lys Gln Leu Pro Pro Ile Gln
305                 310                 315                 320

Leu Pro Gln Ser Ser Gly Asn Thr Ile Ile Pro Ser Asn Ser Gly
            325                 330                 335

Ser Ser Pro Asn Met Asn Ile Leu Ala Ala Ala Val Thr Thr Pro Ser
            340                 345                 350

Ser Glu Lys Val Ala Ser Ser Ala Gly Ala Ser His Val Ser Asn Pro
            355                 360                 365

Ala Val Ser Ser Ser Ser Pro Ala Phe Ala Ile Ser Ser Leu Leu
        370                 375                 380

Ser Pro Ala Ser Asn Pro Leu Leu Pro Gln Gln Ala Ser Ala Asn Ser
385                 390                 395                 400

Val Phe Pro Ser Pro Leu Pro Asn Ile Gly Thr Thr Ala Glu Asp Leu
            405                 410                 415

Asn Ser Leu Ser Ala Leu Ala Gln Gln Arg Lys Ser Lys Pro Pro Asn
            420                 425                 430

Val Thr Ala Phe Glu Ala Lys Ser Thr Ser Asp Glu Ala Phe Phe Lys
            435                 440                 445

His Lys Cys Arg Phe Cys Ala Lys Val Phe Gly Ser Asp Ser Ala Leu
    450                 455                 460

Gln Ile His Leu Arg Ser His Thr Gly Glu Arg Pro Phe Lys Cys Asn
465                 470                 475                 480

Ile Cys Gly Asn Arg Phe Ser Thr Lys Gly Asn Leu Lys Val His Phe
                485                 490                 495

Gln Arg His Lys Glu Lys Tyr Pro His Ile Gln Met Asn Pro Tyr Pro
            500                 505                 510

Val Pro Glu His Leu Asp Asn Ile Pro Thr Ser Thr Gly Ile Pro Tyr
            515                 520                 525

Gly Met Ser Ile Pro Pro Glu Lys Pro Val Thr Ser Trp Leu Asp Thr
        530                 535                 540

Lys Pro Val Leu Pro Thr Leu Thr Thr Ser Val Gly Leu Pro Leu Pro
545                 550                 555                 560

Pro Thr Leu Pro Ser Leu Ile Pro Phe Ile Lys Thr Glu Glu Pro Ala
                565                 570                 575

Pro Ile Pro Ile Ser His Ser Ala Thr Ser Pro Pro Gly Ser Val Lys
            580                 585                 590

Ser Asp Ser Gly Gly Pro Glu Ser Ala Thr Arg Asn Leu Gly Gly Leu
```

-continued

```
                595                 600                 605
Pro Glu Glu Ala Glu Gly Ser Thr Leu Pro Ser Gly Gly Lys Ser
    610                 615                 620
Glu Glu Ser Gly Met Val Thr Asn Ser Val Pro Thr Ala Ser Ser
625                 630                 635                 640
Val Leu Ser Ser Pro Ala Ala Asp Cys Gly Pro Ala Gly Ser Ala Thr
                    645                 650                 655
Thr Phe Thr Asn Pro Leu Leu Pro Leu Met Ser Glu Gln Phe Lys Ala
                660                 665                 670
Lys Phe Pro Phe Gly Gly Leu Leu Asp Ser Ala Gln Ala Ser Glu Thr
            675                 680                 685
Ser Lys Leu Gln Gln Leu Val Glu Asn Ile Asp Lys Lys Ala Thr Asp
690                 695                 700
Pro Asn Glu Cys Ile Ile Cys His Arg Val Leu Ser Cys Gln Ser Ala
705                 710                 715                 720
Leu Lys Met His Tyr Arg Thr His Thr Gly Glu Arg Pro Phe Lys Cys
                725                 730                 735
Lys Ile Cys Gly Arg Ala Phe Thr Thr Lys Gly Asn Leu Lys Thr His
            740                 745                 750
Tyr Ser Val His Arg Ala Met Pro Pro Leu Arg Val Gln His Ser Cys
        755                 760                 765
Pro Ile Cys Gln Lys Lys Phe Thr Asn Ala Val Val Leu Gln Gln His
770                 775                 780
Ile Arg Met His Met Gly Gly Gln Ile Pro Asn Thr Pro Val Pro Asp
785                 790                 795                 800
Ser Tyr Ser Glu Ser Met Glu Ser Asp Thr Gly Ser Phe Asp Glu Lys
                805                 810                 815
Asn Phe Asp Asp Leu Asp Asn Phe Ser Asp Glu Asn Met Glu Asp Cys
                820                 825                 830
Pro Glu Gly Ser Ile Pro Asp Thr Pro Lys Ser Ala Asp Ala Ser Gln
            835                 840                 845
Asp Ser Leu Ser Ser Ser Pro Leu Pro Leu Glu Met Ser Ser Ile Ala
850                 855                 860
Ala Leu Glu Asn Gln Met Lys Met Ile Asn Ala Gly Leu Ala Glu Gln
865                 870                 875                 880
Leu Gln Ala Ser Leu Lys Ser Val Glu Asn Gly Ser Ile Glu Gly Asp
                885                 890                 895
Val Leu Thr Asn Asp Ser Ser Val Gly Gly Asp Met Glu Ser Gln
                900                 905                 910
Ser Ala Gly Ser Pro Ala Ile Ser Glu Ser Thr Ser Ser Met Gln Ala
            915                 920                 925
Leu Ser Pro Ser Asn Ser Thr Gln Glu Phe His Lys Ser Pro Ser Ile
        930                 935                 940
Glu Glu Lys Pro Gln Arg Ala Val Pro Ser Glu Phe Ala Asn Gly Leu
945                 950                 955                 960
Ser Pro Thr Pro Val Asn Gly Gly Ala Leu Asp Leu Thr Ser Ser His
                965                 970                 975
Ala Glu Lys Ile Ile Lys Glu Asp Ser Leu Gly Ile Leu Phe Pro Phe
                980                 985                 990
Arg Asp Arg Gly Lys Phe Lys Asn Thr Ala Cys Asp Ile Cys Gly Lys
            995                 1000                1005
Thr Phe Ala Cys Gln Ser Ala Leu Asp Ile His Tyr Arg Ser His
        1010                1015                1020
```

Thr Lys Glu Arg Pro Phe Ile Cys Thr Val Cys Asn Arg Gly Phe
1025                1030                1035

Ser Thr Lys Gly Asn Leu Lys Gln His Met Leu Thr His Gln Met
    1040                1045                1050

Arg Asp Leu Pro Ser Gln Leu Phe Glu Pro Ser Ser Asn Leu Gly
    1055                1060                1065

Pro Asn Gln Asn Ser Ala Val Ile Pro Ala Asn Ser Leu Ser Ser
    1070                1075                1080

Leu Ile Lys Thr Glu Val Asn Gly Phe Val His Val Ser Pro Gln
    1085                1090                1095

Asp Ser Lys Asp Thr Pro Thr Ser His Val Pro Ser Gly Pro Leu
    1100                1105                1110

Ser Ser Ser Ala Thr Ser Pro Val Leu Leu Pro Ala Leu Pro Arg
    1115                1120                1125

Arg Thr Pro Lys Gln His Tyr Cys Asn Thr Cys Gly Lys Thr Phe
    1130                1135                1140

Ser Ser Ser Ser Ala Leu Gln Ile His Glu Arg Thr His Thr Gly
    1145                1150                1155

Glu Lys Pro Phe Ala Cys Thr Ile Cys Gly Arg Ala Phe Thr Thr
    1160                1165                1170

Lys Gly Asn Leu Lys Val His Met Gly Thr His Met Trp Asn Ser
    1175                1180                1185

Thr Pro Ala Arg Arg Gly Arg Arg Leu Ser Val Asp Gly Pro Met
    1190                1195                1200

Thr Phe Leu Gly Gly Asn Pro Val Lys Phe Pro Glu Met Phe Gln
    1205                1210                1215

Lys Asp Leu Ala Ala Arg Ser Gly Ser Gly Asp Pro Ser Ser Phe
    1220                1225                1230

Trp Asn Gln Tyr Ala Ala Ala Leu Ser Asn Gly Leu Ala Met Lys
    1235                1240                1245

Ala Asn Glu Ile Ser Val Ile Gln Asn Gly Gly Ile Pro Pro Ile
    1250                1255                1260

Pro Gly Ser Leu Gly Ser Gly Asn Ser Ser Pro Val Ser Gly Leu
    1265                1270                1275

Thr Gly Asn Leu Glu Arg Leu Gln Asn Ser Glu Pro Asn Ala Pro
    1280                1285                1290

Leu Ala Gly Leu Glu Lys Met Ala Ser Ser Glu Asn Gly Thr Asn
    1295                1300                1305

Phe Arg Phe Thr Arg Phe Val Glu Asp Ser Lys Glu
    1310                1315                1320

<210> SEQ ID NO 8
<211> LENGTH: 1227
<212> TYPE: PRT
<213> ORGANISM: Homo sapiens

<400> SEQUENCE: 8

Met Asn Asp Thr Val Asn Lys Thr Asp Gln Val Asp Cys Ser Asp Leu
1               5                   10                  15

Ser Glu His Asn Gly Leu Asp Arg Glu Glu Ser Met Glu Val Glu Ala
            20                  25                  30

Pro Val Ala Asn Lys Ser Gly Ser Gly Thr Ser Ser Gly Ser His Ser
        35                  40                  45

Ser Thr Ala Pro Ser Ser Ser Ser Ser Ser Ser Ser Ser Gly Gly

```
                    50                  55                  60
Gly Gly Ser Ser Ser Thr Gly Thr Ser Ala Ile Thr Thr Ser Leu Pro
 65                  70                  75                  80

Gln Leu Gly Asp Leu Thr Thr Leu Gly Asn Phe Ser Val Ile Asn Ser
                     85                  90                  95

Asn Val Ile Ile Glu Asn Leu Gln Ser Thr Lys Val Ala Val Ala Gln
                    100                 105                 110

Phe Ser Gln Glu Ala Arg Cys Gly Gly Ala Ser Gly Gly Lys Leu Ala
                    115                 120                 125

Val Pro Ala Leu Met Glu Gln Leu Leu Ala Leu Gln Gln Gln Gln Ile
                    130                 135                 140

His Gln Leu Gln Leu Ile Glu Gln Ile Arg His Gln Ile Leu Leu Leu
145                 150                 155                 160

Ala Ser Gln Asn Ala Asp Leu Pro Thr Ser Ser Pro Ser Gln Gly
                    165                 170                 175

Thr Leu Arg Thr Ser Ala Asn Pro Leu Ser Thr Leu Ser Ser His Leu
                    180                 185                 190

Ser Gln Gln Leu Ala Ala Ala Gly Leu Ala Gln Ser Leu Ala Ser
                    195                 200                 205

Gln Ser Ala Ser Ile Ser Gly Val Lys Gln Leu Pro Pro Ile Gln Leu
                    210                 215                 220

Pro Gln Ser Ser Gly Asn Thr Ile Ile Pro Ser Asn Ser Gly Ser
225                 230                 235                 240

Ser Pro Asn Met Asn Ile Leu Ala Ala Ala Val Thr Thr Pro Ser Ser
                    245                 250                 255

Glu Lys Val Ala Ser Ala Gly Ala Ser His Val Ser Asn Pro Ala
                    260                 265                 270

Val Ser Ser Ser Ser Pro Ala Phe Ala Ile Ser Ser Leu Leu Ser
                    275                 280                 285

Pro Ala Ser Asn Pro Leu Leu Pro Gln Gln Ala Ser Ala Asn Ser Val
290                 295                 300

Phe Pro Ser Pro Leu Pro Asn Ile Gly Thr Thr Ala Glu Asp Leu Asn
305                 310                 315                 320

Ser Leu Ser Ala Leu Ala Gln Gln Arg Lys Ser Lys Pro Pro Asn Val
                    325                 330                 335

Thr Ala Phe Glu Ala Lys Ser Thr Ser Asp Glu Ala Phe Phe Lys His
                    340                 345                 350

Lys Cys Arg Phe Cys Ala Lys Val Phe Gly Ser Asp Ser Ala Leu Gln
                    355                 360                 365

Ile His Leu Arg Ser His Thr Gly Glu Arg Pro Phe Lys Cys Asn Ile
                    370                 375                 380

Cys Gly Asn Arg Phe Ser Thr Lys Gly Asn Leu Lys Val His Phe Gln
385                 390                 395                 400

Arg His Lys Glu Lys Tyr Pro His Ile Gln Met Asn Pro Tyr Pro Val
                    405                 410                 415

Pro Glu His Leu Asp Asn Ile Pro Thr Ser Thr Gly Ile Pro Tyr Gly
                    420                 425                 430

Met Ser Ile Pro Pro Glu Lys Pro Val Thr Ser Trp Leu Asp Thr Lys
                    435                 440                 445

Pro Val Leu Pro Thr Leu Thr Thr Ser Val Gly Leu Pro Leu Pro Pro
                    450                 455                 460

Thr Leu Pro Ser Leu Ile Pro Phe Ile Lys Thr Glu Glu Pro Ala Pro
465                 470                 475                 480
```

```
Ile Pro Ile Ser His Ser Ala Thr Ser Pro Pro Gly Ser Val Lys Ser
                485                 490                 495

Asp Ser Gly Gly Pro Glu Ser Ala Thr Arg Asn Leu Gly Gly Leu Pro
            500                 505                 510

Glu Glu Ala Glu Gly Ser Thr Leu Pro Pro Ser Gly Gly Lys Ser Glu
            515                 520                 525

Glu Ser Gly Met Val Thr Asn Ser Val Pro Thr Ala Ser Ser Ser Val
        530                 535                 540

Leu Ser Ser Pro Ala Ala Asp Cys Gly Pro Ala Gly Ser Ala Thr Thr
545                 550                 555                 560

Phe Thr Asn Pro Leu Leu Pro Leu Met Ser Glu Gln Phe Lys Ala Lys
                565                 570                 575

Phe Pro Phe Gly Gly Leu Leu Asp Ser Ala Gln Ala Ser Glu Thr Ser
            580                 585                 590

Lys Leu Gln Gln Leu Val Glu Asn Ile Asp Lys Lys Ala Thr Asp Pro
        595                 600                 605

Asn Glu Cys Ile Ile Cys His Arg Val Leu Ser Cys Gln Ser Ala Leu
        610                 615                 620

Lys Met His Tyr Arg Thr His Thr Gly Glu Arg Pro Phe Lys Cys Lys
625                 630                 635                 640

Ile Cys Gly Arg Ala Phe Thr Thr Lys Gly Asn Leu Lys Thr His Tyr
                645                 650                 655

Ser Val His Arg Ala Met Pro Pro Leu Arg Val Gln His Ser Cys Pro
            660                 665                 670

Ile Cys Gln Lys Lys Phe Thr Asn Ala Val Val Leu Gln Gln His Ile
        675                 680                 685

Arg Met His Met Gly Gly Gln Ile Pro Asn Thr Pro Val Pro Asp Ser
690                 695                 700

Tyr Ser Glu Ser Met Glu Ser Asp Thr Gly Ser Phe Asp Glu Lys Asn
705                 710                 715                 720

Phe Asp Asp Leu Asp Asn Phe Ser Asp Glu Asn Met Glu Asp Cys Pro
                725                 730                 735

Glu Gly Ser Ile Pro Asp Thr Pro Lys Ser Ala Asp Ala Ser Gln Asp
            740                 745                 750

Ser Leu Ser Ser Ser Pro Leu Pro Leu Glu Met Ser Ser Ile Ala Ala
        755                 760                 765

Leu Glu Asn Gln Met Lys Met Ile Asn Ala Gly Leu Ala Glu Gln Leu
        770                 775                 780

Gln Ala Ser Leu Lys Ser Val Glu Asn Gly Ser Ile Glu Gly Asp Val
785                 790                 795                 800

Leu Thr Asn Asp Ser Ser Val Gly Gly Asp Met Glu Ser Gln Ser
                805                 810                 815

Ala Gly Ser Pro Ala Ile Ser Glu Ser Thr Ser Ser Met Gln Ala Leu
            820                 825                 830

Ser Pro Ser Asn Ser Thr Gln Glu Phe His Lys Ser Pro Ser Ile Glu
        835                 840                 845

Glu Lys Pro Gln Arg Ala Val Pro Ser Glu Phe Ala Asn Gly Leu Ser
        850                 855                 860

Pro Thr Pro Val Asn Gly Gly Ala Leu Asp Leu Thr Ser Ser His Ala
865                 870                 875                 880

Glu Lys Ile Ile Lys Glu Asp Ser Leu Gly Ile Leu Phe Pro Phe Arg
                885                 890                 895
```

Asp Arg Gly Lys Phe Lys Asn Thr Ala Cys Asp Ile Cys Gly Lys Thr
            900                 905                 910

Phe Ala Cys Gln Ser Ala Leu Asp Ile His Tyr Arg Ser His Thr Lys
        915                 920                 925

Glu Arg Pro Phe Ile Cys Thr Val Cys Asn Arg Gly Phe Ser Thr Lys
    930                 935                 940

Gly Asn Leu Lys Gln His Met Leu Thr His Gln Met Arg Asp Leu Pro
945                 950                 955                 960

Ser Gln Leu Phe Glu Pro Ser Ser Asn Leu Gly Pro Asn Gln Asn Ser
            965                 970                 975

Ala Val Ile Pro Ala Asn Ser Leu Ser Ser Leu Ile Lys Thr Glu Val
        980                 985                 990

Asn Gly Phe Val His Val Ser Pro Gln Asp Ser Lys Asp Thr Pro Thr
    995                 1000                1005

Ser His Val Pro Ser Gly Pro Leu Ser Ser Ser Ala Thr Ser Pro
    1010                1015                1020

Val Leu Leu Pro Ala Leu Pro Arg Arg Thr Pro Lys Gln His Tyr
    1025                1030                1035

Cys Asn Thr Cys Gly Lys Thr Phe Ser Ser Ser Ala Leu Gln
    1040                1045                1050

Ile His Glu Arg Thr His Thr Gly Glu Lys Pro Phe Ala Cys Thr
    1055                1060                1065

Ile Cys Gly Arg Ala Phe Thr Thr Lys Gly Asn Leu Lys Val His
    1070                1075                1080

Met Gly Thr His Met Trp Asn Ser Thr Pro Ala Arg Arg Gly Arg
    1085                1090                1095

Arg Leu Ser Val Asp Gly Pro Met Thr Phe Leu Gly Gly Asn Pro
    1100                1105                1110

Val Lys Phe Pro Glu Met Phe Gln Lys Asp Leu Ala Ala Arg Ser
    1115                1120                1125

Gly Ser Gly Asp Pro Ser Ser Phe Trp Asn Gln Tyr Ala Ala Ala
    1130                1135                1140

Leu Ser Asn Gly Leu Ala Met Lys Ala Asn Glu Ile Ser Val Ile
    1145                1150                1155

Gln Asn Gly Gly Ile Pro Pro Ile Pro Gly Ser Leu Gly Ser Gly
    1160                1165                1170

Asn Ser Ser Pro Val Ser Gly Leu Thr Gly Asn Leu Glu Arg Leu
    1175                1180                1185

Gln Asn Ser Glu Pro Asn Ala Pro Leu Ala Gly Leu Glu Lys Met
    1190                1195                1200

Ala Ser Ser Glu Asn Gly Thr Asn Phe Arg Phe Thr Arg Phe Val
    1205                1210                1215

Glu Asp Ser Lys Glu Ile Val Thr Ser
    1220                1225

<210> SEQ ID NO 9
<211> LENGTH: 1007
<212> TYPE: PRT
<213> ORGANISM: Homo sapiens

<400> SEQUENCE: 9

Met Ser Arg Arg Lys Gln Arg Lys Pro Gln Gln Leu Ile Ser Asp Cys
1               5                   10                  15

Glu Gly Pro Ser Ala Ser Glu Asn Gly Asp Ala Ser Glu Glu Asp His
            20                  25                  30

```
Pro Gln Val Cys Ala Lys Cys Cys Ala Gln Phe Thr Asp Pro Thr Glu
        35                  40                  45

Phe Leu Ala His Gln Asn Ala Cys Ser Thr Asp Pro Pro Val Met Val
    50                  55                  60

Ile Ile Gly Gly Gln Glu Asn Pro Asn Ser Ser Ala Ser Ser Glu
65                  70                  75                  80

Pro Arg Pro Glu Gly His Asn Asn Pro Gln Val Met Asp Thr Glu His
                85                  90                  95

Ser Asn Pro Pro Asp Ser Gly Ser Ser Val Pro Thr Asp Pro Thr Trp
            100                 105                 110

Gly Pro Glu Arg Arg Gly Glu Ser Pro Gly His Phe Leu Val Ala
                115                 120                 125

Ala Thr Gly Thr Ala Ala Gly Gly Gly Gly Leu Ile Leu Ala Ser
        130                 135                 140

Pro Lys Leu Gly Ala Thr Pro Leu Pro Pro Glu Ser Thr Pro Ala Pro
145                 150                 155                 160

Pro Pro Pro Pro Pro Pro Pro Pro Gly Val Gly Ser Gly His
                165                 170                 175

Leu Asn Ile Pro Leu Ile Leu Glu Glu Leu Arg Val Leu Gln Gln Arg
                180                 185                 190

Gln Ile His Gln Met Gln Met Thr Glu Gln Ile Cys Arg Gln Val Leu
        195                 200                 205

Leu Leu Gly Ser Leu Gly Gln Thr Val Gly Ala Pro Ala Ser Pro Ser
        210                 215                 220

Glu Leu Pro Gly Thr Gly Thr Ala Ser Ser Thr Lys Pro Leu Leu Pro
225                 230                 235                 240

Leu Phe Ser Pro Ile Lys Pro Val Gln Thr Ser Lys Thr Leu Ala Ser
                245                 250                 255

Ser Ser Ser Ser Ser Ser Ser Ser Gly Ala Glu Thr Pro Lys Gln
            260                 265                 270

Ala Phe Phe His Leu Tyr His Pro Leu Gly Ser Gln His Pro Phe Ser
        275                 280                 285

Ala Gly Gly Val Gly Arg Ser His Lys Pro Thr Pro Ala Pro Ser Pro
        290                 295                 300

Ala Leu Pro Gly Ser Thr Asp Gln Leu Ile Ala Ser Pro His Leu Ala
305                 310                 315                 320

Phe Pro Ser Thr Thr Gly Leu Leu Ala Ala Gln Cys Leu Gly Ala Ala
                325                 330                 335

Arg Gly Leu Glu Ala Thr Ala Ser Pro Gly Leu Leu Lys Pro Lys Asn
                340                 345                 350

Gly Ser Gly Glu Leu Ser Tyr Gly Glu Val Met Gly Pro Leu Glu Lys
        355                 360                 365

Pro Gly Gly Arg His Lys Cys Arg Phe Cys Ala Lys Val Phe Gly Ser
        370                 375                 380

Asp Ser Ala Leu Gln Ile His Leu Arg Ser His Thr Gly Glu Arg Pro
385                 390                 395                 400

Tyr Lys Cys Asn Val Cys Gly Asn Arg Phe Thr Thr Arg Gly Asn Leu
                405                 410                 415

Lys Val His Phe His Arg His Arg Glu Lys Tyr Pro His Val Gln Met
            420                 425                 430

Asn Pro His Pro Val Pro Glu His Leu Asp Tyr Val Ile Thr Ser Ser
            435                 440                 445
```

```
Gly Leu Pro Tyr Gly Met Ser Val Pro Pro Glu Lys Ala Glu Glu
    450                 455                 460

Ala Ala Thr Pro Gly Gly Gly Val Glu Arg Lys Pro Leu Val Ala Ser
465                 470                 475                 480

Thr Thr Ala Leu Ser Ala Thr Glu Ser Leu Thr Leu Leu Ser Thr Ser
                485                 490                 495

Ala Gly Thr Ala Thr Ala Pro Gly Leu Pro Ala Phe Asn Lys Phe Val
            500                 505                 510

Leu Met Lys Ala Val Glu Pro Lys Asn Lys Ala Asp Glu Asn Thr Pro
        515                 520                 525

Pro Gly Ser Glu Gly Ser Ala Ile Ser Gly Val Ala Glu Ser Ser Thr
    530                 535                 540

Ala Thr Arg Met Gln Leu Ser Lys Leu Val Thr Ser Leu Pro Ser Trp
545                 550                 555                 560

Ala Leu Leu Thr Asn His Phe Lys Ser Thr Gly Ser Phe Pro Phe Pro
                565                 570                 575

Tyr Val Leu Glu Pro Leu Gly Ala Ser Pro Ser Glu Thr Ser Lys Leu
            580                 585                 590

Gln Gln Leu Val Glu Lys Ile Asp Arg Gln Gly Ala Val Ala Val Thr
        595                 600                 605

Ser Ala Ala Ser Gly Ala Pro Thr Thr Ser Ala Pro Ala Pro Ser Ser
    610                 615                 620

Ser Ala Ser Ser Gly Pro Asn Gln Cys Val Ile Cys Leu Arg Val Leu
625                 630                 635                 640

Ser Cys Pro Arg Ala Leu Arg Leu His Tyr Gly Gln His Gly Gly Glu
                645                 650                 655

Arg Pro Phe Lys Cys Lys Val Cys Gly Arg Ala Phe Ser Thr Arg Gly
            660                 665                 670

Asn Leu Arg Ala His Phe Val Gly His Lys Ala Ser Pro Ala Ala Arg
        675                 680                 685

Ala Gln Asn Ser Cys Pro Ile Cys Gln Lys Lys Phe Thr Asn Ala Val
    690                 695                 700

Thr Leu Gln Gln His Val Arg Met His Leu Gly Gly Gln Ile Pro Asn
705                 710                 715                 720

Gly Gly Thr Ala Leu Pro Glu Gly Gly Ala Ala Gln Glu Asn Gly
                725                 730                 735

Ser Glu Gln Ser Thr Val Ser Gly Ala Gly Ser Phe Pro Gln Gln Gln
            740                 745                 750

Ser Gln Gln Pro Ser Pro Glu Glu Leu Ser Glu Glu Glu Glu
        755                 760                 765

Glu Asp Glu Glu Glu Glu Asp Val Thr Asp Glu Asp Ser Leu Ala
    770                 775                 780

Gly Arg Gly Ser Glu Ser Gly Gly Lys Ala Ile Ser Val Arg Gly
785                 790                 795                 800

Asp Ser Glu Glu Ala Ser Gly Ala Glu Glu Val Gly Thr Val Ala
                805                 810                 815

Ala Ala Ala Thr Ala Gly Lys Glu Met Asp Ser Asn Glu Lys Thr Thr
            820                 825                 830

Gln Gln Ser Ser Leu Pro Pro Pro Pro Asp Ser Leu Asp Gln
        835                 840                 845

Pro Gln Pro Met Glu Gln Gly Ser Ser Val Leu Gly Gly Lys Glu
    850                 855                 860

Glu Gly Gly Lys Pro Glu Arg Ser Ser Pro Ala Ser Ala Leu Thr
```

```
865                 870                 875                 880
Pro Glu Gly Glu Ala Thr Ser Val Thr Leu Val Glu Glu Leu Ser Leu
                885                 890                 895
Gln Glu Ala Met Arg Lys Glu Pro Gly Glu Ser Ser Arg Lys Ala
                900                 905                 910
Cys Glu Val Cys Gly Gln Ala Phe Pro Ser Gln Ala Ala Leu Glu Glu
                915                 920                 925
His Gln Lys Thr His Pro Lys Glu Gly Pro Leu Phe Thr Cys Val Phe
                930                 935                 940
Cys Arg Gln Gly Phe Leu Glu Arg Ala Thr Leu Lys Lys His Met Leu
945                 950                 955                 960
Leu Ala His His Gln Val Gln Pro Phe Ala Pro His Gly Pro Gln Asn
                965                 970                 975
Ile Ala Ala Leu Ser Leu Val Pro Gly Cys Ser Pro Ser Ile Thr Ser
                980                 985                 990
Thr Gly Leu Ser Pro Phe Pro Arg Lys Asp Asp Pro Thr Ile Pro
                995                 1000                1005
```

<210> SEQ ID NO 10
<211> LENGTH: 1300
<212> TYPE: PRT
<213> ORGANISM: Homo sapiens

<400> SEQUENCE: 10

```
Met Ser Arg Arg Lys Gln Ala Lys Pro Gln His Leu Lys Ser Asp Glu
1               5                   10                  15
Glu Leu Leu Pro Pro Asp Gly Ala Pro Glu His Ala Ala Pro Gly Glu
                20                  25                  30
Gly Ala Glu Asp Ala Asp Ser Gly Pro Glu Ser Arg Ser Gly Gly Glu
                35                  40                  45
Glu Thr Ser Val Cys Glu Lys Cys Cys Ala Glu Phe Phe Lys Trp Ala
                50                  55                  60
Asp Phe Leu Glu His Gln Arg Ser Cys Thr Lys Leu Pro Pro Val Leu
65              70                  75                  80
Ile Val His Glu Asp Ala Pro Ala Pro Pro Glu Asp Phe Pro Glu
                85                  90                  95
Pro Ser Pro Ala Ser Ser Pro Ser Glu Arg Ala Glu Ser Glu Ala Ala
                100                 105                 110
Glu Glu Ala Gly Ala Glu Gly Ala Glu Gly Glu Ala Arg Pro Val Glu
                115                 120                 125
Lys Glu Ala Glu Pro Met Asp Ala Glu Pro Ala Gly Asp Thr Arg Ala
                130                 135                 140
Pro Arg Pro Pro Ala Ala Pro Ala Pro Pro Thr Pro Ala Tyr Gly
145                 150                 155                 160
Ala Pro Ser Thr Asn Val Thr Leu Glu Ala Leu Leu Ser Thr Lys Val
                165                 170                 175
Ala Val Ala Gln Phe Ser Gln Gly Ala Arg Ala Ala Gly Gly Ser Gly
                180                 185                 190
Ala Gly Gly Gly Val Ala Ala Ala Val Pro Leu Ile Leu Glu Gln Gln
                195                 200                 205
Leu Met Ala Leu Gln Gln Gln Ile His Gln Leu Gln Leu Ile Glu
                210                 215                 220
Gln Ile Arg Ser Gln Val Ala Leu Met Gln Arg Pro Pro Pro Arg Pro
225                 230                 235                 240
```

-continued

```
Ser Leu Ser Pro Ala Ala Pro Ser Ala Pro Gly Pro Ala Pro Ser
            245                 250                 255

Gln Leu Pro Gly Leu Ala Ala Leu Pro Leu Ser Ala Gly Ala Pro Ala
        260                 265                 270

Ala Ala Ile Ala Gly Ser Gly Pro Ala Ala Pro Ala Ala Phe Glu Gly
            275                 280                 285

Ala Gln Pro Leu Ser Arg Pro Glu Ser Gly Ala Ser Thr Pro Gly Gly
        290                 295                 300

Pro Ala Glu Pro Ser Ala Pro Ala Ala Pro Ser Ala Ala Pro Ala Pro
305                 310                 315                 320

Ala Ala Pro Ala Pro Ala Pro Gln Ser Ala Ala Ser Ser Gln
            325                 330                 335

Pro Gln Ser Ala Ser Thr Pro Ala Leu Ala Pro Gly Ser Leu Leu
        340                 345                 350

Gly Ala Ala Pro Gly Leu Pro Ser Pro Leu Leu Pro Gln Thr Ser Ala
            355                 360                 365

Ser Gly Val Ile Phe Pro Asn Pro Leu Val Ser Ile Ala Ala Thr Ala
    370                 375                 380

Asn Ala Leu Asp Pro Leu Ser Ala Leu Met Lys His Arg Lys Gly Lys
385                 390                 395                 400

Pro Pro Asn Val Ser Val Phe Glu Pro Lys Ala Ser Ala Glu Asp Pro
            405                 410                 415

Phe Phe Lys His Lys Cys Arg Phe Cys Ala Lys Val Phe Gly Ser Asp
        420                 425                 430

Ser Ala Leu Gln Ile His Leu Arg Ser His Thr Gly Glu Arg Pro Phe
    435                 440                 445

Lys Cys Asn Ile Cys Gly Asn Arg Phe Ser Thr Lys Gly Asn Leu Lys
450                 455                 460

Val His Phe Gln Arg His Lys Glu Lys Tyr Pro His Ile Gln Met Asn
465                 470                 475                 480

Pro Tyr Pro Val Pro Glu Tyr Leu Asp Asn Val Pro Thr Cys Ser Gly
            485                 490                 495

Ile Pro Tyr Gly Met Ser Leu Pro Pro Glu Lys Pro Val Thr Thr Trp
        500                 505                 510

Leu Asp Ser Lys Pro Val Leu Pro Thr Val Pro Thr Ser Val Gly Leu
    515                 520                 525

Gln Leu Pro Pro Thr Val Pro Gly Ala His Gly Tyr Ala Asp Ser Pro
        530                 535                 540

Ser Ala Thr Pro Ala Ser Arg Ser Pro Gln Arg Pro Ser Pro Ala Ser
545                 550                 555                 560

Ser Glu Cys Ala Ser Leu Ser Pro Gly Leu Asn His Val Glu Ser Gly
            565                 570                 575

Val Ser Ala Thr Ala Glu Ser Pro Gln Ser Leu Leu Gly Gly Pro Pro
        580                 585                 590

Leu Thr Lys Ala Glu Pro Val Ser Leu Pro Cys Thr Asn Ala Arg Ala
    595                 600                 605

Gly Asp Ala Pro Val Gly Ala Gln Ala Ser Ala Pro Thr Ser Val
        610                 615                 620

Asp Gly Ala Pro Thr Ser Leu Gly Ser Pro Gly Leu Pro Ala Val Ser
625                 630                 635                 640

Glu Gln Phe Lys Ala Gln Phe Pro Phe Gly Gly Leu Leu Asp Ser Met
            645                 650                 655

Gln Thr Ser Glu Thr Ser Lys Leu Gln Gln Leu Val Glu Asn Ile Asp
```

```
                660             665             670
Lys Lys Met Thr Asp Pro Asn Gln Cys Val Ile Cys His Arg Val Leu
            675             680             685

Ser Cys Gln Ser Ala Leu Lys Met His Tyr Arg Thr His Thr Gly Glu
            690             695             700

Arg Pro Phe Lys Cys Lys Ile Cys Gly Arg Ala Phe Thr Thr Lys Gly
705             710             715             720

Asn Leu Lys Thr His Phe Gly Val His Arg Ala Lys Pro Pro Leu Arg
            725             730             735

Val Gln His Ser Cys Pro Ile Cys Gln Lys Lys Phe Thr Asn Ala Val
            740             745             750

Val Leu Gln Gln His Ile Arg Met His Met Gly Gly Gln Ile Pro Asn
            755             760             765

Thr Pro Leu Pro Glu Gly Phe Gln Asp Ala Met Asp Ser Glu Leu Ala
            770             775             780

Tyr Asp Asp Lys Asn Ala Glu Thr Leu Ser Ser Tyr Asp Asp Met
785             790             795             800

Asp Glu Asn Ser Met Glu Asp Ala Glu Leu Lys Asp Ala Ala Thr
            805             810             815

Asp Pro Ala Lys Pro Leu Leu Ser Tyr Ala Gly Ser Cys Pro Pro Ser
            820             825             830

Pro Pro Ser Val Ile Ser Ser Ile Ala Ala Leu Glu Asn Gln Met Lys
            835             840             845

Met Ile Asp Ser Val Met Ser Cys Gln Gln Leu Thr Gly Leu Lys Ser
            850             855             860

Val Glu Asn Gly Ser Gly Glu Ser Asp Arg Leu Ser Asn Asp Ser Ser
865             870             875             880

Ser Ala Val Gly Asp Leu Glu Ser Arg Ser Ala Gly Ser Pro Ala Leu
            885             890             895

Ser Glu Ser Ser Ser Ser Gln Ala Leu Ser Pro Ala Pro Ser Asn Gly
            900             905             910

Glu Ser Phe Arg Ser Lys Ser Pro Gly Leu Gly Ala Pro Glu Glu Pro
            915             920             925

Gln Glu Ile Pro Leu Lys Thr Glu Arg Pro Asp Ser Pro Ala Ala Ala
            930             935             940

Pro Gly Ser Gly Gly Ala Pro Gly Arg Ala Gly Ile Lys Glu Glu Ala
945             950             955             960

Pro Phe Ser Leu Leu Phe Leu Ser Arg Glu Arg Gly Lys Cys Pro Ser
            965             970             975

Thr Val Cys Gly Val Cys Gly Lys Pro Phe Ala Cys Lys Ser Ala Leu
            980             985             990

Glu Ile His Tyr Arg Ser His Thr Lys Glu Arg Pro Phe Val Cys Ala
            995             1000            1005

Leu Cys Arg Arg Gly Cys Ser Thr Met Gly Asn Leu Lys Gln His
            1010            1015            1020

Leu Leu Thr His Arg Leu Lys Glu Leu Pro Ser Gln Leu Phe Asp
            1025            1030            1035

Pro Asn Phe Ala Leu Gly Pro Ser Gln Ser Thr Pro Ser Leu Ile
            1040            1045            1050

Ser Ser Ala Ala Pro Thr Met Ile Lys Met Glu Val Asn Gly His
            1055            1060            1065

Gly Lys Ala Met Ala Leu Gly Glu Gly Pro Pro Leu Pro Ala Gly
            1070            1075            1080
```

-continued

```
Val Gln Val Pro Ala Gly Pro Gln Thr Val Met Gly Pro Gly Leu
    1085                1090                1095

Ala Pro Met Leu Ala Pro Pro Arg Arg Thr Pro Lys Gln His
    1100                1105                1110

Asn Cys Gln Ser Cys Gly Lys Thr Phe Ser Ala Ser Ala Leu
    1115                1120                1125

Gln Ile His Glu Arg Thr His Thr Gly Glu Lys Pro Phe Gly Cys
    1130                1135                1140

Thr Ile Cys Gly Arg Ala Phe Thr Thr Lys Gly Asn Leu Lys Val
    1145                1150                1155

His Met Gly Thr His Met Trp Asn Asn Ala Pro Ala Arg Arg Gly
    1160                1165                1170

Arg Arg Leu Ser Val Glu Asn Pro Met Ala Leu Leu Gly Gly Asp
    1175                1180                1185

Ala Leu Lys Phe Ser Glu Met Phe Gln Lys Asp Leu Ala Ala Arg
    1190                1195                1200

Ala Met Asn Val Asp Pro Ser Phe Trp Asn Gln Tyr Ala Ala Ala
    1205                1210                1215

Ile Thr Asn Gly Leu Ala Met Lys Asn Asn Glu Ile Ser Val Ile
    1220                1225                1230

Gln Asn Gly Gly Ile Pro Gln Leu Pro Val Ser Leu Gly Gly Ser
    1235                1240                1245

Ala Leu Pro Pro Leu Gly Ser Met Ala Ser Gly Met Asp Lys Ala
    1250                1255                1260

Arg Thr Gly Ser Ser Pro Pro Ile Val Ser Leu Asp Lys Ala Ser
    1265                1270                1275

Ser Glu Thr Ala Ala Ser Arg Pro Phe Thr Arg Phe Ile Glu Asp
    1280                1285                1290

Asn Lys Glu Ile Gly Ile Asn
    1295                1300

<210> SEQ ID NO 11
<211> LENGTH: 1053
<212> TYPE: PRT
<213> ORGANISM: Homo sapiens

<400> SEQUENCE: 11

Met Ser Arg Arg Lys Gln Ala Lys Pro Gln His Ile Asn Ser Glu Glu
1               5                   10                  15

Asp Gln Gly Glu Gln Gln Pro Gln Gln Gln Thr Pro Glu Phe Ala Asp
                20                  25                  30

Ala Ala Pro Ala Ala Pro Ala Ala Gly Glu Leu Gly Ala Pro Val Asn
            35                  40                  45

His Pro Gly Asn Asp Glu Val Ala Ser Glu Asp Glu Ala Thr Val Lys
        50                  55                  60

Arg Leu Arg Arg Glu Glu Thr His Val Cys Glu Lys Cys Cys Ala Glu
65                  70                  75                  80

Phe Phe Ser Ile Ser Glu Phe Leu Glu His Lys Lys Asn Cys Thr Lys
                85                  90                  95

Asn Pro Pro Val Leu Ile Met Asn Asp Ser Gly Pro Val Pro Ser
                100                 105                 110

Glu Asp Phe Ser Gly Ala Val Leu Ser His Gln Pro Thr Ser Pro Gly
            115                 120                 125

Ser Lys Asp Cys His Arg Glu Asn Gly Gly Ser Ser Glu Asp Met Lys
```

-continued

```
                130                 135                 140
Glu Lys Pro Asp Ala Glu Ser Val Val Tyr Leu Lys Thr Glu Thr Ala
145                 150                 155                 160

Leu Pro Pro Thr Pro Gln Asp Ile Ser Tyr Leu Ala Lys Gly Lys Val
                165                 170                 175

Ala Asn Thr Asn Val Thr Leu Gln Ala Leu Arg Gly Thr Lys Val Ala
                180                 185                 190

Val Asn Gln Arg Ser Ala Asp Ala Leu Pro Ala Pro Val Pro Gly Ala
                195                 200                 205

Asn Ser Ile Pro Trp Val Leu Glu Gln Ile Leu Cys Leu Gln Gln Gln
                210                 215                 220

Gln Leu Gln Gln Ile Gln Leu Thr Glu Gln Ile Arg Ile Gln Val Asn
225                 230                 235                 240

Met Trp Ala Ser His Ala Leu His Ser Ser Gly Ala Gly Ala Asp Thr
                245                 250                 255

Leu Lys Thr Leu Gly Ser His Met Ser Gln Gln Val Ser Ala Ala Val
                260                 265                 270

Ala Leu Leu Ser Gln Lys Ala Gly Ser Gln Gly Leu Ser Leu Asp Ala
                275                 280                 285

Leu Lys Gln Ala Lys Leu Pro His Ala Asn Ile Pro Ser Ala Thr Ser
                290                 295                 300

Ser Leu Ser Pro Gly Leu Ala Pro Phe Thr Leu Lys Pro Asp Gly Thr
305                 310                 315                 320

Arg Val Leu Pro Asn Val Met Ser Arg Leu Pro Ser Ala Leu Leu Pro
                325                 330                 335

Gln Ala Pro Gly Ser Val Leu Phe Gln Ser Pro Phe Ser Thr Val Ala
                340                 345                 350

Leu Asp Thr Ser Lys Lys Gly Lys Gly Lys Pro Pro Asn Ile Ser Ala
                355                 360                 365

Val Asp Val Lys Pro Lys Asp Glu Ala Ala Leu Tyr Lys His Lys Cys
                370                 375                 380

Lys Tyr Cys Ser Lys Val Phe Gly Thr Asp Ser Ser Leu Gln Ile His
385                 390                 395                 400

Leu Arg Ser His Thr Gly Glu Arg Pro Phe Val Cys Ser Val Cys Gly
                405                 410                 415

His Arg Phe Thr Thr Lys Gly Asn Leu Lys Val His Phe His Arg His
                420                 425                 430

Pro Gln Val Lys Ala Asn Pro Gln Leu Phe Ala Glu Phe Gln Asp Lys
                435                 440                 445

Val Ala Ala Gly Asn Gly Ile Pro Tyr Ala Leu Ser Val Pro Asp Pro
450                 455                 460

Ile Asp Glu Pro Ser Leu Ser Leu Asp Ser Lys Pro Val Leu Val Thr
465                 470                 475                 480

Thr Ser Val Gly Leu Pro Gln Asn Leu Ser Ser Gly Thr Asn Pro Lys
                485                 490                 495

Asp Leu Thr Gly Gly Ser Leu Pro Gly Asp Leu Gln Pro Gly Pro Ser
                500                 505                 510

Pro Glu Ser Glu Gly Gly Pro Thr Leu Pro Gly Val Gly Pro Asn Tyr
                515                 520                 525

Asn Ser Pro Arg Ala Gly Gly Phe Gln Gly Ser Gly Thr Pro Glu Pro
                530                 535                 540

Gly Ser Glu Thr Leu Lys Leu Gln Gln Leu Val Glu Asn Ile Asp Lys
545                 550                 555                 560
```

```
Ala Thr Thr Asp Pro Asn Glu Cys Leu Ile Cys His Arg Val Leu Ser
                565                 570                 575

Cys Gln Ser Ser Leu Lys Met His Tyr Arg Thr His Thr Gly Glu Arg
            580                 585                 590

Pro Phe Gln Cys Lys Ile Cys Gly Arg Ala Phe Ser Thr Lys Gly Asn
        595                 600                 605

Leu Lys Thr His Leu Gly Val His Arg Thr Asn Thr Ser Ile Lys Thr
    610                 615                 620

Gln His Ser Cys Pro Ile Cys Gln Lys Lys Phe Thr Asn Ala Val Met
625                 630                 635                 640

Leu Gln Gln His Ile Arg Met His Met Gly Gly Gln Ile Pro Asn Thr
                645                 650                 655

Pro Leu Pro Glu Asn Pro Cys Asp Phe Thr Gly Ser Glu Pro Met Thr
            660                 665                 670

Val Gly Glu Asn Gly Ser Thr Gly Ala Ile Cys His Asp Asp Val Ile
        675                 680                 685

Glu Ser Ile Asp Val Glu Val Ser Ser Gln Glu Ala Pro Ser Ser
    690                 695                 700

Ser Ser Lys Val Pro Thr Pro Leu Pro Ser Ile His Ser Ala Ser Pro
705                 710                 715                 720

Thr Leu Gly Phe Ala Met Met Ala Ser Leu Asp Ala Pro Gly Lys Val
                725                 730                 735

Gly Pro Ala Pro Phe Asn Leu Gln Arg Gln Gly Ser Arg Glu Asn Gly
            740                 745                 750

Ser Val Glu Ser Asp Gly Leu Thr Asn Asp Ser Ser Ser Leu Met Gly
        755                 760                 765

Asp Gln Glu Tyr Gln Ser Arg Ser Pro Asp Ile Leu Glu Thr Thr Ser
    770                 775                 780

Phe Gln Ala Leu Ser Pro Ala Asn Ser Gln Ala Glu Ser Ile Lys Ser
785                 790                 795                 800

Lys Ser Pro Asp Ala Gly Ser Lys Ala Glu Ser Ser Glu Asn Ser Arg
                805                 810                 815

Thr Glu Met Glu Gly Arg Ser Ser Leu Pro Ser Thr Phe Ile Arg Ala
            820                 825                 830

Pro Pro Thr Tyr Val Lys Val Glu Val Pro Gly Thr Phe Val Gly Pro
        835                 840                 845

Ser Thr Leu Ser Pro Gly Met Thr Pro Leu Leu Ala Ala Gln Pro Arg
    850                 855                 860

Arg Gln Ala Lys Gln His Gly Cys Thr Arg Cys Gly Lys Asn Phe Ser
865                 870                 875                 880

Ser Ala Ser Ala Leu Gln Ile His Glu Arg Thr His Thr Gly Glu Lys
                885                 890                 895

Pro Phe Val Cys Asn Ile Cys Gly Arg Ala Phe Thr Thr Lys Gly Asn
            900                 905                 910

Leu Lys Val His Tyr Met Thr His Gly Ala Asn Asn Ser Ala Arg
        915                 920                 925

Arg Gly Arg Lys Leu Ala Ile Glu Asn Thr Met Ala Leu Leu Gly Thr
    930                 935                 940

Asp Gly Lys Arg Val Ser Glu Ile Phe Pro Lys Glu Ile Leu Ala Pro
945                 950                 955                 960

Ser Val Asn Val Asp Pro Val Val Trp Asn Gln Tyr Thr Ser Met Leu
                965                 970                 975
```

```
Asn Gly Gly Leu Ala Val Lys Thr Asn Glu Ile Ser Val Ile Gln Ser
            980                 985                 990

Gly Gly Val Pro Thr Leu Pro Val Ser Leu Gly Ala Thr  Ser Val Val
        995                1000                1005

Asn Asn Ala Thr Val Ser Lys Met Asp Gly Ser Gln  Ser Gly Ile
    1010                1015                1020

Ser Ala Asp Val Glu Lys Pro Ser Ala Thr Asp Gly  Val Pro Lys
    1025                1030                1035

His Gln Phe Pro His Phe Leu Glu Glu Asn Lys Ile Ala Val Ser
    1040                1045                1050

<210> SEQ ID NO 12
<211> LENGTH: 616
<212> TYPE: PRT
<213> ORGANISM: Homo sapiens
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (141)..(141)
<223> OTHER INFORMATION: Xaa can be any naturally occurring amino acid
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
<222> LOCATION: (444)..(445)
<223> OTHER INFORMATION: Xaa can be any naturally occurring amino acid
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: misc_feature
<222> LOCATION: (602)..(602)
<223> OTHER INFORMATION: Xaa can be any naturally occurring amino acid
<220> FEATURE:
<221> NAME/KEY: misc_feature
<222> LOCATION: (613)..(613)
<223> OTHER INFORMATION: Xaa can be any naturally occurring amino acid

<400> SEQUENCE: 12

Met Ser Arg Arg Lys Gln Ala Lys Pro Gln His Ile Asn Ser Glu Glu
1               5                   10                  15

Asp Gln Gly Glu Gln Gln Pro Gln Gln Gln Thr Pro Glu Phe Ala Asp
                20                  25                  30

Ala Ala Pro Ala Ala Pro Ala Ala Gly Glu Leu Gly Ala Pro Val Asn
            35                  40                  45

His Pro Gly Asn Asp Glu Val Ala Ser Glu Asp Glu Ala Thr Val Lys
        50                  55                  60

Arg Leu Arg Arg Glu Glu Thr His Val Cys Glu Lys Cys Cys Ala Glu
65                  70                  75                  80

Phe Phe Ser Ile Ser Glu Phe Leu Glu His Lys Lys Asn Cys Thr Lys
                85                  90                  95

Asn Pro Pro Val Leu Ile Met Asn Asp Ser Glu Gly Pro Val Pro Ser
            100                 105                 110

Xaa Asp Phe Ser Gly Ala Val Leu Ser His Gln Pro Thr Ser Pro Gly
        115                 120                 125

Ser Glu Asp Cys His Arg Glu Asn Gly Gly Ser Ser Xaa Asp Ile Lys
    130                 135                 140

Glu Lys Pro Asp Ala Glu Ser Val Val Tyr Leu Lys Thr Glu Thr Ala
```

-continued

```
            145                 150                 155                 160
Leu Pro Pro Thr Pro Gln Asp Ile Ser Tyr Leu Ala Lys Gly Lys Val
                165                 170                 175

Ala Asn Thr Asn Val Thr Leu Gln Ala Leu Arg Gly Thr Lys Val Ala
                180                 185                 190

Val Asn Gln Arg Ser Ala Asp Ala Leu Pro Ala Pro Val Pro Gly Ala
                195                 200                 205

Asn Ser Ile Pro Trp Val Leu Glu Gln Ile Leu Cys Leu Gln Gln Gln
            210                 215                 220

Gln Leu Gln Gln Ile Gln Leu Thr Glu Gln Ile Arg Ile Gln Val Asn
225                 230                 235                 240

Met Trp Ala Ser His Ala Leu His Ser Ser Gly Ala Gly Ala Asp Thr
                245                 250                 255

Leu Lys Thr Leu Gly Ser His Met Ser Gln Gln Val Ser Ala Ala Val
                260                 265                 270

Ala Leu Leu Ser Gln Lys Ala Gly Ser Gln Gly Leu Ser Leu Asp Ala
                275                 280                 285

Leu Lys Gln Ala Lys Leu Pro His Ala Asn Ile Pro Ser Ala Thr Ser
            290                 295                 300

Ser Leu Ser Pro Gly Leu Ala Pro Phe Thr Leu Lys Pro Asp Gly Thr
305                 310                 315                 320

Arg Val Leu Pro Asn Val Met Ser Arg Leu Pro Ser Ala Leu Leu Pro
                325                 330                 335

Gln Ala Pro Gly Ser Val Leu Phe Gln Ser Pro Phe Ser Thr Val Ala
                340                 345                 350

Leu Asp Thr Ser Lys Lys Gly Lys Gly Lys Pro Pro Asn Ile Ser Ala
                355                 360                 365

Val Asp Val Lys Pro Lys Asp Glu Ala Ala Leu Tyr Lys His Lys Cys
            370                 375                 380

Arg Ser Ser Leu Pro Ser Thr Phe Ile Arg Ala Pro Pro Thr Tyr Val
385                 390                 395                 400

Lys Val Glu Val Pro Gly Thr Phe Val Gly Pro Ser Thr Leu Ser Pro
                405                 410                 415

Gly Met Thr Pro Leu Leu Ala Ala Gln Pro Arg Gly Gln Ala Lys Gln
                420                 425                 430

His Gly Cys Thr Arg Cys Gly Lys Asn Xaa Ser Xaa Xaa Ser Ala Leu
                435                 440                 445

Gln Ile His Glu Arg Thr His Xaa Gly Glu Lys Pro Phe Val Cys Asn
            450                 455                 460

Ile Cys Gly Arg Ala Phe Thr Thr Lys Gly Asn Leu Lys Val His Tyr
465                 470                 475                 480

Met Thr His Gly Ala Asn Asn Ser Ala Arg Arg Gly Arg Lys Leu
                485                 490                 495

Ala Ile Glu Asn Thr Met Ala Leu Leu Gly Thr Asp Gly Lys Arg Val
            500                 505                 510

Ser Glu Ile Phe Pro Lys Glu Ile Leu Ala Pro Ser Val Asn Val Asp
            515                 520                 525

Pro Val Val Trp Asn Gln Tyr Thr Ser Met Leu Asn Gly Gly Leu Ala
            530                 535                 540

Val Lys Thr Asn Glu Ile Ser Val Ile Gln Ser Gly Gly Val Pro Thr
545                 550                 555                 560

Leu Pro Val Ser Leu Gly Ala Thr Ser Val Val Asn Asn Ala Thr Val
                565                 570                 575
```

```
Ser Lys Met Asp Gly Ser Gln Ser Gly Ile Ser Ala Asp Val Glu Lys
            580                 585                 590

Pro Ser Ala Thr Asp Gly Val Pro Lys Xaa Gln Phe Pro His Phe Leu
        595                 600                 605

Glu Glu Asn Lys Xaa Ala Val Ser
        610             615
```

METHOD FOR EXPANSION OF STEM CELLS AND THE USE OF SUCH CELLS This application is a §371 national state of PCT International Application No. PCT/US52011/048819, filed Aug. 23, 2011, claiming the benefit of U.S. Provisional Application No. 61/376,122, filed Aug. 23, 2010, the contents of each of which are hereby incorporated by reference in their entirety.

This invention was made with government support under grant number HL087984 awarded by the National Institute of Health. The government has certain rights in the invention.

Throughout this application, various publications are referred to by arabic numerals in parentheses. Full citations for these publications are presented in a References section immediately before the claims. Disclosures of the publications cited in the References section in their entireties are hereby incorporated by reference into this application in order to more fully describe the state of the art as of the date of the methods and apparatuses described herein.

FIELD OF THE INVENTION

The present invention relates to ex vivo expansion of a stem cell population using a polypeptide having the expansion enhancement activity of a Sal-like (SALL) polypeptide and the use of such cells.

BACKGROUND OF THE INVENTION

Stem cells have the potential to develop into many different cell types in the body during early life and growth. Stem cells can be divided into two broad categories: embryonic and adult. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin, or intestinal tissues. Adult stem cells can differentiate into multiple pathways. Mesenchymal stem cells are adult stem cells which give rise to a variety of cell types: bone cells (osteocytes), cartilage cells (chondrocytes), fat cells (adipocytes), and other kinds of connective tissue cells such as those in tendons. Neural stem cells are adult stem cells in the brain which give rise to its three major cell types: nerve cells (neurons) and two categories of non-neuronal cells—astrocytes and oligodendrocytes. Epithelial stem cells are adult stem cells in the lining of the digestive tract occur in deep crypts and give rise to several cell types: absorptive cells, goblet cells, paneth cells, and enteroendocrine cells. Skin stem cells are adult stem cells which occur in the basal layer of the epidermis and at the base of hair follicles. The epidermal stem cells are adult stem cells which give rise to keratinocytes, which migrate to the surface of the skin and form a protective layer. The follicular stem cells can give rise to both the hair follicle and to the epidermis.

Hematopoietic stem cells (HSCs) are rare adult stem cells that have been identified in fetal bone marrow, fetal liver, umbilical cord blood, adult bone marrow, and peripheral blood, which are capable of differentiating into three cell lineages including myeloerythroid (red blood cells, granulocytes, monocytes), megakaryocyte (platelets) and lymphoid (T-cells, B-cells, and natural killer) cells. These HSCs are used in clinical transplantation protocols to treat a variety of diseases including malignant and non-malignant disorders. Expansion of HSCs has important clinical applications since the relative inability to expand hematopoietic stem cells ex vivo imposes major limitations on the current use of HSC transplantation. There is shortage of HSCs used for patient treatments related to bone marrow transplantation or genetic disorders. For allogenic bone marrow transplantation, only one third of all patients who would potentially benefit from an HSC transplant will find a suitable human leukocyte antigen (HLA)-matched related donor.

This is especially true in cases where the number of available stem cells is limiting. This includes cord blood-derived stem cells for transplantation into adults and infusion of multiple cord blood units. While these procedures are possibly effective in increasing the overall incidence of engraftment they have not overcome the problem of the slow pace of hematopoietic recovery. Delayed myeloid engraftment after umbilical cord blood transplantation (UCBT) is often associated with increased early transplant related morbidity and mortality. This remains the primary obstacle for the successful use of cord blood as an alternative source of stem cells for allogeneic transplantation and novel strategies are required to overcome this problem.

Bone marrow stem cells have been used to treat a variety of diseases: leukaemia, inflammation, immunology, inborn anomalies of the blood and immune system, aplastic anaemia, and haemoglobinopathies. However, it is difficult and time-consuming to find a matching donor. Only one in three patients will find a suitable donor and many patients die due to being unable to find a proper donor. In addition, finding a proper match is especially problematic for African-Americans, Hispanics, Native Americans and people of mixed ethnicity. Therefore, it is demanding to develop a process for growing hematopoetic stem cells, which may eliminate the need for human donors. Creating a cell bank containing different haplotype of marrow stem cells might enable cells from one donor to generate enough supply for more than 1,000 recipients.

Stem cells may also hold the key to the fight against HIV. Possible methods of manipulating blood cells to make them resistant to HIV infection, includes genetically altering receptors on stem cells that differentiate to T cells. The modified stem cells can then be expanded and introduced to patients with HIV.

At present the standard sources of HSCs are bone marrow and peripheral blood. To obtain marrow cells, donors must undergo multiple aspirations to collect several thousand milliliters of bone marrow, a procedure that is carried out under general anaesthesia. To collect HSCs from the peripheral blood, the donor must be treated with granulocyte colony-stimulating factor to increase the number of circulating HSCs. Both of these procedures entail some risk and significant cost.

An important newer source of HSCs is umbilical cord blood (UCB). Umbilical Cord blood has major advantages over other sources of HSCs, such as from bone marrow and mobilized peripheral blood. Not only is UCB readily available from many of the nearly 50 UCB banks across the U.S., it also shows increased tolerance for mismatches with the host major histocompatability complex (MHC).

In addition to relatively widespread availability, these HSCs have several useful properties, including their decreased ability to induce immunological reactivity. In many cases, use of UCB incurs significantly less graft-versus-host disease compared to other sources of HSCs.

Yet, while there are clear advantages associated with the use of UCB, there are key issues that constitute a critical barrier to expanded use of this source of hematopoietic stem cells. An obstacle to the successful use of umbilical cord blood as a source of stem cells for allogenic transplantation is delayed myeloid engraftment. This results in increased early transplant related morbidity and mortality following umbilical cord blood transfusion. Despite intensive and expensive supportive care, there is still >50% treatment-related mortality during the first 100 days post-transplant due to delayed immune system and platelet recovery which leaves patients vulnerable to opportunistic infections. Infusions of multiple cord blood units have been used as a possible approach to increase overall engraftment, but to date have not solved the problem of slow hematopoetic recovery.

Another barrier to expanded use of UBC is limited HSC numbers per cord at harvest. As cell dose has been shown to be a major determinant of engraftment and survival after UCB transplantation, low stem cell numbers represents the most significant barrier to successful UCB stem cell transplantation.

The ability to expand ex vivo, prior to transplantation, the stem cell components of a single cord blood unit will greatly increase the viability of this treatment modality. Infusing patients with larger numbers of stem cells as opposed the limited cells available in an unexpanded cord blood unit, should greatly increase the likelihood of successful engraftment.

The expansion of non-hematopoietic adult stem cells, including stem cells isolated from organs such as brain, heart, liver, pancreas, kidney, lung, etc., has important clinical applications, particularly as an external source of cells for replenishing missing or damaged cells of tissues or organs.

Moreover, stem cell gene therapy for hematologic genetic disorders is constrained by the inefficiency of gene transfer into early hematopoietic progenitors and stem cells. The barrier that needs to be overcome is to expand the population of genetically modified cells so that sufficient modified cells can be obtained before applied to humans. For instance, children with severe sickle cell disease can be cured with bone marrow transplants. In the case of sick cell disease, one does not need to completely destroy the recipient bone marrow but merely to replace it with enough healthy or genetically corrected stem cells so as to produce sufficient quantities of healthy red blood cells.

Expansion of hematopoietic stem cells (HSCs) has remained an important goal to develop advanced cell therapies for bone marrow transplantation and many blood disorders. During the last two decades, since the first hematopoietic growth factors were identified, there have been numerous attempts to expand HSCs in vitro using purified growth factors that are known to regulate HSCs. However, these attempts have met with limited success. For example, the hematopoietic growth factors fetal liver tyrosine kinase (Flt3) ligand, stem cell factor, and interleukins 6 and 11 promoted self-renewal of murine hematopoietic stem cells. However, only a limited expansion of hematopoietic stem cells compared with fresh input cells was observed (1-3).

Although a number of pluripotent embryonic stem (ES) cell genes are identified, none have emerged as a robust factor for HSC expansion. They exhibit either a limited or no role in expansion of HSCs as reported in the literature. The best studies of pluripotent genes reported to date are OCT4 and Nanog and both are unable to induce expansion of HSCs. This conclusion is also supported by our studies that there is no significant effect on HSC expansion in the tissue culture with forced expression of these genes using a viral vector.

Activation of Notch-1 in cell intrinsic pathways has been studied as a possible means to increase expansion of HSCs, and the studies have shown that the activation of these pathways is able to maintain HSCs with lympho-myeloid repopulation potential. Overexpression of HOXB4 is the most effective method for stem cell expansion reported to date. Recently, Antonchuk et al. showed that retroviral overexpression of HOXB4 for 10 to 14 days in vitro could increase the number of repopulating HSCs by 40-fold compared with fresh bone marrow stem cells (4).

However, even 40-fold increase in repopulating HSCs is not sufficient for a variety of purposes.

SUMMARY OF THE INVENTION

The present invention discloses a method for expanding a stem cell population using Sal-like (SALL) polypeptide.

The Sal-like (SALL) family (also called Hsal), comprised of SALL1 transcript variant 1 (SEQ ID No:1 [NCBI Reference Sequence: NM002968.2]), SALL1 transcript variant 2 (SEQ ID No:2 [NCBI Reference Sequence: NM001127892.1]), SALL2 (SEQ ID No:3 [NCBI Reference Sequence: NM_005407.1]), SALL3 (SEQ ID No:4 [NCBI Reference Sequence: NM_171999.2]), SALL4a (SEQ ID No:5 [GenBank: AY172738.1]), and SALL 4b (SEQ ID No:6 [GenBank: AY170621.1]), was originally cloned based on a DNA sequence homology to the *Drosophila* gene sal. In a related aspect, nucleic acid sequences comprising the sequences set forth as SEQ ID Nos: 1, 2, 3, 4, 5, and 6 encode amino acids in the sequences set forth as SEQ ID Nos: 7, 8, 9, 10, 11, and 12, respectively.

In humans, members of the SALL family, including SALL4, play an important role in normal development. Parallel to its important role in development, the SALL gene family has been found to be expressed in human and murine ES cells and during early development. SALL4 is expressed in the 2-cell stage of the embryo, similar to OCT4, while expression of SOX2 and NANOG begins in the blastocystic stage of embryonic development (1-3). Our group and others have shown that the embryonic stem cell (ESC) factor, SALL4, plays a vital role in maintaining ES cell pluripotency and in governing decisions affecting the fate of ES cells through transcriptional modulation of Oct4 and Nanog (4, 6, 8-10). We and others have also shown that SALL4 can activate OCT4 and interact with Nanog (9-11), and the SALL4/OCT4/Nanog transcriptional core network is essential for the maintenance of "stemness" of ES cells. By 10.5 days post-coitum, SALL4 is detectable mainly in the stem/progenitor populations in various organ systems including the brain and bone marrow of the embryo and later in the adult. This may suggest that SALL4 is not only involved in ESCs but also in adult stem cells (12-14).

This invention provides a method for expanding a stem cell population ex vivo, the method comprising providing to the stem cell population a polypeptide having the expansion enhancement activity of a Sal-like (SALL) polypeptide in an amount effective to expand the stem cell population ex vivo.

This invention further provides a composition for enhancing the expansion of a stem cell population in a subject, the composition comprising SALL polypeptide in an effective amount for the expansion of the stem cell population, and a culture media.

This invention further provides a method for identifying an agent for the expansion of a stem cell population, the method comprising (a) obtaining a candidate agent; (b) exposing a stem cell from the population to the candidate agent and (c) determining whether a SALL polypeptide is up-regulated in the stem cell, wherein if SALL polypeptide is up-regulated, then the agent is determined to be an agent for the expansion of the stem cell population.

This invention further provides a method for treatment or prophylaxis of diseases, disorders, or abnormalities in a subject requiring a stem cell or an expanded stem cell derived therefrom, the method comprising a) obtaining a stem cell population, b) providing to the stem cell population a SALL polypeptide in an amount effective to expand the stem cell population, and c) transplanting the expanded stem cell population to the subject in an amount effective for the treatment or prophylaxis of the diseases, disorders, or abnormalities of the subject.

This invention further provides a stem cell bank, comprising genetically distinct stem cell populations, wherein the stem cell populations have been expanded according to methods of the claims.

DETAILED DESCRIPTION OF THE INVENTION

Exemplary Embodiments of the Invention

Figure 1:
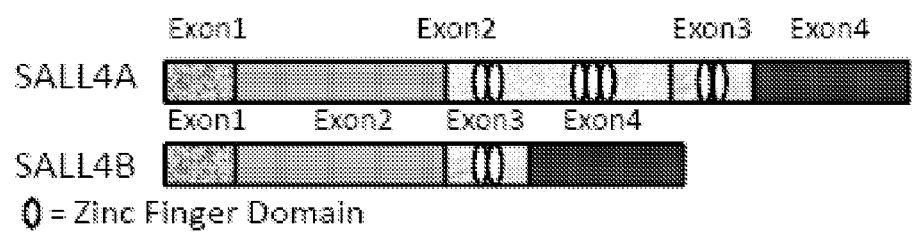
FIG. 1. Schematic diagram of the SALL4A and SALL4β isoforms demonstrating the variable number of zinc finger domains possessed by each. The HSCs were transduced with either the SALL4A or SALL4B gene using a lentiviral transfection system.

This invention provides a method for expanding a stem cell population, the method comprising providing to the stem cell population a polypeptide having the expansion enhancement activity of a Sal-like (SALL) polypeptide in an amount effective to expand the stem cell population.

In one embodiment, the stem cell is an adult stem cell.

In some embodiments, the stem cell is in or derived from the brain, liver, heart, kidney, skin, pancreas, bladder, gall bladder, large intestine, small intestine, stomach, skeletal muscle, or lung.

In another embodiment, the stem cell is a hematopoietic stem cell.

In yet another embodiment, the hematopoietic stem cell is in or derived from umbilical cord blood, peripheral blood, bone marrow, or spleen. In yet another embodiment, the hematopoietic stem cell is a human stem cell.

In some embodiments, methods for expanding a stem cell population also comprise administration of a SALL polypeptide in combination with a stimulating factor. In some embodiments, the stimulating factor is G-SCF, GM-CSF, M-CSF, a stem cell factor, or FMS-like tyrosine kinase-3 (FLT-3).

In some embodiments, the stem cell population is expanded ex vivo.

In some embodiments, the stem cell population is expanded in vivo. In another embodiment, stem cell population is cultured in media comprising 50 ng/ml FMS-like tyrosine kinase-3 (FLT-3), 50 ng/ml Thrombopoietin (TPO), and/or 50 ng/ml Stem cell factor (SCF).

In another embodiment, the stem cell population is cultured in media comprising 25 ng/ml FMS-like tyrosine kinase-3 (FLT-3), 25 ng/ml Thrombopoietin (TPO), and/or 25 ng/ml Stem cell factor (SCF).

In one embodiment, the SALL polypeptide is attached to a transport moiety capable of crossing a cell membrane, thereby transporting the SALL polypeptide into the cell.

In another embodiment, the transport moiety is a HIV-1 transactivator of transcription (TAT) peptide, a Chariot protein, an arginine-rich peptide, an Antennapedia-derived penetratin peptide, a herpes simplex virus type 1 VP22 protein, or a +36 GFP.

In another embodiment, SALL for use in the present invention may be in the form of a nucleic acid or a polypeptide.

In one embodiment, the SALL polypeptide comprises amino acids in the sequence set forth in SEQ ID No: 7, 8, 9, 10, 11 or 12.

In one embodiment, SALL polypeptide is encloded by nucleotide sequence comprising SEQ ID No: 1, 2, 3, 4, 5 or 6.

In another embodiment, the stem cell population is provided with SALL polypeptide comprising amino acids in the sequence set forth in SEQ ID No: 7, 8, 9, 10, 11 and/or 12.

In one embodiment, a cell in the population is transduced with a viral vector comprising nucleotides encoding the SALL polypeptide, thereby providing the SALL polypeptide to the stem cell population.

In another embodiment, the viral vector is derived from, but are not limited to, adenoviruses, baculoviruses, parvoviruses, herpesviruses, poxviruses, adeno-associated viruses, Semliki Forest viruses, vaccinia viruses, and retroviruses.

In one embodiment, the exogenous SALL gene is transiently expressed in the stem cell.

In another embodiment, nucleotides encoding the SALL polypeptide comprise sequence as set forth in SEQ ID No: 1, 2, 3, 4, 5 or 6.

In another embodiment, the nucleotides encoding the SALL polypeptide are expressed under the control of an inducible promoter.

In another embodiment, SALL polypeptide for use in the present invention may be exogenous or endogenous. Preferably, SALL polypeptide is exogenous. In the present invention, an exogenous SALL polypeptide is provided to a cell, thereby promoting the expansion of the cell. In this case, an endogenous SALL polypeptide may be supplemented with an exogenous SALL polypeptide to enhance the effect thereof.

In one embodiment, the stem cell population is expanded 10-fold, 20-fold, 50-fold, 100-fold, or 1000-fold.

This invention further provides a composition for enhancing the expansion of a stem cell population in a subject, the composition comprising SALL polypeptide in an effective amount for the expansion of the stem cell population, and a culture media. In one embodiment, the composition further comprises stem cells.

This invention further provides a method for identifying an agent for the expansion of a stem cell population, the method comprising (a) obtaining a candidate agent; (b) exposing a stem cell from the population to the candidate agent and (c) determining whether a SALL polypeptide is up-regulated in the stem cell, wherein if SALL polypeptide is up-regulated, then the agent is determined to be an agent for the expansion of the stem cell population. In one embodiment, the candidate agent may be provided in a library. In another embodiment, the invention provides an agent for the expansion of a stem cell obtained by the above-described screening method.

This invention further provides a method for treatment or prophylaxis of diseases, disorders, or abnormalities in a subject requiring a stem cell or an expanded stem cell derived therefrom, the method comprising a) obtaining a stem cell population, b) providing to the stem cell population a SALL polypeptide in an amount effective to expand the stem cell population, and c) transplanting the expanded stem cell population to the subject in an amount effective for the treatment or prophylaxis of the diseases, disorders, or abnormalities of the subject.

In one embodiment, the present invention may target hematopoietic and circulatory (blood cells, etc.) diseases, disorders or abnormalities, including, but are not limited to, anemia (e.g., aplastic anemia (particularly, severe aplastic anemia), renal anemia, cancerous anemia, secondary anemia, refractory anemia, etc.), cancer or tumors (e.g., leukemia); and after chemotherapy therefor, hematopoietic failure, thrombocytopenia, acute myelocytic leukemia (particularly, a first remission (highrisk group), a second remission and thereafter), acute lymphocytic leukemia (particularly, a first remission, a second remission and thereafter), chronic myelocytic leukemia (particularly, chronic period, transmigration period), malignant lymphoma (particularly, a first remission (high-risk group), a second remission and thereafter), multiple myeloma (particularly, an early period after the onset), and the like. The present invention also targets heart failure, stenocardia, cardiac infarction, arrhythmia, valvular heart diseases, myocardial/pericardial diseases, congenital heart diseases (e.g., atrial septal defect, ventricular septal defect, arterial duct patency, tetralogy of Fallot), arterial diseases (e.g., arterial sclerosis, aneurysm, etc.), venous diseases (e.g., phlebeurysm, etc.), and lymph vessel diseases (e.g., lymphatic edema), sickle cell disease, and treatment of radiation induced injuries, autoimmune diseases, cerebral palsy, critical limb ischemia, degenerative joint disease, diabetes type 2, heart failure, multiple sclerosis, osteoarthritis, rheumatoid arthritis, and spinal injury.

The invention further provides a stem cell bank, comprising genetically distinct stem cell populations, wherein the stem cell populations have been expanded according to the methods of the subject invention.

This invention provides a method for expanding a stem cell population in a subject, comprising increasing the amount of SALL polypeptide in the subject.

This invention further provides a method for increasing the size of a progenitor cell population in a subject the method comprising the method comprising increasing the amount of SALL polypeptide in the subject.

In some embodiments, increasing the amount of SALL polypeptide in the subject comprises introducing into the subject the SALL polypeptide.

In some embodiments, increasing the amount of SALL polypeptide in the subject comprises introducing into the subject a nucleic acid molecule having nucleotides in a sequence encoding the SALL polypeptide.

In some embodiments, the nucleotides encoding the SALL polypeptide comprise nucleotides in the sequence as set forth as SEQ ID No: 1, 2, 3, 4, 5 or 6.

In some embodiments, the SALL polypeptide comprises a transport moiety capable of crossing a cell membrane, thereby transporting the SALL polypeptide into the cell.

In some embodiments, the protenitor cell is a hematopoeitic projenitor cell population.

Aspects of the invention also provide methods of enhancing the long-term engraftment of hematopoietic stem cells in a subject. In some embodiments, the hematopoietic stem cells are derived from a donor.

Non-limiting examples of diseases, disorders, or abnormalities in a subject requiring a stem cell or an expanded stem cell derived therefrom include but are not limited to severe aplastic anemia, leukopenia, neutropenia, acute radiation syndrome, multiple myeloma, non-Hodgkin's lymphoma, and Hodgkin's lymphoma. Methods of the present invention may be used in combination with various cancer treatment which are known to produce side effects such as a decrease in the number of white blood cells such as chemotherapy, radiation therapy, and bone marrow transplantation.

Each embodiment disclosed herein is contemplated as being applicable to each of the other disclosed embodiments. Thus, all combinations of the various elements described herein are within the scope of the invention.

It is understood that where a parameter range is provided, all integers within that range, and tenths thereof, are also provided by the invention. For example, "0.2-5 mg/kg/day" includes 0.2 mg/kg/day, 0.3 mg/kg/day, 0.4 mg/kg/day, 0.5 mg/kg/day, 0.6 mg/kg/day etc. up to 5.0 mg/kg/day.

Definitions

Stem cell as used herein refers to a cell having the ability to both self-renew indefinitely and differentiate to produce at least one functional, terminal cell type.

Progenitor cell as used herein refers to a cell having a limited ability to self-renew and which differentiates to produce at least one functional, terminal cell type.

Hematopoietic cells as used herein refer to cells normally found in the blood as well as cells that give rise to cells normally found in the blood, such as cells found in the bone marrow. In this context "normally" includes the situation where a person is treated to alter the number or quality oc cells in the blood of bone marrow.

Hematopoietic stem cells as used herein refers to multipotent stem cells that give rise to all blood cell types.

"Expanding" as used herein refers to increasing the number of stem cells by proliferation of the stem cells, as opposed to converting cells which are not stem cells into stem cells.

Sal-like (SALL) gene or polypeptide is used herein to comprise SALL1, SALL2, SALL3, and SALL4, which were originally cloned based on a DNA sequence homology to the *Drosophila* gene sal. SALL4 comprises SALL4a and SALL4b.

Viral vector is used herein to mean a vector that comprises all or parts of a viral genome which is capable of being introduced into cells and expressed. Such viral vectors may include native, mutant or recombinant viruses. Such viruses may have an RNA or DNA genome. Examples of suitable viral vectors include, but are not limited to, adenoviruses, baculoviruses, parvoviruses, herpesviruses, poxviruses, adeno-associated viruses, Semliki Forest viruses, vaccinia viruses, and retroviruses and hybrid vectors.

A "transport moiety" is used herein to mean a polypeptide that is capable of crossing a cell membrane and can transport a polypeptide of the present invention into a stem cell. Examples of transport moities include but are not limited to, HIV-1 transactivator of transcription (Tat) peptide, a Chariot™ protein, an arginine-rich peptide, an Antennapedia-derived penetratin peptide, a herpes simplex virus type 1 VP22 protein, and a +36 GFP. In embodiments in which a SALL polypeptide is attached to a transport moiety, "attached" can be covalently attached.

The term "amount effective" means the amount of the subject polypeptide or stem cell that will elicit the biological or medical response of a cell, tissue, system, animal or human that is being sought by the researcher, veterinarian, medical doctor or other clinician.

A "construct" is used to mean recombinant nucleic acid which may be a recombinant DNA or RNA molecule, that has been generated for the purpose of the expression of a specific nucleotide sequence(s), or is to be used in the construction of other recombinant nucleic acids. In general, "construct" is used herein to refer to an isolated, recombinant DNA or RNA molecule.

The term "capable of engraftment" is used in here to refer to the ability of a hematopoietic cell to implant into the bone marrow for an extended period of time, e.g. at least one year. Implantation may be detected directly, (e.g. by biopsy) or by the production of progeny cells in the blood.

Transduction is used to refer to the introduction of genetic material into a cell by using a viral vector. As used herein a transduced cell results from a transduction process and contains genetic material it did not contain before the transduction process, whether stably integrated or not.

The phrase "culture media" is used to mean any of the standard culture media for culturing stem cells.

"Nucleic acid sequence" as used herein refers to an oligonucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Stem Cells

Stem cells of the present invention (e.g., adult stem cells, and hematopoietic stem cells) include all those known in the art that have been identified in mammalian organs or tissues. Stem cells may include, but are not limited to pluripotent stem cells, mesenchymal stem cells, hematopoietic stem cells, myeloid stem cells, and lymphoid stem cells. The best characterized is the hematopoietic stem cell. The hematopoietic stem cell, isolated from bone marrow, blood, cord blood, fetal liver and yolk sac, is the progenitor cell that generates blood cells or following transplantation reinitiates multiple hematopoietic lineages and can reinitiate hematopoiesis for the life of a recipient. (See Fei, R., et al., U.S. Pat. No. 5,635,387; McGlave, et al., U.S. Pat. No. 5,460,964; Simmons, P., et al, U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al, U.S. Pat. No. 5,716,827; Hill, B., et al. 1996.) When transplanted into lethally irradiated animals or humans, hematopoietic stem cells can repopulate the erythroid, neutrophil-macrophage, megakaryocyte and lymphoid hematopoietic cell pool.

It is well known in the art that hematopoietic cells include multipotent stem cells (e.g., a lymphoid stem cell), and/or progenitor cells committed to specific hematopoietic lineages. The progenitor cells committed to specific hematopoietic lineages may be of T cell lineage, B cell lineage, dendritic cell lineage, Langerhans cell lineage and/or lymphoid tissue-specific macrophage cell lineage. Hematopoietic stem cell and progenitor cell lineages are discussed in Sieburg et al. 2006, Schroeder et al. 2010, Dykstra et al. 2007, and U.S. Pat. No. 7,994,114, the contents of which are incorporated herein by reference.

Hematopoietic stem cells can be obtained from blood products. A "blood product" as used in the present invention defines a product obtained from the body or an organ of the body containing cells of hematopoietic origin. Such sources include unfractionated bone marrow, umbilical cord, peripheral blood, liver, thymus, lymph and spleen. It will be apparent to those of ordinary skill in the art that all of the aforementioned crude or unfractionated blood products can be enriched for cells having "hematopoietic stem cell" characteristics in a number of ways. For example, the blood product can be depleted from the more differentiated progeny. The more mature, differentiated cells can be selected against, via cell surface molecules they express. Additionally, the blood product can be fractionated selecting for CD34+ cells. CD34+ cells are thought in the art to include a subpopulation of cells capable of self-renewal and pluripotentiality. Such selection can be accomplished using, for example, commercially available magnetic anti-CD34 beads (Dynal, Lake Success, N.Y.). Unfractionated blood products can be obtained directly from a donor or retrieved from cryopreservative storage.

Hematopoietic stem cells may be harvested or collected prior to expansion of the stem cell population ex vivo. "Harvesting" hematopoietic progenitor cells is defined as the dislodging or separation of cells from the matrix. This can be accomplished using a number of methods, such as enzymatic, non-enzymatic, centrifugal, electrical, or size-based methods, or preferably, by flushing the cells using media (e.g. media in which the cells are incubated). The cells can be further collected, separated, and further expanded using the subject invention and generating larger populations.

Methods for isolation of hematopoietic stem cells are well-known in the art, and typically involve subsequent purification techniques based on cell surface markers and functional characteristics. The hematopoietic stem and progenitor cells can be isolated from bone marrow, blood, cord blood, fetal liver and yolk sac, and give rise to multiple hematopoietic lineages and can reinitiate hematopoiesis for the life of a recipient. (See Fei, R., et al., U.S. Pat. No. 5,635,387; McGlave, et al., U.S. Pat. No. 5,460,964; Simmons, et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827; Hill, B., et al. 1996.) For example, for isolating hematopoietic stem and progenitor cells from peripheral blood, blood in PBS is loaded into a tube of Ficoll (Ficoll-Paque, Amersham) and centrifuged at 1500 rpm for 25-30 minutes. After centrifuigation the white center ring is collected as containing hematopoietic stem cells.

Stem cells may be isolated from other tissues such as the brain, liver, heart, kidney, skin, and lung.

Stem Cell Transplantation

Stem cell transplantation can be used as part of the treatment for blood disorders such as leukemia, certain types of lymphoma (including Hodgkin lymphoma), aplastic anemia, thalassemia, sickle cell anemia, and some congenital metabolic or immunodeficiency disorders (such as chronic granulomatous disease). Certain types of stem cells may also be used as transplants for those whose bone marrow was destroyed by the high doses of chemotherapy or radiation therapy used to treat some cancers.

Stem cells may be the subject's own cells (autologous transplantation) or those of a donor (allogeneic transplantation). When the subject's own stem cells are used, they may be collected before chemotherapy or radiation therapy, "in vivo collection", because these treatments may damage stem cells. They may be injected back into the body after the treatment, such as increasing or expanding "in vivo expansion" the quality of the cells being expanded.

Current methods for stem cell storage involve collection of stem cells from embryonic cord blood and the collection of stem cells from blood donations. The utility of these techniques are limited because of the small proportion of total number of stem cells in the peripheral blood and because only a limited amount of blood may be collected from a blood transfusion. An advantage of using stem cells from an adult is that the subject's own cells can be expanded in culture using the methods described in the present invention and then reintroduced into the subject. Thus, there is also an unmet need in collecting human stem cell population for long term cryogenic storage, for example in a stem cell bank, and for the eventual thawing of the cryopreserved cell population for the treatment of a disease by autologous transfer. Preservation of stem cells for cyrostorage is well known in the art. For example, see Culture of human stem cells (Wiley-Liss, 2007), and Cryopreservation and freeze-drying protocols (Humana Press, 2007). These documents are hereby incorporated by reference.

The expanded stem cell population of the present invention may be used to treat hematopoietic and circulatory (blood cells, etc.) diseases, disorders or abnormalities. Examples of the diseases, disorders or abnormalities include, but are not limited to, anemia (e.g., aplastic anemia (particularly, severe aplastic anemia), renal anemia, cancerous anemia, secondary anemia, refractory anemia, etc.), cancer or tumors (e.g., leukemia); and after chemotherapy therefor, hematopoietic failure, thrombocytopenia, acute myelocytic leukemia (particularly, a first remission (highrisk group), a second remission and thereafter), acute lymphocytic leukemia (particularly, a first remission, a second remission and thereafter), chronic myelocytic leukemia (particularly, chronic period, transmigration period), malignant lymphoma (particularly, a first remission (high-risk group), a second remission and thereafter), multiple myeloma (particularly, an early period after the onset), and the like. The present invention also targets heart failure, stenocardia, cardiac infarction, arrhythmia, valvular heart diseases, myocardial/pericardial diseases, congenital heart diseases (e.g., atrial septal defect, ventricular septal defect, arterial duct patency, tetralogy of Fallot), arterial diseases (e.g., arterial sclerosis, aneurysm, etc.), venous diseases (e.g., phlebeurysm, etc.), and lymph vessel diseases (e.g., lymphatic edema), sickle cell disease, and treatment of radiation induced injuries, autoimmune diseases, cerebral palsy, critical limb ischemia, degenerative joint disease, diabetes type 2, heart failure, multiple sclerosis, osteoarthritis, rheumatoid arthritis, and spinal injury.

Methods for stem cell transplantation for treatment of diseases, disorders or abnormalities in humans are well know in the art. For example, see Manual of Stem Cell and Bone Marrow Transplantation (Cambridge University Press, 2009), Stem cell transplantation: biology, processing, and therapy (Wiley-VCH, 2006), and Practical Hematopoietic Stem Cell Transplantation (Wiley-Blackwell, 2007). These documents are hereby incorporated by reference.

Stem Cell Engraftment

Bone marrow regeneration after transplant is a function of proper engraftment of transplanted cells. In preferred embodiments, engraftment of transplanted cells is long term engraftment of the cells. In some embodiments, the invention encompasses improved engraftment of hematopoietic stem cells (HSCs) derived from human umbilical cord blood. Embodiments of the present invention are useful for the treatment of various diseases such as marrow failure disorders, various genetic diseases, and hematopoietic malignancies.

In cases in which hematopoietic stem cells (HSCs) from a donor are transplanted into the host, embodiments of the invention are useful to increase the donor cells' chimerism with host cells. As used herein, chimerism is the coexistence of two genetically distinct types of cells in a single organism. Once chimerism has been established, the HSCs may proliferate within the host.

As disclosed herein intraperitoneally injected TAT-SALL4 protein dramatically stimulates chimerism and stem cell long-term engraftment. The SALL polypeptides described herein may be used to significantly increase survival, expansion and engraftment or chimerism of transplanted cells in the marrow or a niche in accordance with embodiments of the invention.

Aspects of the present invention relate to gene therapy, particularly as applied to hematopoietic stem cells and hematopoietic progenitor cells, to transduced cells and methods of obtaining them, and to methods of using them to provide prolonged engraftment of modified hematopoietic cells in subjects.

Polypeptides

The present invention emcompasses a polypeptide having the expansion enhancement activity of a Sal-like polypeptide. The term "a polypeptide having the expansion enhancement activity of a Sal-like polypeptide" refers to polypeptides exhibiting activity similar, but not necessarily identical to, an activity of a polypeptide of the invention as measured in a particular biological assay.

It will be appreciated by those skilled in the art that DNA sequence polymorphisms that lead to changes in the amino acid sequences of SALL may exist within a population (e.g., the human population). Such genetic polymorphism in the SALL gene may exist among individuals within a population due to natural allelic variation. As used herein, the terms "gene" and "recombinant gene" refer to nucleic acid molecules comprising an open reading frame encoding a SALL polypeptide, preferably a mammalian SALL polypeptide. Such natural allelic variations can typically result in 1-5% variance in the nucleotide sequence of the SALL gene. Any and all such nucleotide variations and resulting amino acid polymorphisms in SALL that are the result of natural allelic variation and that do not alter the functional activity of SALL are intended to be within the scope of the invention. The present invention encompasses nucleotide variations and resulting amino acid polymorphisms in SALL polypeptide which are substantially homologous to the SALL nucleotides disclosed herein.

To determine the percent homology of two amino acid sequences, or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (i.e., percent homology equals the number of identical positions/total number of positions times 100).

The present invention discloses experimental results of overexpressing SALL4a and SALL4b polypeptides in HSCs and demonstrates that overexpression of both of these polypeptides enhances the expansion of HSCs ex vivo. SALL4a and SALL4b are isomers of the SALL gene, and are 1053 and 616 amino acids long, respectively. However, even though SALL4b lacks over 400 amino acids present in SALL4a, it is nonetheless capable of enhancing the expansion of HSCs as disclosed herein to the level of SALL4a. Therefore, not all amino acids of SALL4a are required for the expansion enhancement activity of a Sal-like polypeptide. According to ALIGN Query (GENESTREAM SEARCH network server IGH Montpellier, France), the overall sequence identity among SALL4a and SALL4b is 57.5%. However, the sequence alignment of SALL4a and SALL4b polypeptides using the ExPASy (Expert Protein Analysis System) proteomics server reveals two domains in SALL4a that may be important for biological activity of these polypeptides in HSCs. Putative domain 1 of SALL4a and SALL4b includes the first 385 N-terminal amino acids of SALL4a and SALL4b, and reveals 98.7% sequence identity among the two polypeptides. Putative domain 2 includes C-terminal 822-1053 amino acids of SALL4a and C-terminal 385-616 amino acids of SALL4b, and reveals 97% sequence identity among the two polypeptides. Based on this information, it is possible to readily prepare additional peptides that have enhancement activity of SALL4a or SALL4b.

The invention also encompasses polypeptides having a lower degree of identity to a polypeptide having the expansion enhancement activity of a Sal-like polypeptide but having sufficient similarity so as to perform one or more of the same functions performed by the SALL polypeptides. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al. (1990) Science 247:1306-1310.

According to ALIGN Query, the overall sequence identity of each one of SALL1 transcript variant 1, SALL1 transcript variant 2, SALL2, and SALL3, with SALL4a is 38.1%, 37.1%, 28.1%, and 38.4%, respectively.

As used herein, a polypeptide (or a region of the polypeptide) is substantially homologous to a polypeptide having the expansion enhancement activity of a Sal-like polypeptide when the amino acid sequences are at least about 25-30%, 30-35%, 35%-40% 40-45%, 45-50%, 50-55%, 55-60%, typically at least about 70-75%, more typically at least about 80-85%, and most typically at least about 90-95% or more homologous. A substantially homologous amino acid sequence, according to the present invention, will be encoded by a nucleic acid sequence hybridizing to the nucleic acid sequence, or portion thereof, of the sequence shown in SEQ ID NO: 1, 2, 3, 4, 5, and/or 6 under stringent conditions.

The invention further encompasses nucleic acid molecules that differ from the disclosed nucleotide sequences encoding the SALL polypeptide due to degeneracy of the genetic code. These nucleic acids therefore encode the same Sal-like polypeptide as those encoded by the nucleotide sequence shown in SEQ ID NO: 1, 2, 3, 4, 5, and/6.

A nucleic acid fragment encoding "a polypeptide having the expansion enhancement activity of a Sal-like polypeptide" can be prepared by isolating a portion of SEQ ID NO: 1, 2, 3, 4, 5, and/or 6, that encodes a polypeptide having a Sal-like polypeptide biological activity, expressing the encoded portion of Sal-like polypeptide (e.g., by recombinant expression ex vivo), and assessing the activity of the encoded portion of Sal-like polypeptide.

Increasing the Amount of a SALL Polypeptide in a Subject

The amount of a SALL polypeptide may be increased in a subject by a variety of means, including agents that increase the expression of the SALL polypeptide, administration of the SALL polypeptide, and introducing into the subject nucleotides encoding the SALL peptide.

Agents that may be used increase the expression of a SALL peptide include but are not limited to peptides, peptide-mimetics, oligonucleotides, small molecule compounds, and RNA interference inducing molecules.

Administration of a SALL polypeptide to a subject may be nasal, pulmonary, parenteral, i.v., i.p., intra-articular, transdermal, intradermal, s.c., topical, intramuscular, rectal, intrathecal, intraocular, and buccal all using dosage forms well known to those of ordinary skill in the pharmaceutical arts. Preferred routes of administration for SALL polypeptides include i.v. and i.p.

A SALL polypeptide can be administered in admixture with suitable pharmaceutical diluents or carriers (collectively referred to herein as a pharmaceutically acceptable carrier) suitably selected with respect to the intended form of administration and as consistent with conventional pharmaceutical practices. The unit may be in a form suitable for topical, intravenous or direct injection or parenteral administration.

General techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976);

Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

The present invention also provides for increasing the amount of a SALL polypeptide in a subject by introducing into the subject nucleotides encoding the SALL polypeptide. In some embodiments, the nucleotides encoding the SALL polypeptide comprise nucleotides in the sequence as set forth as SEQ ID No: 1, 2, 3, 4, 5 or 6. The nucleotides encoding the SALL polypeptide may be operably linked to an expression regulatory sequence such as a promoter, and may be introduced into the subject through the use of a suitable vector as described hereinbelow.

Vectors

Different types of vectors can be used for transduction or transformation of stem cells. These include plasmid or viral vectors. Retroviral vectors have been used widely so far in gene therapy, particularly those based on Moloney murine leukemia virus (MoMLV). Vectors based on murine retroviruses can be used for high efficiency transduction of cells, however, they require that the cells be active in cell division. Transduction of HP cells with murine retroviral based vectors therefore requires activation of the cells.

Lentiviral vectors, a subclass of the retroviral vectors, can also be used for high-efficiency transduction (Haas et al 2000, Miyoshi et al 1999, Case et al 1999) and are able to transduce non-dividing cells, not needing the induction of HP cells into cell cycle. This would avoid the loss of pluripotency that cell-cycle induction might cause in some of the cells. Other groups of retroviruses such as spumaviruses, for example the foamy viruses (Vassilopoulos et al 2001) are also capable of efficiently transducing non-dividing cells.

Other types of viral vectors that can be used in the invention include adenoviral vectors (Fan et al 2000, Knaan-Shanzer et al 2001, Marini et al 2000), adeno-associated viral (AAV) vectors (Fisher-Adams et al 1996), SV40 based vectors (Strayer et al 2000), or forms of hybrid vectors (for example Feng et al, 1997). Adenoviral vectors can be readily produced at high titers and can transduce non-dividing cells.

AAV vectors are non-pathogenic, transduce both proliferating and non-proliferating cells including CD34+ cells, and integrate stably into the cellular genome (Grimm and Kleinschmidt 1999). Moreover, they do not induce a host immune response and can be produced in helper-free systems. AAV vectors can effectively transduce CD34+ cells in long-term cultures (Chaterjee et al 1999).

Integrating vectors, such as retrovirus or lentivirus, are often used for gene therapy, however, random integration of these vectors, together with the oncogenic nature of some of the inducing genes, pose a risk of cancer formation. For this reason, non-integrating methods, such as adenovirus, baculovirus, or transient transfection of plasmids capable of episomal expression, are preferred. Vectors which result in non-integration of the introduced gene into the cell genome are preferred. Viral vectors which allow transient expression of the introduced gene are also preferred. Vector which have a short life-cycle in the host cell are also preferred.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (UPRT), dihydrofolate reductase (DHFR) (Scharf mann et al., 1991, Proc. Natl. Acad. Sci. USA, 88:4626-4630), adenosine deaminase, phospho glycerol kinase (PGK), pyruvate kinase, phospho glycerol mutase, the actin promoter (Lai et al., 1989, Proc. Natl. Acad. Sci. USA, 86:10006-10010), and other constitutive promoters known to those of skill in the art. In addition, many viral promoters function constitutively in stem cells. These include: the early and late promoters of SV40; the long terminal repeats (LTRS) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of an agent in the genetically modified cell. Selection and optimization of these factors for expression of a gene insert is deemed to be within the scope of one of ordinary skill in the art without undue experimentation, taking into account the above-disclosed factors.

Method of producing and using viral vectors for gene therapy are well known in the art. For example, see Gene transfer: delivery and expression of DNA and RNA: a laboratory manual (CSHL Press, 2007), Viral vectors for gene therapy: methods and protocols (Humana Press, 2003), Gene Therapy Protocols: Volume 2: Design and Characterization of Gene Transfer Vectors (Humana Press, 2008), and Gene and cell therapy: therapeutic mechanisms and strategies (CRC Press, 2008). These documents are hereby incorporated by reference.

Protein Transduction

Protein transduction may be used as an alternative to viral vectors for the delivery of proteins into stem cells. Protein tranduction is the internalisation of proteins into the cell, from the external environment. This process relies on the inherent property of a small number of proteins and peptides of being able to penetrate the cell membrane. The transducing property of these molecules can be conferred upon proteins which are expressed as fusions with them. Examples of peptides that can be used for protein transduction of the polypeptides on the subject invention include the following:

Antennapedia Peptide: The antennapedia motif is derived from a family of *Drosophila* homeoproteins, a class of transactivating factors involved in the developmental process. These proteins recognise and bind DNA through a 60 amino acid carboxy-terminal region arranged in three-helical sequences, called the homeodomain. The homeodomain of antennapedia (AntpHD) is capable of translocating across neuronal membranes and is conveyed to the nucleus.

Herpes Simplex Virus VP22 Protein: The herpes simplex virus type 1 (HSV-1) VP22 protein is a structural polypeptide forming the major component of the virus tegument situated between the envelope and capsid regions of the mature virion. It is a small basic protein, approximately 38 kDa in size, encoded by the UL49 gene.

HIV TAT Protein Transduction Domain: The HIV-1 transactivator gene product, TAT, has been shown to be a regulator of transcription in latent HIV and is essential for HIV replication. It is an 86 amino acid protein made from two exons of 72 and 14 amino acids, respectively.

Chariot Protein: Chariot is a 2843 dalton peptide and forms a non-covalent complex with the protein of interest (Active Motif, inc.).

Other examples of peptides that can be used for protein transduction include arginine-rich peptides (15), and +36 GFP (16).

Method of preparing peptides for protein transduction are well known in the art. For example, see Cell-penetrating peptides: Handbook of (CRC Press, 2006), Cell-penetrating peptides: processes and applications (CRC Press, 2002), Protein transduction: delivery of recombinant Tat-PTD fusion proteins into target cells (University of Tromsø, Institute of Medical Biology, 2000), and Protein analysis and purification: benchtop techniques (Springer, 2005). These documents are hereby incorporated by reference.

This invention will be better understood by reference to the Experimental Details which follow, but those skilled in the art will readily appreciate that the specific experiments detailed are only illustrative of the invention as described more fully in the claims which follow thereafter.

Methods

Isolation and SALL4-lentiviral Infection of Human cd34+ Cells

Normal human bone marrow CDd34+ cells were purchased (AllCells, Emeryville, Calif., USA) and single cell suspensions were generated in StemSpan SFEM (Stemcell Technologies, Vancouver, BC, Canada) for 24 hours. Next, $10^5$ cells/well were plated in a 12-well plate. The cells were cultured in StemSpan SFEM containing 10% FBS and 1% pen/strep (Gibco, Carlsbad, Calif., USA). Additionally, the media was supplemented with 100 ng/ml FLT-3, 100 ng/ml TPO and 100 ng/ml SCF (ProSpec, Rehovet, Israel). SALL4 lentivirus particles at an MOI between 10-20 were added to the bone marrow cells at 37° C. For controls, GFP-only lentivirus particles were added to the bone marrow cells at similar MOIs. The cells were infected for 2.5 hours and recovered in culture medium for 24 hours. The next day the cells were once again infected for 2.5 hours, rinsed, and plated for experimental expansion.

Expansion of SALL4-transduced Human CD34+ Cells

The SALL4-transduced CD34+ cells were expanded in 12-well plates under normal culture conditions (StemSpan SFEM containing 10% FBS and 1% pen/strep supplemented with 100 ng/ml FLT-3, 100 ng/ml TPO and 100 ng/ml SCF). In addition, cells were cultured in more stringent conditions in which recombinant cytokine concentrations were decreased to see if the SALL4-transduced cells were still capable of surviving and expanding. In one experiment, cells were cultured in media containing 50% less cytokines (50 ng/ml FLT-3, 50 ng/ml TPO and 50 ng/ml SCF). In an additional trial, cells were cultured in media containing 75% less growth factors (25 ng/ml FLT-3, 25 ng/ml TPO and 25 ng/ml SCF). Cells were monitored for two months and observed with brightfield and fluorescent microscopy.

Expansion of SALL4-transduced Isolated CD34+ Cells from Patient Samples Peripheral blood stem cells were obtained from the Blood Marrow Stem Cell Laboratory at Stony Brook, N.Y., USA. CD34+ cells were isolated from the stem cell pool using the CD34 human Microbead kit and Mini-MACS separation columns (Miltenyi Biotec Inc., Auburn, Calif., USA). After the CD34+ cells were isolated, the cells were transfected with lentivirus and cultured in the same manner as mentioned earlier.

CFU Assay of Bone Marrow Cells

Tubes of MethoCult® (StemCell Technologies, Vancouver, BC, Canada) medium were thawed overnight in a 4° refrigerator. The next morning tubes were vortexed to ensure all components were thoroughly mixed. SALL4-transduced or GFP-transduced CD34+ cells were then prepared at 10× the final concentration required. Cell suspensions of $1\times10^6$ cells per mL were prepared and duplicated the concentrations with different concentrations (2-4 folds). 0.3 mL of cells were added to 3 mL of MethoCult® medium (STEMCELL Technologies Inc, Vancouver, BC, Canada) for duplicate cultures. Tubes were once again vortexed to ensure all cells and components were thoroughly mixed and allowed to stand for 5 minutes for bubbles to dissipate. A 16 gauge blunt-end needle attached to a 3 cc syringe was used to dispense the cells and MethoCult® medium into culture dishes. 1.1 mL of cells were dispensed per 35 mm dish. The methylcellulose medium and cells were distributed evenly by gently tilting and rotating each dish. The two dishes were placed into a 100 mm petri dish and a third, uncovered 35 mm dish containing 3 mL of sterile water was also added. All 3 dishes were then covered within the 100 mm petri dish. The cells were incubated for 14-16 days at 37° C. with 5% $CO_2$ and 95% humidity. The BFU-E, CFU-GM and CFU-GEMM colonies were observed with brightfield and fluorescent microscopy. In addition, CFUs were counted under the microscope 10-18 days after the cells were plated in MethoCult® medium. A colony with more than 100 cells was counted as a positive colony.

Flow Cytometry and Phenotyping of Cells

FLOW was conducted with Phycoerythrin (PE)-conjugated antibody to CD34, allophycocyanin (APC)-conjugated antibody to CD38, and PerCP-Cy5.5-conjugated antibody to CD45 were used for cell sorting (BD Biosciences, Franklin Lakes, N.J., USA). The presence of human cells in NOD-SCID mouse bone marrow was determined using CD45-PE antibody. Myeloid cells were tracked by CD15-APC or CD33-APC antibody and lymphoid cells were tracked by CD19-PE or CD3-PE antibody.

Cell Counting and Growth Curve Experiments

SALL4A-transduced, SALL4B-transduced, and control cells were counted every 24 hours for seven days using a hemocytometer. Before counting, cells were gently aspirated with a 200 ml pipet tip in order to dissociate cell clusters into individual cells.

Long-Term Culture Assays

LTC-IC assays using human CD34+ cells were conducted under bulk or limiting dilution conditions in MethoCult® media. In order to calculate the total LTC-IC number, the frequency of LTC-ICs was determined from secondary cultures. This calculated number was then multiplied by the total number of cells present after 4-week primary long-term cultures.

NOD/SCID Mice Repopulating Cells (SRCs) Assays $4 \times 10^3$, $8 \times 10^3$, $2 \times 10^4$, or $4 \times 10^4$ 2-day old GFP-only or 14-day old cultured SALL4A or SALL4B expressing human CD34+ bone marrow cells along with $2 \times 10^5$ CD34− accessory cells were injected into irradiated (2,5 Gy) NOD-LtSz-scid/scid (NOD-SCID) mice on day 0. Seven weeks after transplantation, peripheral blood samples were analyzed by flow cytometry for the presence of CD45+ cells. Mice were scored as positive for human engraftment when at least 0.5% CD45+ human cells were detected among mouse peripheral blood cells. Stem cell initiating cell frequency was determined by the reciprocal of the concentration of test cells that gave 37% negative mice. Animal experiments were performed according to the investigator's protocols approved by the Stony Brook University Institutional Animal Care and Use Committee (IACUC).

Serially Transplanted Studies

Mice BM cells were harvested from the tibiae and femurs of highly engrafted primary recipient mice 16 weeks post-transplantation. After removal of red blood cells by lysis buffer, half of the BM cells from each recipient mouse was transplanted into one secondary sub-lethally irradiated (2.5 Gy) NOD/SCID mouse. Five weeks after transplantation, the percentage of human CD45+ cells in peripheral blood of the secondary recipient mouse was analyzed by flow cytometry as described. Tertiary transplants were conducted in the same manner and flow cytometry was conducted on bone marrow cells to analyze CD45+, CD33+, CD19+, and CD3+ cells 10-weeks post transplantation.

Expression and Purification of His-TAT-SALL4A/B

For expression of TAT-SALL4 in *E. coli*, the human SALL4B gene was doubly digested with the restriction endonucleases SalI and NotI, and ligated into a pTAT-pET28b vector, a 6xHis-taq protein expression vector bearing the T7 promoter, kanamycin resistance and pTAT Peptide/Protein Transducing Domain (PTD). The plasmids with the correct gene sequences were then transformed into *E. coli* strain BL21 (DE3). The 6xHis-fused human SALL4B was expressed with 0.1 mM IPTG induction for 3 h and then purified by using a Ni-NTA affinity column (Qiagen, Valencia, Calif., USA). The purity of the purified His-TAT-SALL4B was further determined based on SDS-PAGE and LC-MS/MS.

SDS-PAGE and Western Blot

Proteins were loaded on 12.5% one-dimensional SDS-PAGE for protein separation, followed by staining with Coomassie brilliant blue R-250 and destained in 10% methanol/7% acetic acid. For Western blot analysis, the SDS-PAGE was transferred to poly-(vinylidene difluoride) (PVDF) membranes (Millipore, Billerica, Mass., USA). After transfer, the membranes were saturated with 5% w/v nonfat dry milk in TBS/0.1% Tween 20 at 4° C. overnight, followed by incubation with the primary antibodies overnight at 4° C. Primary antibodies against human SALL4 and 6xHis-tag were purchased from Abcam (Cambridge, UK). After three washes with TBS/0.1% Tween 20, the membranes were incubated with a solution of peroxidase-conjugated secondary antibodies (Abcam, Cambridge, UK). After 1-h incubation at room temperature, the membranes were washed three times with TBS/0.1% Tween 20 and the membrane blots were developed by using ECL substrates (Millipore).

In-Gel Digestion and LC-MS/MS

Gel bands were cut and digested in-gel with trypsin. Peptides were resuspended in 50 μl 0.1% formic acid/2% acetonitrile. 10 μl of the peptide was injected into Orbitrap at the Stony Brook University Proteomics Center for 1D LC/MS/MS analysis.

Growth and Maintenance of Insect Cells

Sf9 insect cells were grown in Sf900-II SFM (Gibco) media supplemented with 10% FBS (Gibco) and 1% antibiotic/antimycotic (Cellgro). Media was filtered through ExpressPLUS 0.22 uM filtration unit (Millipore) before use. Cells were maintained at counts between 0.5 and $5.0 \times 10^6$ cells per mL, at 27° C. in either spinner flasks (Wheaton) or tissue culture shaker flasks (Fisher, Pittsburgh, Pa., USA).

Infection of Sf9 Cells with Baculovirus Containing His-TAT SALL4B Construct

Cells reaching a count of $2.5 \times 10^6$ cells per mL were infected with baculovirus containing the His-TAT SALL4B cDNA, which had been freshly amplified in Sf9 cells. Final volume was 100 mL in a Wheaton 250 mL spinner flask. Infected cells continued to incubate at 27° C. for 4 days before harvesting.

Lysis of Sf9 Cells, and his-TAT hSALL4B Purification

Cells were centrifuged at 500×g for 10 minutes. The supernatant was saved as virus stock. The cell pellet was resuspended in 20 mL lysis buffer containing 50 mM NaH2PO4 (pH 8.0), 0.3 M NaCl, protease inhibitor cocktail, PMSF, and 1% NP40 (IGEPAL). Following a 30 minute incubation on ice, the lysate was cleared by centrifugation at 10,000 g for 15 minutes at 4°.

Cleared lysate was added to Ni-NTA beads (Qiagen) washed 4 times with lysis buffer. 200 uL of beads were added for every 4 mL of lysate. To limit nonspecific binding, 10 mM imidazole was added. The solution was incubated on a rotator at 4o for up to 2 hours, then loaded onto a gravity flow column, and the flowthrough was collected. The beads were washed first with 10 mL lysis buffer with 20 mM imidazole, then with 10 mL lysis buffer with 80 mM imidazole. Elution was performed with lysis buffer and 250 mM imidazole, collected in 1.5 mL fractions, up to 10 mL. All lysates and fractions were analyzed by 8% PAGE-SDS and immunoblotting using a 1:2000 dilution of anti-SALL4 (Abnova). His-TAT SALL4B typically eluted in fractions 2 and 3. These were pooled and dialyzed overnight against PBS—in Slide-A-Lyzer cassettes (Pierce, Rockford, Ill., USA), and protein concentration was determined (BioRad, Hercules, Calif., USA).

Statistical Analysis

Results are reported as means±s.d. Values with $p < 0.05$ were considered to be statistically significant.

EXPERIMENTAL DETAILS

Example 1

Ex Vivo Expansion of SALL4-overexpressing Human HSC

To gain insight into the magnitude of SALL4-induced HSC expansion, the effects of SALL4 overexpression in human bone marrow CD34 positive cells following lentiviral transduction was investigated. The SALL4A and SALL4B cDNAs were incorporated into a vector carrying the GFP reporter gene that facilitated isolation and tracking of transduced cells. SALL4A and B are two splicing isoforms generated through internal splicing (FIG. 1).

Figure 2:
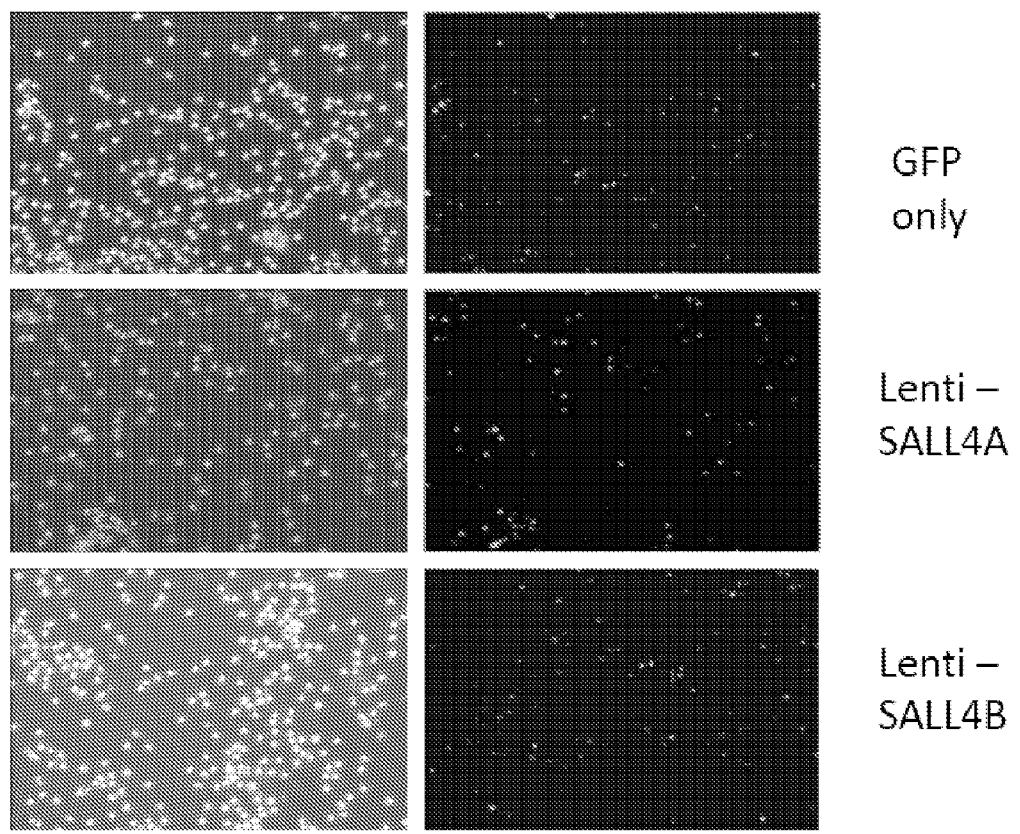
FIG. 2. Bright field and fluorescent images of human bone marrow CD34+ cells. Bright field (left) and fluorescent (right) images illustrating the infection efficiency of lentiviral constructs containing GFP+SALL4A, GFP+SALL4B, and GFP only. Images were taken 48 hours post infection with lentiviruses.

Normal human CD34+ cells were cultured for 2 days with growth media containing h-FLT-3, h-SCF, and h-TPO. After 48 hours, the cells were divided into six groups of $3 \times 10^4$ cells and placed into separate wells of a 12-well plate. The cells were then transduced with either a SALL4A, SALL4B, or GFP (control) human lentivirus for 2.5 hours. After two hours, the cells were allowed to recover in growth media. 24 hrs later, the cells were once again transduced with the aforementioned lentiviruses for 2.5 hours. The next day, the cells were observed for GFP positive cells. It was noted that approximately 40% of the cells were fluorescent (FIG. 2).

Figure 3:
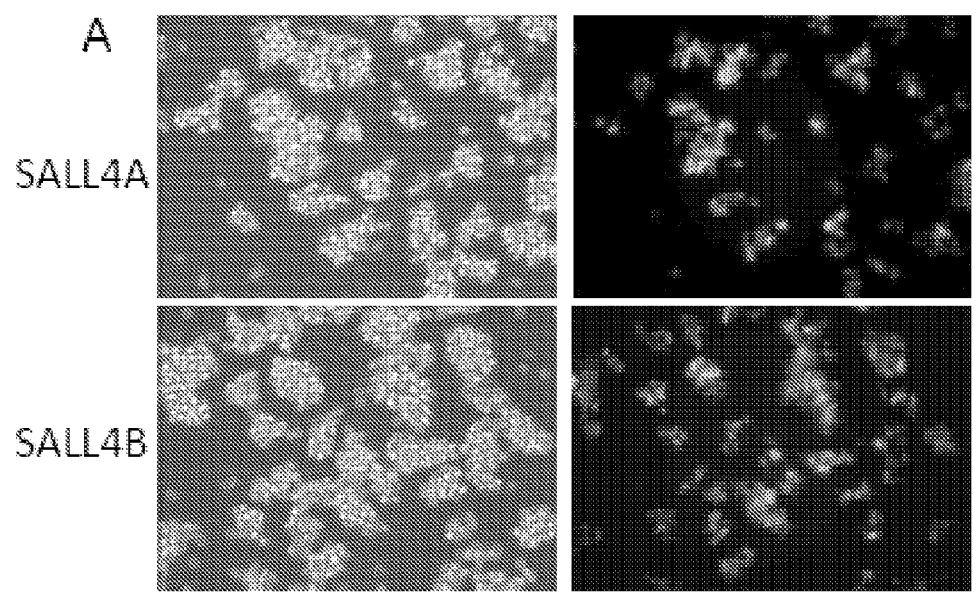
FIG. 3. (A) HSCs transduced with SALL4A and SALL4B are able to survive and expand rapidly 7 days after lentiviral infection. (B) CD34+ cells isolated from peripheral blood stem cells of 3 different patients. CD34+ cells were isolated from the stem cell pool using magnetic anti-CD34+ human microbeads. The CD34+ enriched cells were transduced with SALL4A and imaged under bright field and fluorescent microscopy. All three samples from the various patients were successfully transduced with SALL4A and expanded rapidly in culture. In addition, SALL4-induced HSCs are able to expand when growth factor concentrations are decreased.
Figure 3:
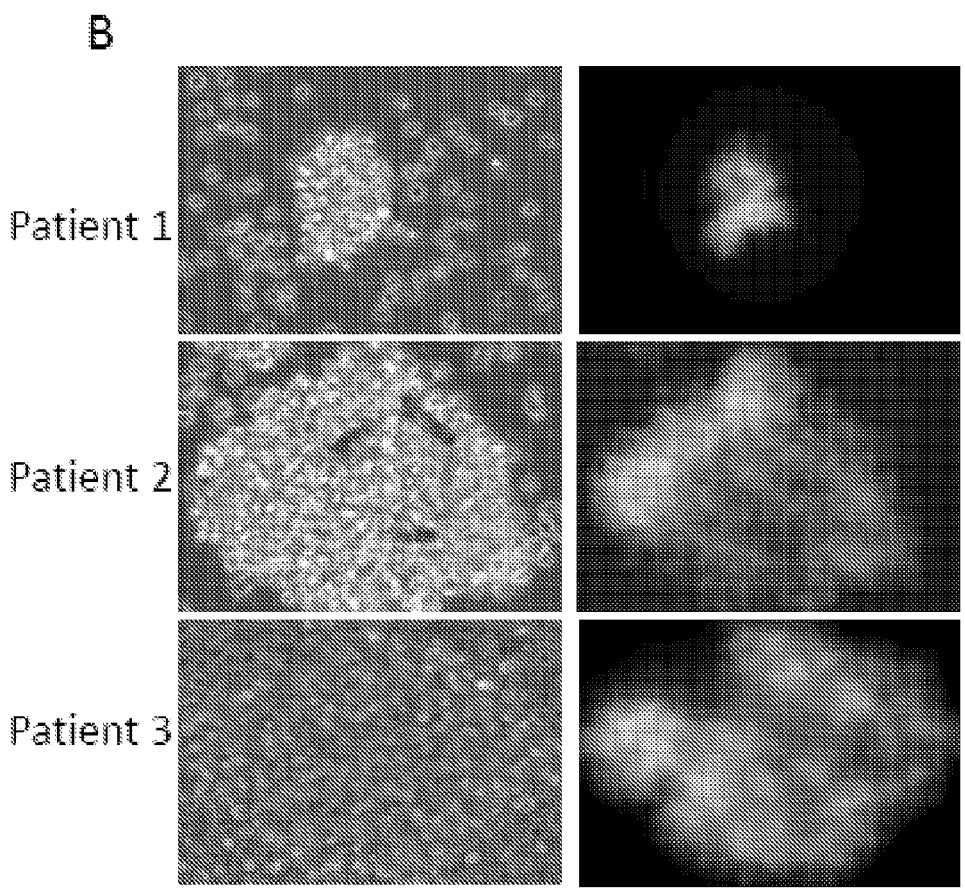
Figure 4:
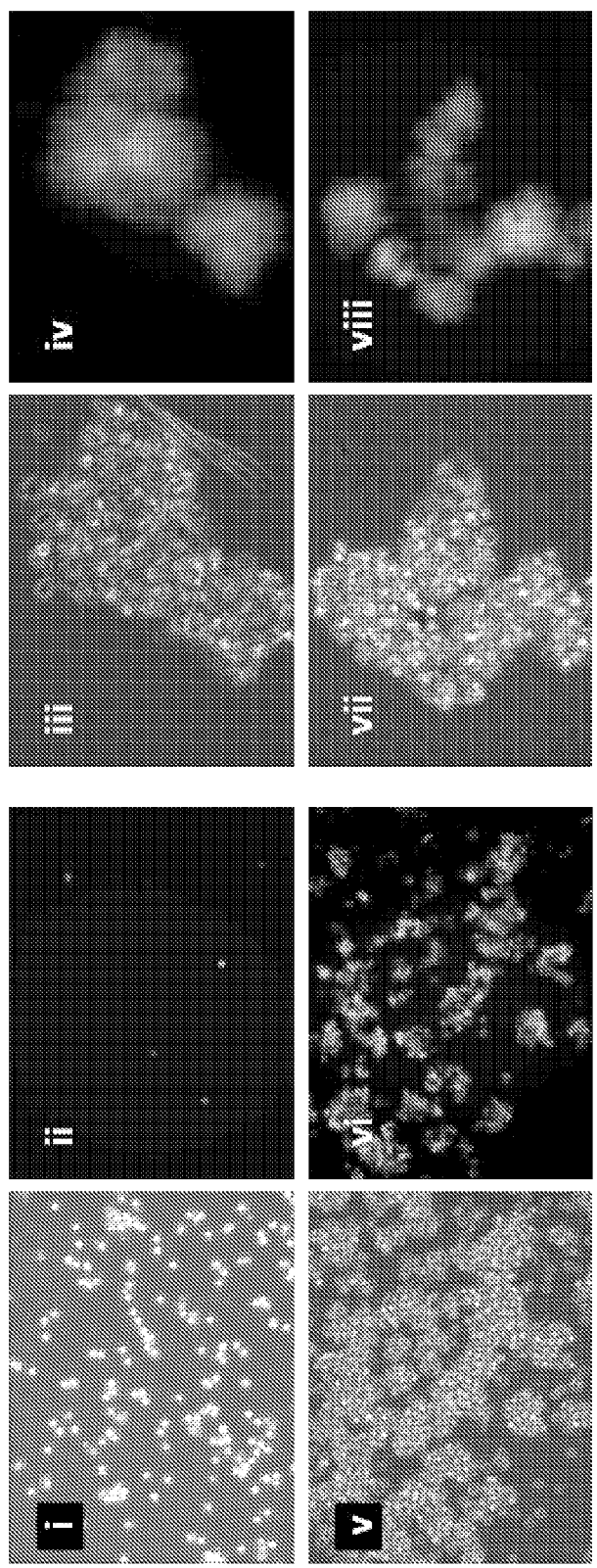
FIG. 4. Bright field and fluorescent images of human bone marrow CD34+ cells transduced with GFP (i and ii) or representative SALL4 isoform, B (v and vi) 9 days post infection. Initially, 50,000 CD34+/CD38− cells were plated. High magnification of SALL4B-transduced HSC clusters (vii, and viii). The GFP cell clusters signified positive overexpression of SALL4B. With SALL4B overexpression, HSC cell clusters are able to survive and are rapidly expanding at 9 days post infection.
Figure 5:
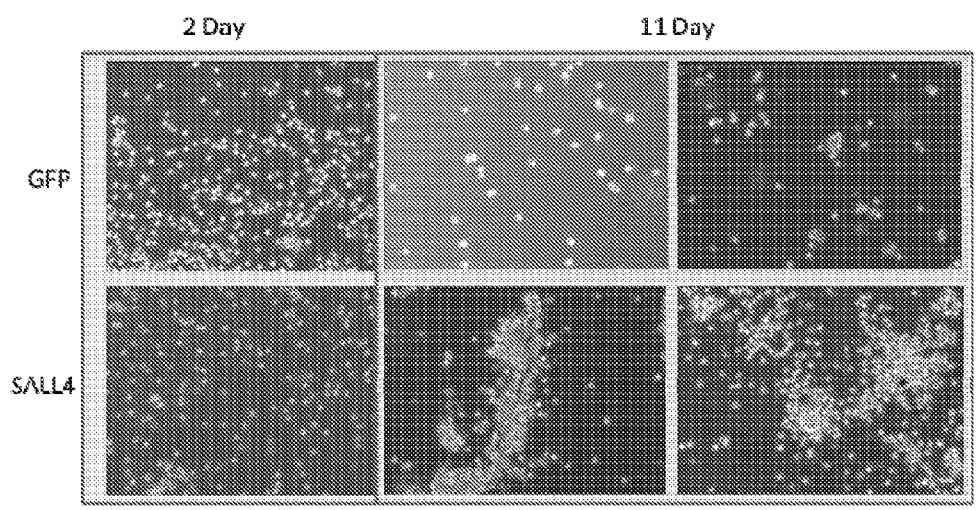
FIG. 5. Cell expansion of SALL4-induced HSCs versus control cells. At two days following lentiviral infection, similar amounts of HSC clones are visible in both the GFP-transduced and SALL4-transduced cell cultures. At 11 days post infection, the SALL4-transduced HSCs are proliferating and expanding. Notice the formation of proliferating cell clusters in the HSCs overexpressing SALL-4 compared to the low number of cells in the GFP-induced control HSCs.
Figure 6:
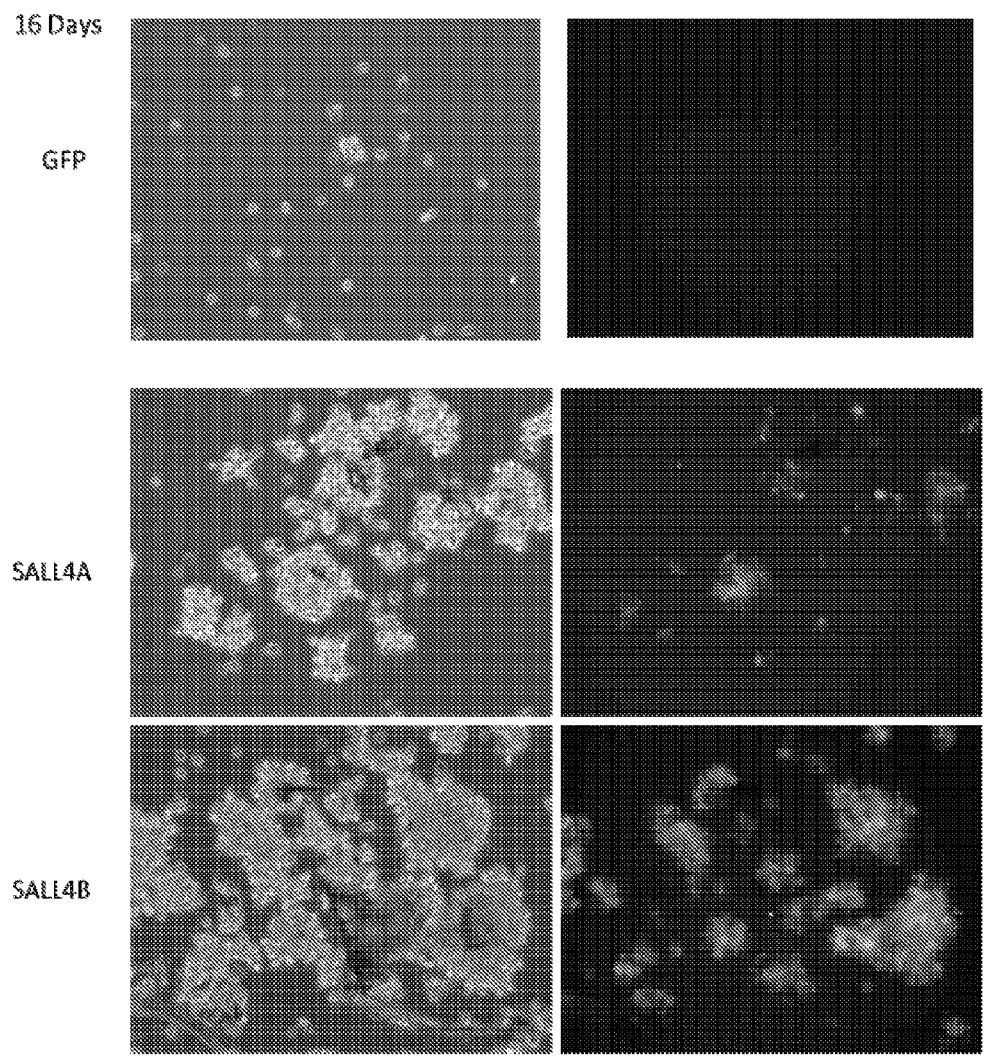
FIG. 6. 16 days post lentiviral infection, SALL4-induced HSCs continue to expand while control cells undergo cell death or differentiation. 16 days after infection, control GFP-transduced cells have depleted from the cell culture due to differentiation and death. In contrast, in HSCs overexpressing SALL4A or SALL4B, cells continue to expand and survive. Multiple healthy expanding clusters are visible throughout the cell culture.

The cells were observed daily for the next 14 days following the second lentiviral infection. They were observed qualitatively with bright field and fluorescent microscopy. During the first 48 hours, the cells transduced with either SALL4A or SALL4B expanded 10-fold and regularly formed GFP-positive cell clusters. In contrast, those cells transduced solely with GFP expanded approximately 2-fold but did not form many clusters. Instead, single cell or few small GFP-positive clusters were seen. After 7 days, the expansion cells appeared to be observed solely in the SALL4-transduced cells (FIG. 3A). After 8 to 11 days in complete growth media, those cells transduced with SALL4A or SALL4B expanded 200-400 fold (FIGS. 4 and 5). On the other hand, cells transduced only with GFP expanded 5-fold at most (FIGS. 4 and 5). Furthermore, the SALL4 transduced cells continued to survive and expand 16-days post lentiviral infection. These cells were able to expand 800-1000 fold without significant maturation over the first 2 to 3 weeks of culture while the majority of control cells had undergone death or differentiation (FIG. 6). Therefore, the expansion of cells was observed solely in the SALL4-transduced cells. The expansion experiments were repeated three times. In all trials, the SALL4A or SALL4B transduced human CD34+ cells were able to grow in the liquid culture medium, retain their undifferentiated appearance, and continue to grow for more than 2 months. Similar experiments were carried out utilizing CD34+ cells isolated from peripheral blood stem cells from patient samples. Our initial findings demonstrate that successful survival and expansion of these cells is also possible.

Figure 7:
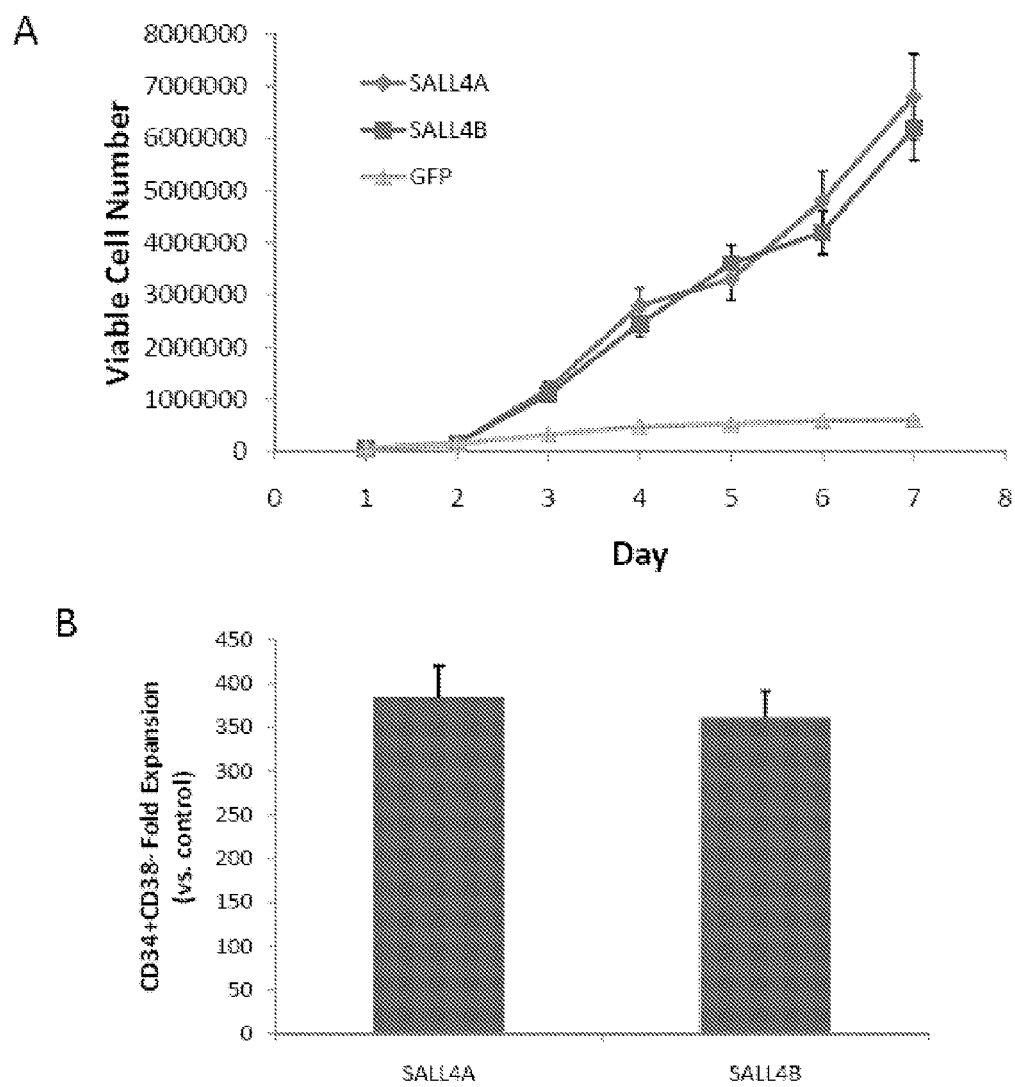
FIG. 7. (A) Growth curves of CD34+ cells transduced with SALL4A, SALL4B, or GFP and cultured in media containing 75% less cytokines. After transduction, 50,000 cells of each group were cultured in stringent conditions in which normal cytokine concentrations were decreased by 75%. HSCs transduced with SALL4A or SALL4B continued to survive and expand over 7 days while control cells growth halted at day 5. (B) Fold expansion of CD34+/CD38− cells 14-days post infection of Lenti-SALL4A or −SALL4B versus control. Cells transduced with SALL4A demonstrated a 368 fold increase of CD34+/CD38− cells over control while those transduced with SALL4B showed a 384 fold increase. (C) Phenotypic analysis of SALL4-induced hematopoietic stem cells 31 days post lentiviral infection. Human-specific antibodies CD34-PE and CD38-APC were utilized to compare SALL4-transduced HSCs versus 3-day control cells. 31 days after lentiviral infection, the aged SALL4-induced cells continued to demonstrate similar phenotypic ratios compared to control cells for CD34+/C38−. FLOW analysis was carried out on three separate samples. Therefore, many of these aged cells still attained progenitor characteristics and had the ability to differentiate into various cells lines. (D) 31-day old SALL4-induced HSCs attain blast-like morphology. Aged 31-day old SALL4-induced HSCs were Wright-Giemsa stained. Many cells showed blast-like morphology including large nuclei and scant cytoplasm. These cells represented a population of undifferentiated cells still visible 31 days after SALL4-lentiviral infection and expansion.
Figure 7:
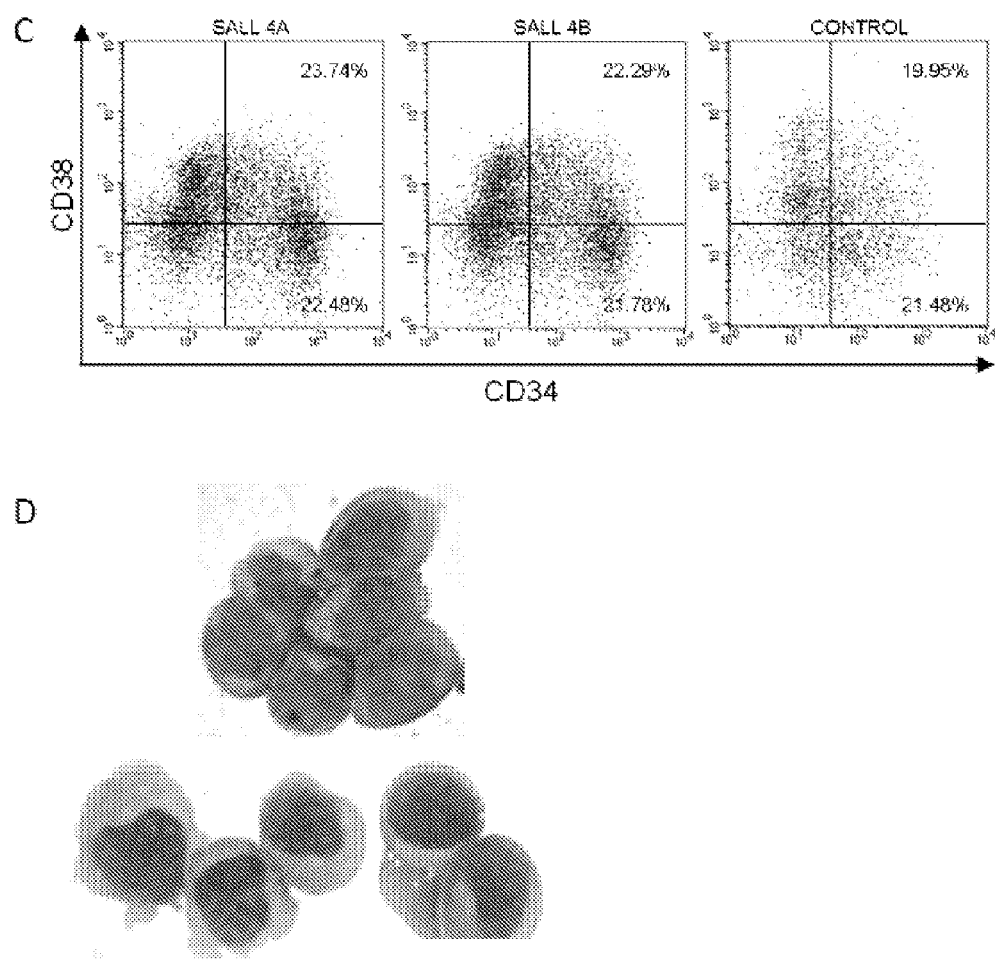
Figure 8:
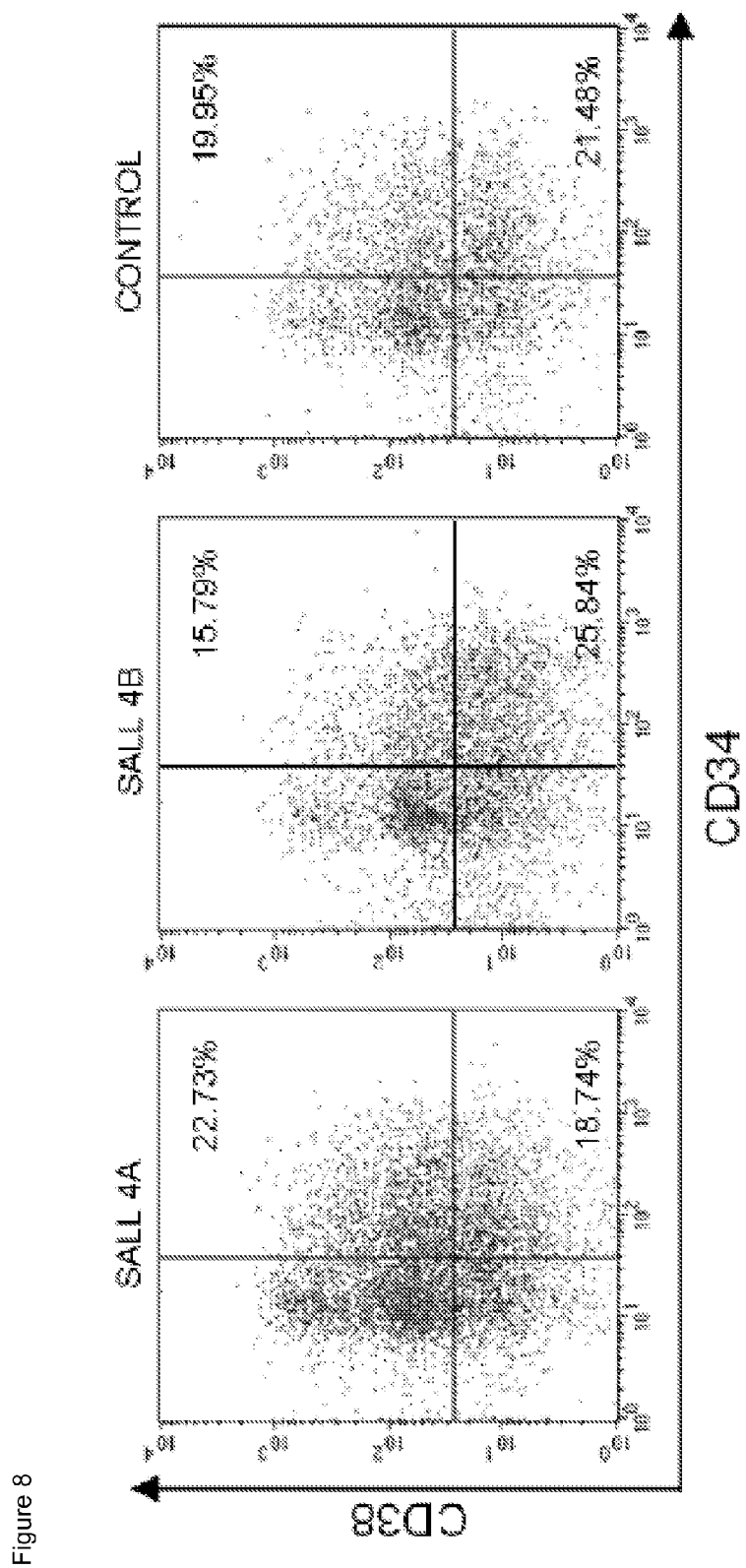
FIG. 8. Representative phenotypic analysis of SALL4-induced hematopoietic stem cells 14 days post lentiviral infection (n=4). Human-specific antibodies CD34-PE and CD38-APC were utilized to compare SALL4-transduced HSCs versus 3-day control cells.

Similar experiments were carried out utilizing CD34+ cells isolated from mobilized peripheral blood stem cells which were collected from patients and cryopreserved. Three samples from different patients showed promising results in CD34+ cell expansion (FIG. 3B). Cells transduced with SALL4A or SALL4B expanded approximately 130-fold while control cells expanded 12-fold at most (FIG. 7A). Furthermore, when these SALL4-transduced cells were grown for 14 days, the CD34+/CD38-population increased 369 fold for SALL4A and 384 fold for SALL4B (FIG. 7B) and maintained stem cell immunophenotypes (n=4)(FIG. 8). At 31 days of cell culture, the SALL4-transduced expanding cells still retained progenitor or stem cell immunophenotypes (n=2) (FIG. 7C) and primitive cell morphology (FIG. 7D). At the end of expansion, approximately 90% of the cells were expressing GFP. In contrast, control cells ceased to proliferate or were no longer viable after two weeks post-infection. SALL4 induced cells continued to expand with CD34+/CD38− or CD34+/CD38+ ratios similar to that of the original cells the culture began with (FIG. 7).

The expansion experiments were repeated at least 12 times using a variety of sources for the CD34+ cells (Table 1). In all trials, the SALL4A or SALL4B transduced human CD34 cells were able to expand in the liquid culture medium for more than 2 months and demonstrated similar percentages of cell populations (15% CD34+/CD38−, 17% CD34+/CD38+) to 31-day old cells, as demonstrated by flow cytometry.

TABLE 1

Sources of CD34+ Cells

| Source of CD34+ cells | Source |
| --- | --- |
| AllCells | 27 yrs; female; Filipino/Caucasian |

TABLE 1-continued

Sources of CD34+ Cells

| Source of CD34+ cells | Source |
| --- | --- |
| AllCells | 27 yrs; female; Filipino/Caucasian |
| AllCells | 32 yrs; male; Caucasian |
| AllCells | 32 yrs; trials; Caucasian |
| AllCells | 32 yrs; male; Caucasian |
| SBUMC Bone Marrow Transplant Lab | Confidential |
| SBUMC Bone Marrow Transplant Lab | Confidential |
| SBUMC Bone Marrow Transplant Lab | Confidential |
| AllCells | 22 yrs; male; Caucasian |
| AllCells | 22 yrs; male; Caucasian |
| AllCells | 22 yrs; male; Caucasian |
| AllCells | 22 yrs; male; Caucasian |

Example 2

Single SALL4-induced CD34+ Cell Clusters Readily Expand in Culture

Figure 9:
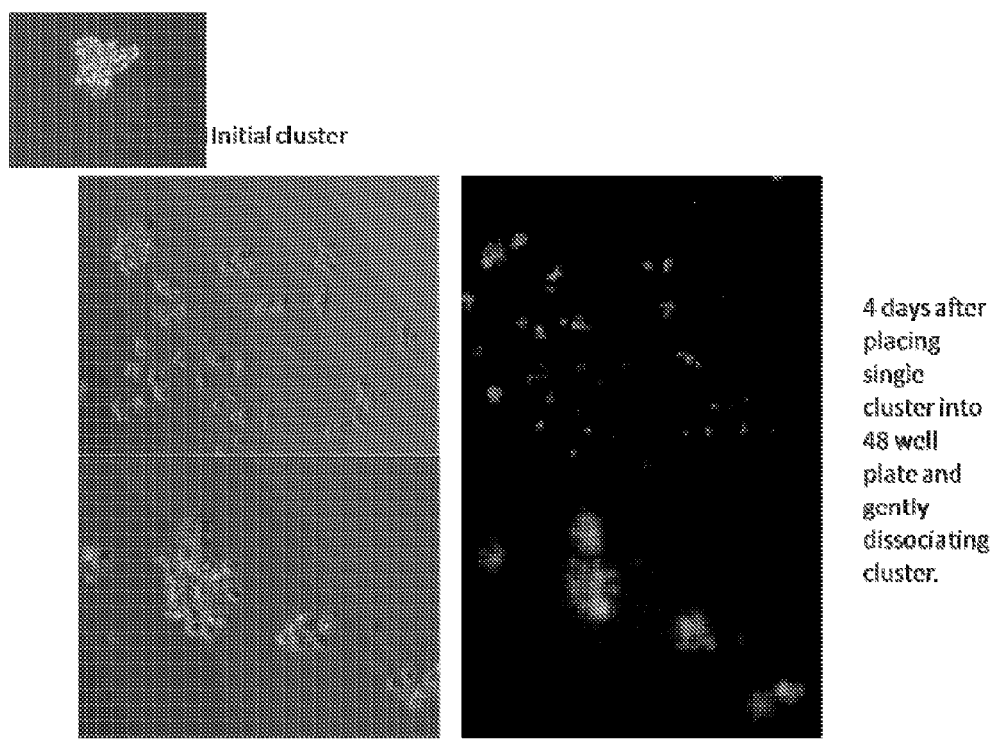
FIG. 9. A single SALL4-induced GFP-positive cluster can be dissociated and expanded to form new HSC clusters. A single 7-day old cluster overexpressing SALL4 was picked from an initial cell culture, gently dissociated, and replated into a single well of a 48-well plate. 4 days later, the HSCs were able to expand and form new proliferating healthy cell clusters leading to a net increase in the number of clones.

From days 5-14 large GFP-positive cell clusters could readily be observed throughout the cell cultures transduced with SALL4A or SALL4B. In order to see if these clusters could serve as a seed for further expansion, single cell clusters were picked from the parental plate and placed into individual wells of a 48-well plate. The cluster was gently dissociated by aspiration through a 100 µl pipet tip. The next day (day 6-15) new small GFP positive cell clusters began to form again (FIG. 9). These clusters were allowed to expand for 5 days with complete growth media and began to grow at a similar rate as seen in the initial parental plates (FIG. 9). Therefore, it is possible to select SALL4-transduced cell clusters and expand them 200-400 fold over 7 days.

Figure 10:
FIG. 10. 18-day old SALL4-induced HSCs attain blast-like morphology. Aged 18-day old SALL4-induced HSCs were placed in a cytospin and giemsa stained. Many cells showed blast-like morphology including large nuclei and scant cytoplasm. These cells represented a population of undifferentiated cells still visible 18 days after SALL4-lentiviral infection and expansion.
Figure 11:
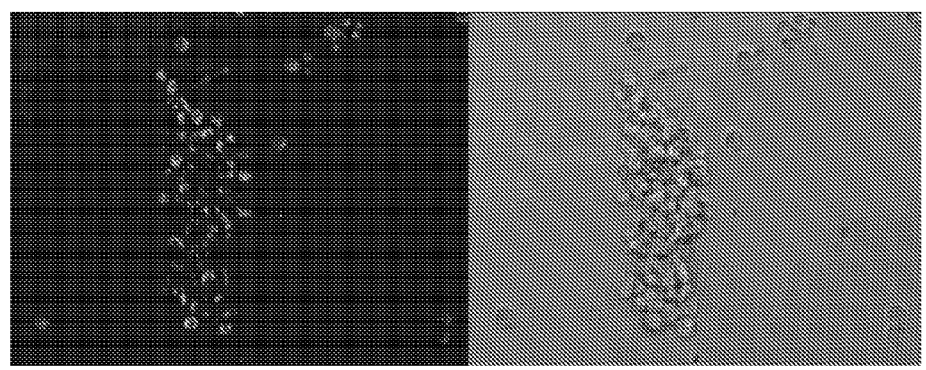
FIG. 11. CFU progenitors are GFP-positive. HSC cells selected for CFU assays were GFP-positive which verified that the cells were successfully transduced and overexpressing SALL4.
Figure 12:
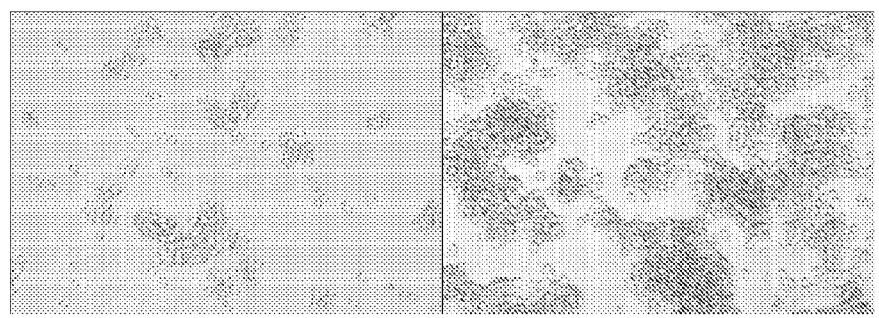
FIG. 12. Various CFU colonies are able to differentiate from SALL4-induced HSCs. Aged SALL4-induced HSCs were plated in Methocult and observed for CFU colonies. Numerous lineages were observed in CFU assays utilizing the SALL4-induced HSCs including BFU-E, CFU-GM, and CFU-GEMM colonies. These data demonstrated that the aged HSCs transduced with SALL4 were capable of differentiating into different blood cell lineages.
Figure 12:
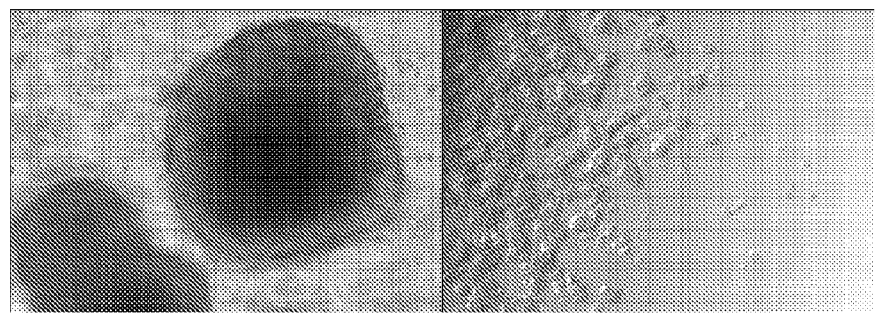

To further illustrate the survival and expansion capabilities of the aged SALL4-transduced HSC colonies, 18-day old cells were placed in a cytospin and Giemsa stained to observe their morphology. Interestingly, more than 90% of the cells exhibited blast-like morphology with large nuclei and scant cytoplasm (FIG. 10). These cells resembled undifferentiated cells. In addition, aged SALL4-transduced HSCs were cultured in Methocult and scored for CFUs. The SALL4-transduced GFP positive HSCs were able to differentiate into variable CFU colonies including BFU-E, CFU-GM, and CFU-GEMM (FIGS. 11 and 12). Therefore, the HSC SALL4 induced cells still had the ability to form a variety of blood lineages similar to wild type CD34 cells.

Example 3

Ex Vivo SALL4 Induced Expansion of Human Hematopoietic Stem Cells Under Stringent Conditions In order to demonstrate that SALL4 induced HSCs were capable of expanding at a faster rate and higher volume compared to controls, cell culture experiments were conducted in which recombinant cytokine concentrations were decreased significantly. If the SALL4 transduced HSCs were able to successfully grow at these more stringent conditions, we could solidify our findings that SALL4 is pertinent for the maintenance of an undifferentiated proliferation state and blocking cell differentiation of HSCs.

Figure 13:
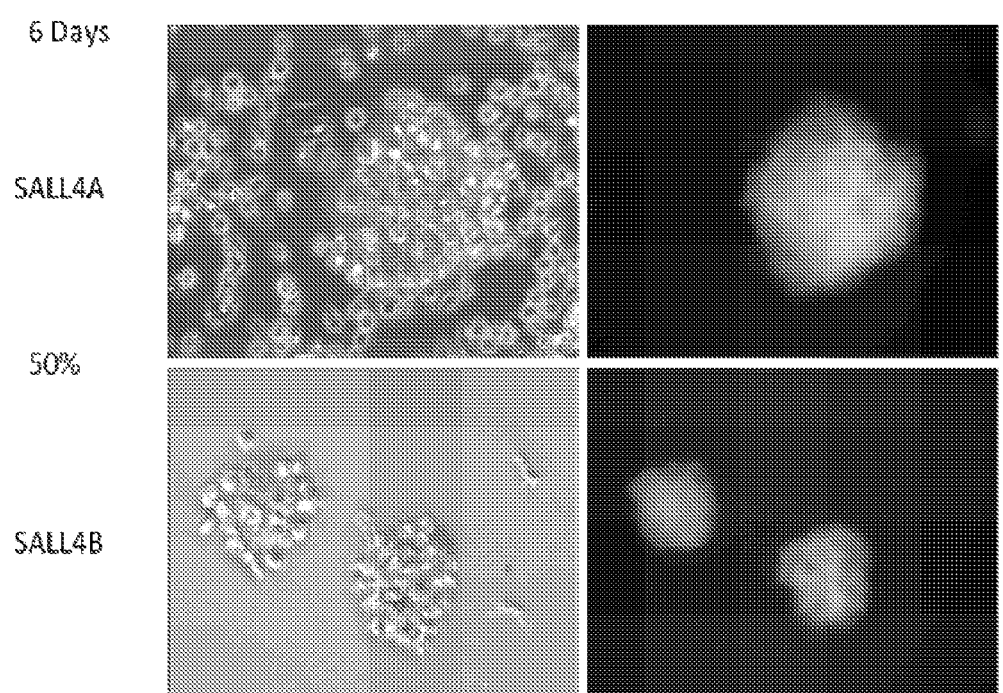
FIG. 13. SALL4-induced HSCs are able to expand when growth factor concentrations are decreased by 50%. When SALL4-transduced HSCs were cultured in growth media containing 50% less cytokines, they were still able to survive and expand 6 days post lentiviral infection. Furthermore, when growth factor concentrations were decreased to 25% of original values, the SALL4-transduced HSCs continued to proliferate. In contrast, control cells had undergone cell death by day 6.
Figure 14:
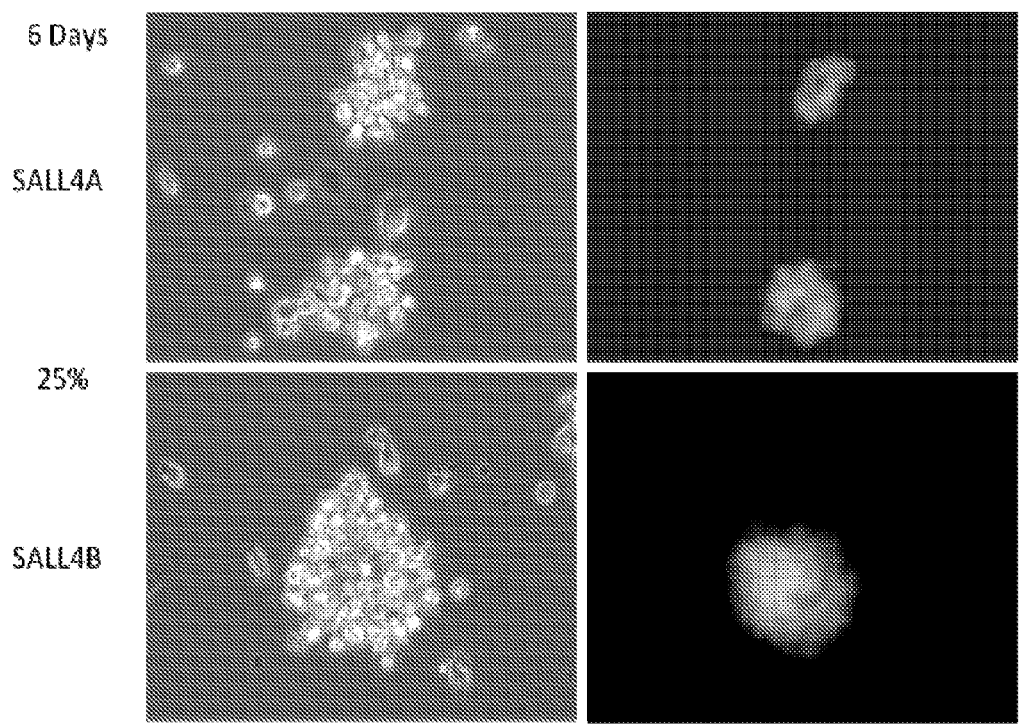
FIG. 14. SALL4-induced HSCs successfully proliferate when growth factors are decreased by 25%. SALL4-induced HSCs are able to expand when growth factor concentrations are decreased by 50%. When Sall4-transduced HSCs were cultured in growth media containing 50% less cytokines, they were still able to survive and expand 6 days post lentiviral infection. Furthermore, when growth factor concentrations were decreased to 25% of original values, the SALL4-transduced HSCs continued to proliferate. In contrast, control cells had undergone cell death by day 6.

Cell culture experiments were conducted in which recombinant growth factor concentrations were decreased by 50 or 25% for both SALL4 induced HSCs and control cells. Cell growth was monitored during the first week. Interestingly, cells transduced with SALL4A or SALL4B were still able to survive and expand beyond 6 days of culture (FIGS. 13 and 14). In contrast, control cells had undergone cell death by day 6 and no viable colonies could be observed. In addition, under these conditions, SALL4 transduced human CD34+ cells were able to maintain their undifferentiated appearance and continue to grow for more than 2 months in the liquid medium.

This provides the first evidence that under stringent growth conditions, in which the concentrations of necessary recombinant cytokines is reduced, SALL4 induced HSCs still have the survival and expansion capacity of those that are cultured at 100% concentrations. This proves SALL4 plays a key role for maintaining HSCs in an undifferentiated proliferation state.

Figure 15:
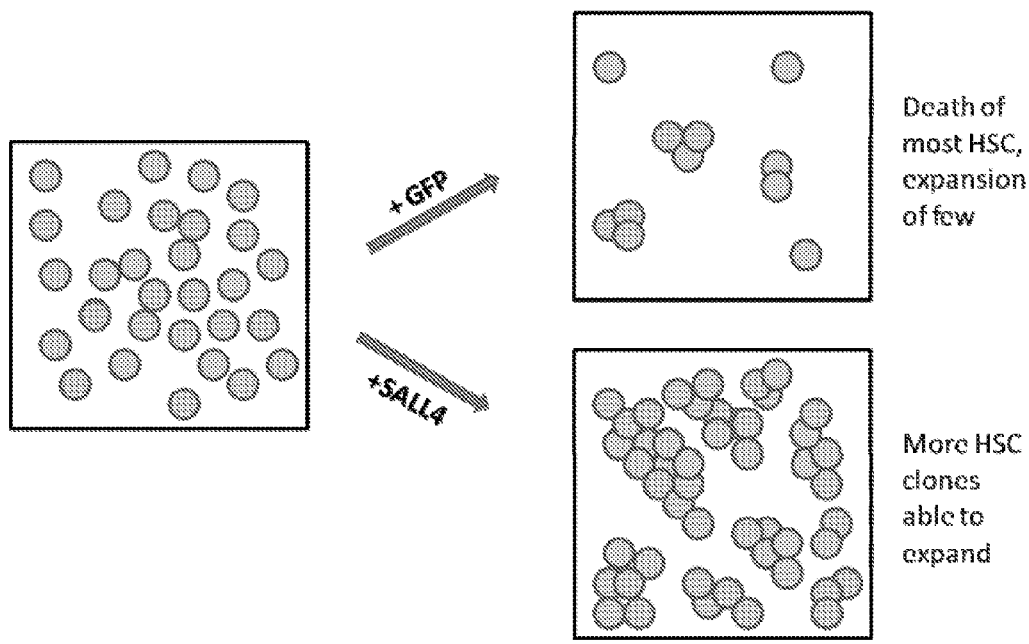
FIG. 15. Model of SALL4-mediated ex vivo HSC expansion. The primary culture was divided and transduced with a SALL4 or GFP control. The viable HSCs without SALL4 overexpression decreased in number due to differentiation or death leading to a net HSC decline. In contrast, HSCs in which SALL4 was overexpressed, many clones were able to survive and expand in the culture. A net HSC expansion was exhibited with numerous expanding clusters throughout the culture.

This is the first data to illustrate that transduction of bone marrow CD34+ cells with SALL4 offer a means to successfully expand HSC cells. HSCs without SALL4 overexpression decreased in number due to differentiation or death leading to a net HSC decline. In contrast, HSCs in which SALL4 was overexpressed, many clones are able to survive and expand in the culture. A net HSC expansion was exhibited with numerous expanding clusters throughout the culture (FIG. 15). This data increases our knowledge on how HSC self-renew and expand. Furthermore, this knowledge could be transferred for protocols to expand clinically useful numbers of HSC for bone marrow transplantation and targeted gene therapy for hematologic disorders.

In other experiments, SALL4-transduced cells were grown in culture with various combinations of the growth factors SCF, TPO, and FLT-3L. After 14 days of culture, it was noted that the growth and survival of SALL4-transduced cells were independent of FLT-3L, partially dependent on TPO, and dependent on SCF (Table 2).

TABLE 2

Dependence of SALL4-Transduced Cells on Certain Growth Factors

| Cytokine | SALL4A | SALL4B |
| --- | --- | --- |
| FLT-3 | Independent | Independent |
| TPO | Partially Dependent | Partially Dependent |
| SCF | Dependent | Dependent |

Example 4

Morphology and Phenotyping of Aged SALL4-Induced HSCs

Figure 16:
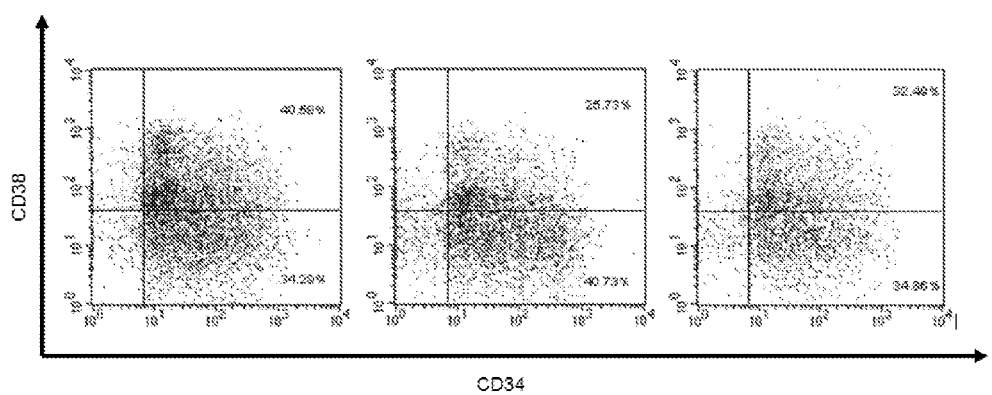
FIG. 16. Phenotypic analysis of SALL4-induced hematopoietic stem cells 14 and 23 days post lentiviral infection. Human-specific antibodies CD34-PE and CD38-APC were utilized to compare SALL4-transduced HSCs versus control cells. 14 (top) and 23 (bottom) days after lentiviral infection, the aged SALL4-induced cells continued to demonstrate similar phenotypic ratios compared to control cells for CD34+/C38−. Therefore, many of these aged cells still attained progenitor characteristics and had the ability to differentiate into various cells lines.
Figure 16:
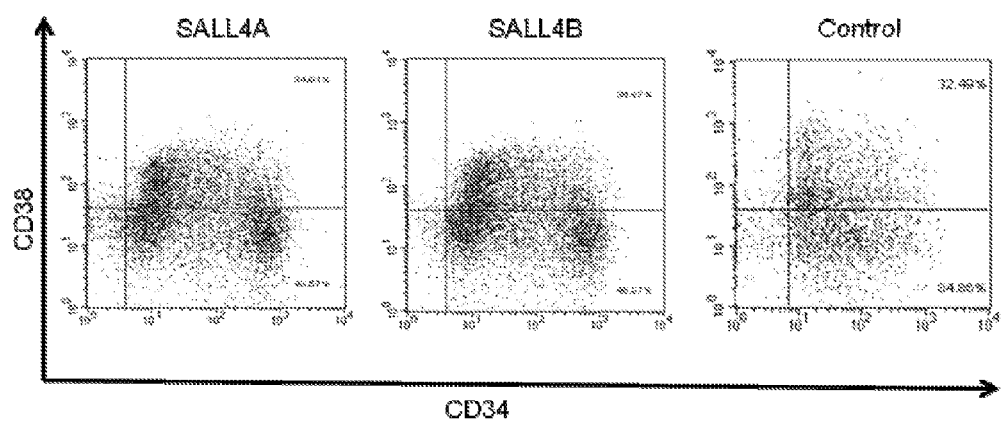

In order to demonstrate that the SALL4-induced HSCs had progenitor characteristics after being aged for several weeks, cytpospins and giemsa staining of the cells was conducted at different time points. Interestingly, both 16 and 31 days after lentiviral infection the cells morphology highly resembled progenitor cells with large nuclei and scant cytoplasm (FIG. 10). In addition, FLOW analysis was conducted and showed the ratios of CD34+/CD38− cells were similar in controls versus aged SALL4-induced cells at two distinct time points (FIG. 16). This was a key finding because the cells still demonstrated an undifferentiated progenitor state at a high percentage even after being cultured for several weeks.

Figure 17:
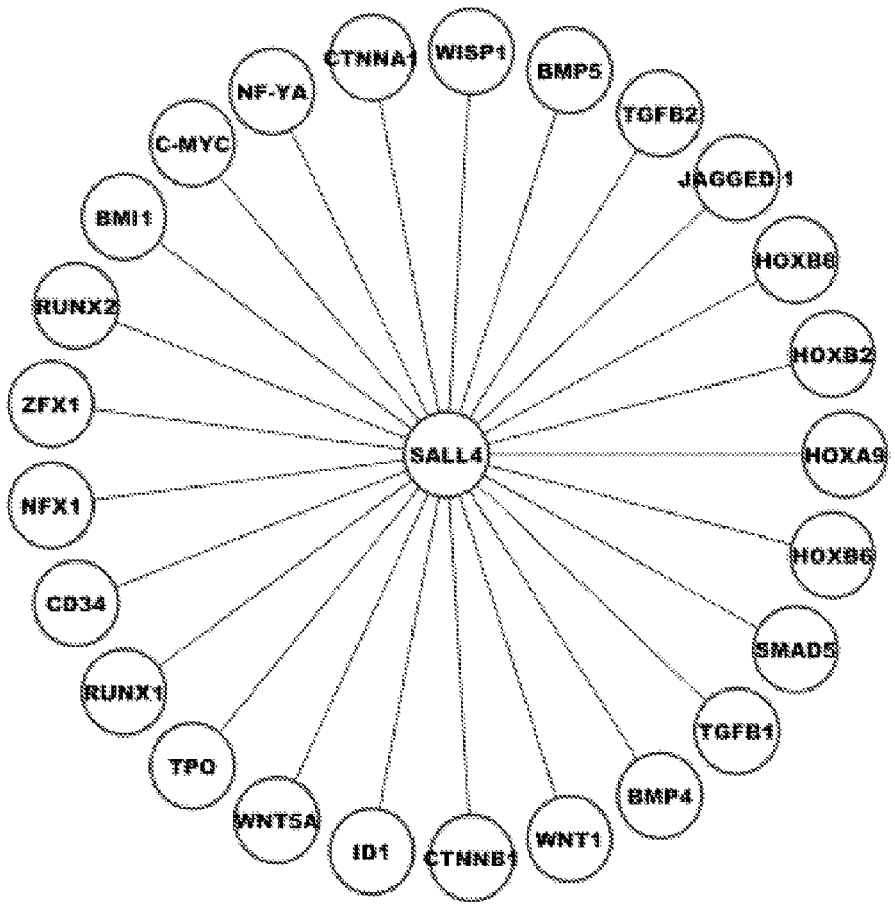
FIG. 17. SALL4 binds to important HSC signaling genes.

Previous studies have illustrated that SALL4 plays an important role in both cell survival and apoptosis. In addition, SALL4 has the ability to bind to the promoter regions of numerous genes that play a key role in HSC expansion and renewal including BMI1, WNT1, and TGFB1 (FIG. 17).

Example 5

Overexpression of SALL4 Inhibits Granulocytic Differentiation in the 32D Cell Line To further determine how SALL4 effects stem cell growth, studies were extended to the myeloid progenitor cell line, 32D where it is normally expressed. 32D cells proliferate as undifferentiated blasts when maintained in IL-3, but differentiate into mature neutrophilic granulocytes when stimulated with G-CSF.

32D cells were cultured for 3 days with growth media containing IL-3. On the third day, the cells were divided into six groups of $5 \times 10^4$ cells and placed into separate wells of a 12-well plate. The cells were then transduced with either a SALL4A, SALL4B, or GFP (control) human lentivirus for 2 hours. After two hours, the cells were allowed to recover in growth media. 24 hrs later, the cells were once again transduced with the aforementioned lentiviruses. The next day, the cells were observed for GFP positive cells. It was noted that approximately 30% of the cells were fluorescent. The cells were allowed to expand for 48 hours in full growth media supplemented with IL-3. After the 48 hours, the cells were collected, washed, and re-plated to new wells containing growth media without IL-3, but supplemented with G-CSF.

Figure 18A:
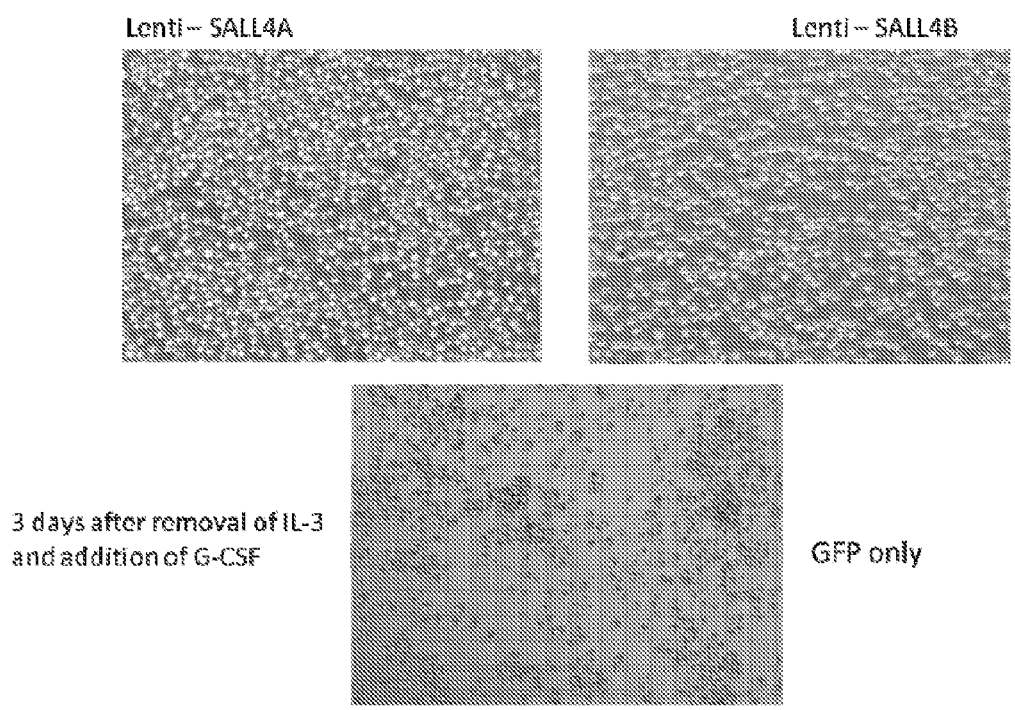
FIG. 18. CD34+ cells isolated from peripheral blood stem cells of 3 different patients. CD34+ cells were isolated from the stem cell pool using magnetic anti-CD34+ human microbeads. The CD34+ enriched cells were transduced with SALL4A and imaged under brightfield and fluorescent microscopy. All three samples from the various patients were successfully transduced with SALL4A and expanded rapidly in culture.
Figure 18B:
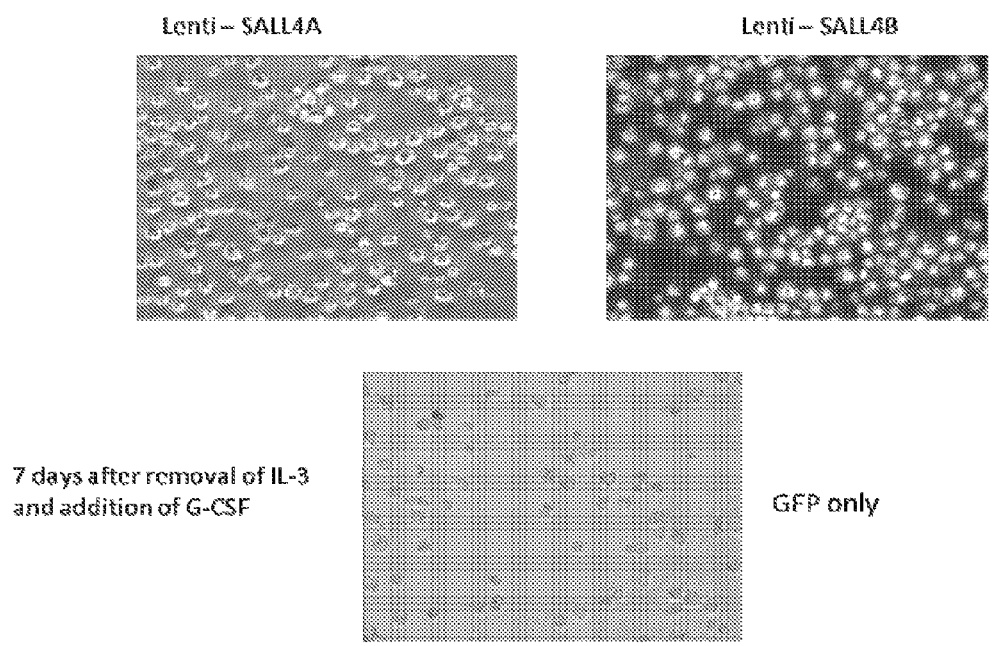
Figure 19:
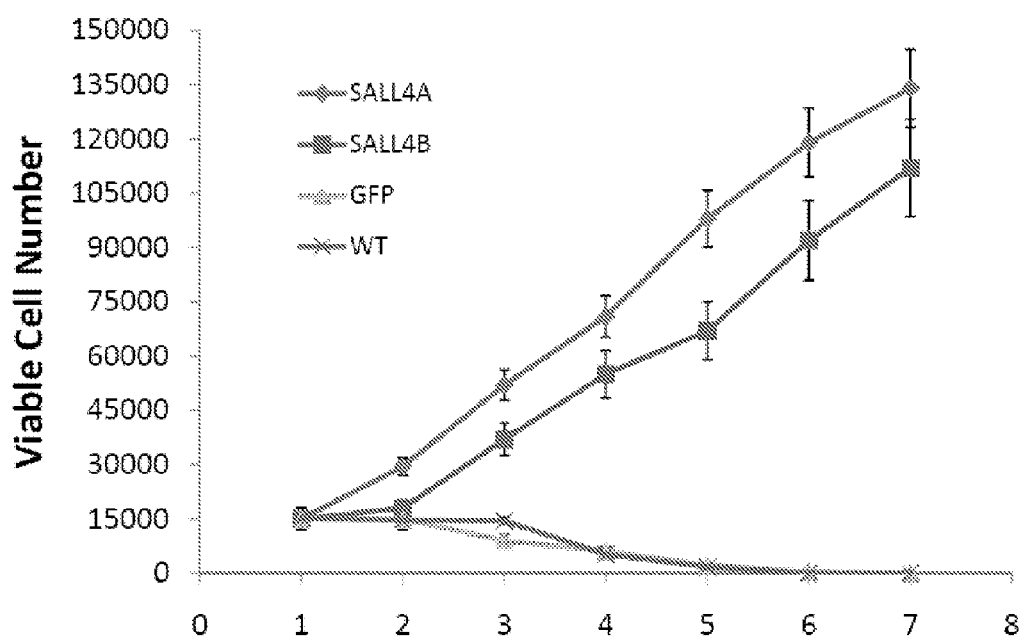
FIG. 19. Growth curves of SALL4 induced 32D cells cultured only with G-CSF. 32D cells were transduced with SALL4A, SALL4B, or GFP lentivirus then cultured for three days in growth media containing IL-3. On the 4th day, 15000 cells were aliquoted from each group and placed in new growth media with G-CSF and without IL-3. Cell growth was monitored daily and the viable number of cells in each group was recorded. In cells that were transduced with SALL4A, an 8-fold increase in the number of cells was observed from day 1 to 7. Cells that were transduced with SALL4B exhibited a 7-fold expansion of cells. In contrast, cells that were only transduced with GFP and WT (no lentiviral infection) demonstrated a decrease in the number of cells over the same period with almost all the cells undergoing cell death by day 5.
Figure 20:
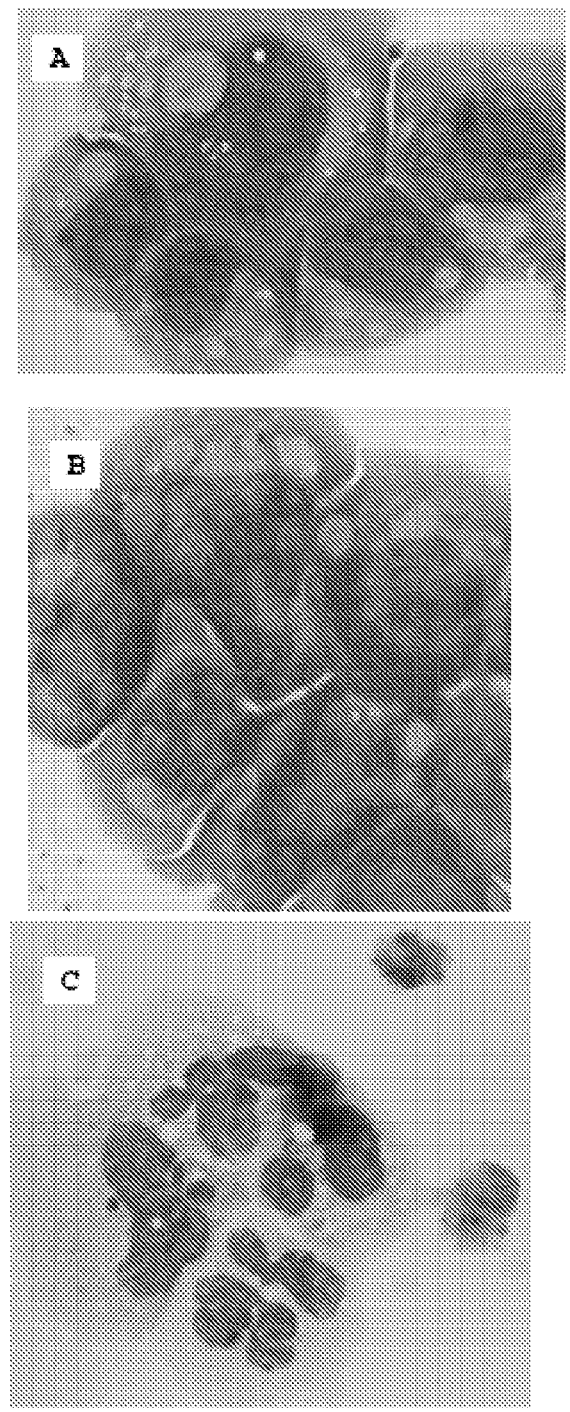
FIG. 20. Wright-Giemsa staining of 32D cells. Morphology of 32D cells with IL3 alone (A), transduced with SALL4A with G-CSF (B) and with G-CSF alone (C). Cells given IL3 or transduced with SALL4A continue to demonstrate blast-like morphology (A or B), while the cells not transduced with SALL4A and given G-CSF exhibit neutrophil morphology (C).

The cells were observed daily for the next seven days qualitatively with bright field and fluorescent microscopy and also counted with a hemacytometer. Throughout days 1-7, the cells transduced with SALL4A or SALL4B continued to expand at a steady rate even though IL-3 was removed from the growth media. The 32D-SALL4A or 32D-SALL4B proliferated at a 3-fold or 6-fold higher rate than the control counterpart after 3 days of culture in G-CSF (FIG. 18). The control, 32D cells died after 5-6 days in G-CSF but 32D-SALL4A and 32DSALL4B cells grew indefinitely in culture when IL-3 was removed, and replaced with G-CSF. Furthermore, these cells behaved identically to unmodified 32D cells (FIGS. 18 and 19). Expression of SALL4A or SALL4B permitted continued growth of cells in an undifferentiated state. While the control 32D cells exhibited appropriate granulocyte maturation, 32D-SALLA or 32D-SALL4B cells did not show significant granulocytic maturation with their morphology very similar to the 32D-SALL4 parent population. 32D cells proliferate as undifferentiated blasts when maintained in IL-3 (FIG. 20 iv), but differentiate into mature neutrophilic granulocytes when stimulated with G-CSF (FIG. 20 vi). SALL4 transduced 32D cells grew indefinitely without IL-3, and retained undifferentiated blast morphology when given G-CSF (FIG. 20 v). This study indicates that hematopoietic stem cell differentiation can be blocked by constitutive expression of SALL4.

Example 6

Interactions of SALL4A and SALL4B In vitro

Figure 21:
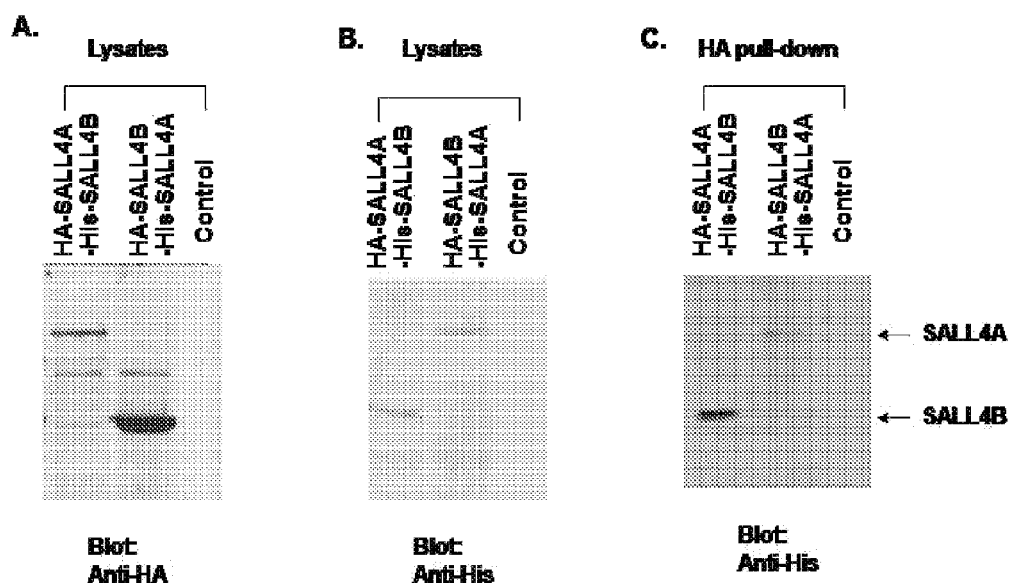
FIG. 21. The HA-SALL4A and His-SALL4B or HA-SALL4B and His-SALL4A transfected lysate of 293 cells were mixed with equal amounts and blotted with Anti-HA and Anti-His showing the present of these proteins in the lysates. Each lysate mixture was used to pull-down with Anti-HA antibody and resulting precipitated protein mixtures were subjected to Western blotting using antibodies against His tag.

To determine if the SALL4A or SALL4B protein forms homodimers or heterodimers in vitro, SALL4A or SALL4B were tagged with either HA or His (six histitine residues) and anti-HA pull-down assays was performed. As shown in FIGS. 21A and B, HA-SALL4A and His-SALL4B or HA-SALL4B and His-SALL4A proteins were expressed. Anti-HA pull down assays were performed. As seen in FIG. 21C, either His-SALL4A or His-SALL4B was pulled down by either HA-SALL4A or HA-SALL4B.

Example 7

Functional Analysis of SALL4 Induced CD34+ Cells In vitro

Figure 22:
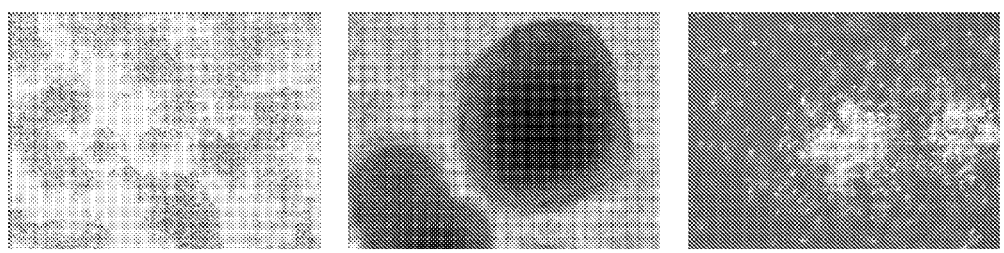
FIG. 22. (A) Various CFU colonies are able to differentiate from SALL4-induced HSCs. Aged SALL4-induced HSCs were plated in Methocult and observed for CFU colonies. Numerous lineages were observed in CFU assays utilizing the SALL4-induced HSCs including CFU-GEMM, BFU-E, and CFU-GM colonies. These data demonstrated that the aged HSCs transduced with SALL4 were capable of differentiating into different blood cell lineages. (B) Number of CFU colonies formed from SALL-4 induced hematopoietic stem cells. The number of CFU colonies was counted 13-18 days after SALL-4 induced or GFP-induced cells were cultured in CFU Methocult media. The representative data from day 18 are shown. (C) Types of CFU colonies formed at day 18.
Figure 22:
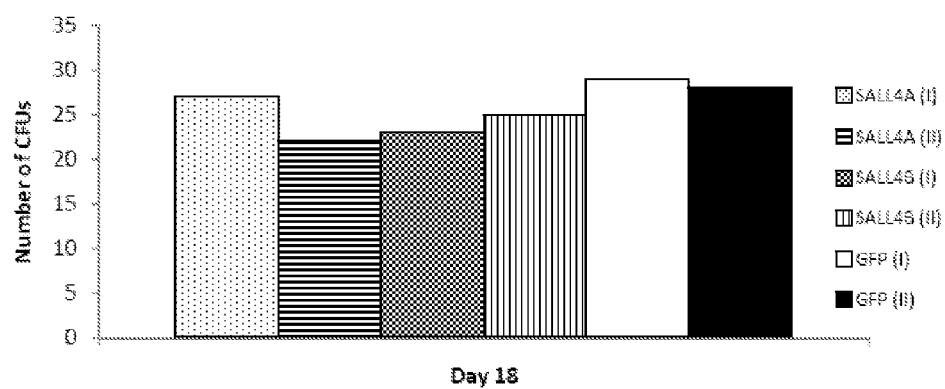
Figure 22:
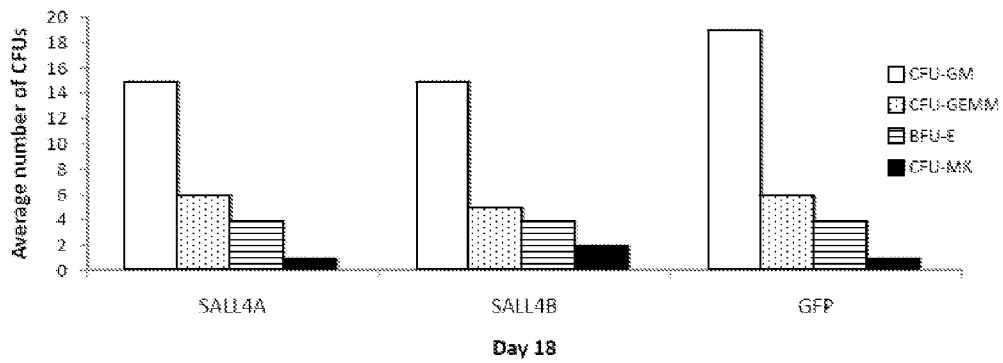

To further study the proliferation potential of the SALL4-transduced HSCs without an excess of special cytokines, colony-forming unit (CFU) assays were conducted. The CFU progenitors used for the study were initially GFP-positive signifying the expression of SALL4 protein (FIG. 11) and were cultured for at least one month in media containing the cytokines SCF, TPO, and FLT-3L. The CFU assays, conducted in methocult media without these cytokines, revealed that these cells could form various colonies including CFU- GM, CFU-GEMM, and BFU-E (FIG. 22A). In addition, the one month-old transduced cells had the capability to form similar numbers of CFU colonies compared to 2-day old GFP-transduced control cells when counted 18 days after the CFU assay was initialized (FIGS. 22B and 22C). Without wishing to be bound by any scientific theory, this study may indicate that SALL4 works in conjunction with other cytokines in order to block HSC differentiation and that other cytokines may by needed to inhibit differentiation.

Figure 23:
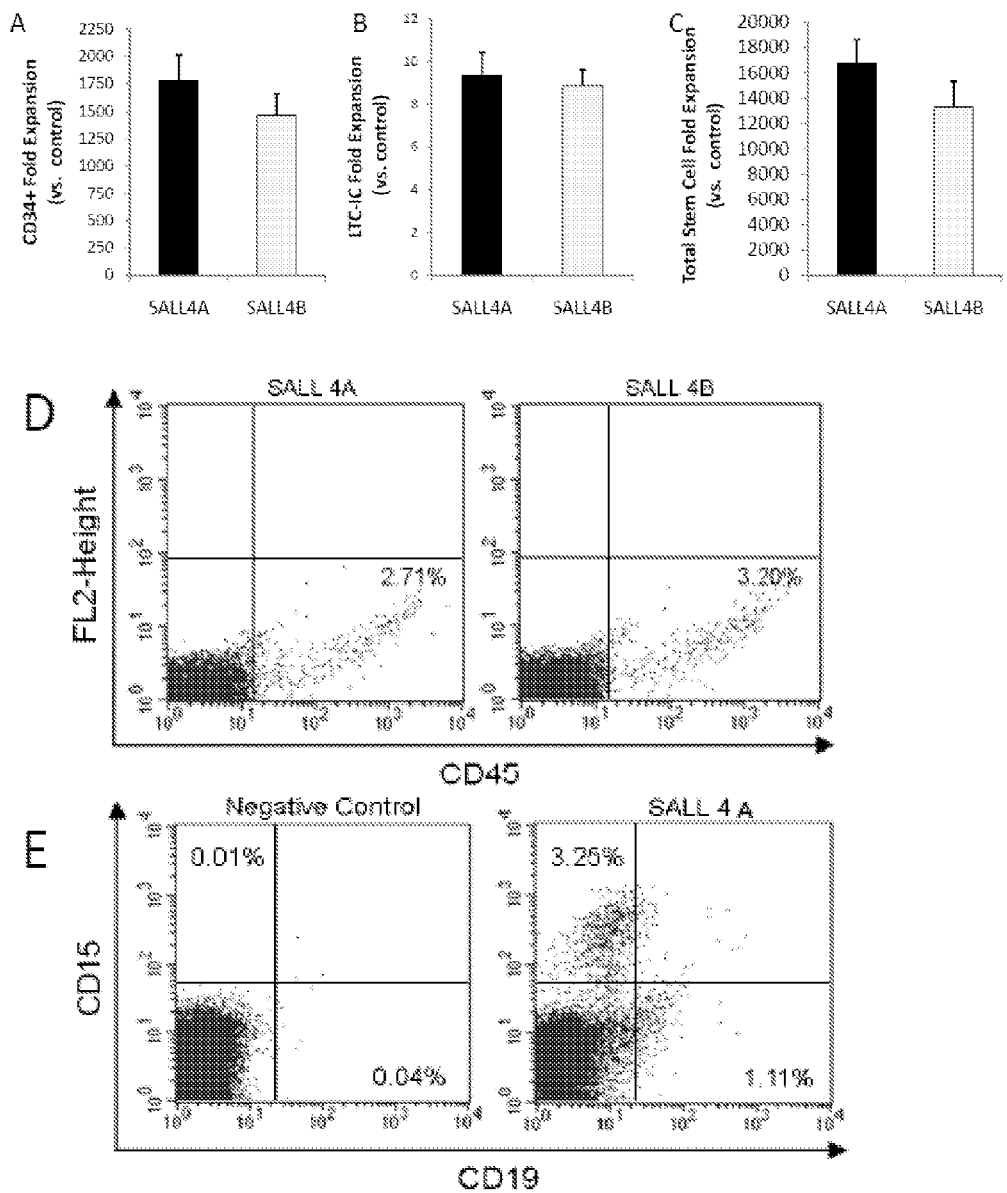
FIG. 23. (A) After one month of cell culture, CD34+ cells transduced with SALL4A or SALL4B had 1780 and 1463 fold increases respectively relative to control cells. Values are means±s.d. (B) Furthermore, SALL4 transduced cells showed 9.32 fold increases for SALL4A and 8.88 fold increases for SALL4B versus controls for the total number of LTC-ICs after one month. Values are means±s.d. (C) Overall, SALL4A transduced cells had a total fold CD34+/CD38− stem cell expansion 16776 over control while SALL4B transduced cells showed 13320 fold increases. Values are means±s.d. (D) Representative flow cytometry analysis 4 weeks post-injection for CD45+ human leukocytes from peripheral blood of NOD/SCID recipients transplanted with SALL4A- or SALL4B-transduced HSCs. (E) Representative flow cytometry profile 4 weeks post-injection of a mouse exhibiting multilineage repopulation of human cells by engrafted cells. While the negative control animal showed no engraftment of human cells, the experimental animal showed both CD15+ myeloid and CD19+ lymphoid human cell engraftment. (F) and Flow analysis of secondary and tertiary bone marrow transplant NOD/SCID mice. The animals were positive for CD45+ cells in both secondary (2.74%) and tertiary (3.29%) transplants. When the CD45+ population in the tertiary transplant was analyzed further for specific lineages, CD33 myeloid and CD19/CD3 lymphoid cells were positively measured (G). (H) Amount of human chimerism in the peripheral blood of NOD-SCID mice transplanted with 20,000 (SALL4A (■), SALL4B (▲), or GFP (♦)) or 40,000 (SALL4A (□), SALL4B (Δ), or GFP (◊)) initial human CD34+ cells. (I) Limiting-dilution analysis of CD34+ bone marrow cells injected into NOD-SCID mice (n=72) after lentiviral transfection with SALL4A (□), SALL4B (▲), or GFP (○).
Figure 23:
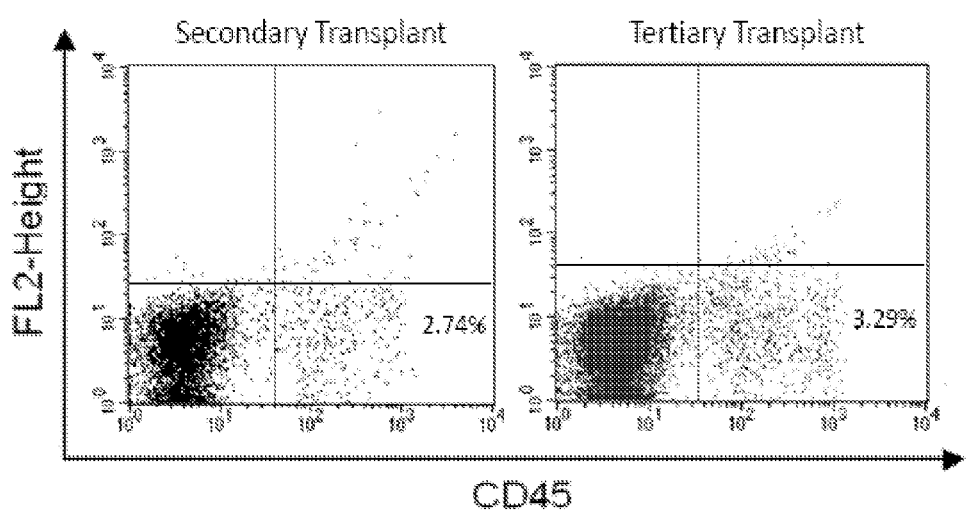
Figure 23:
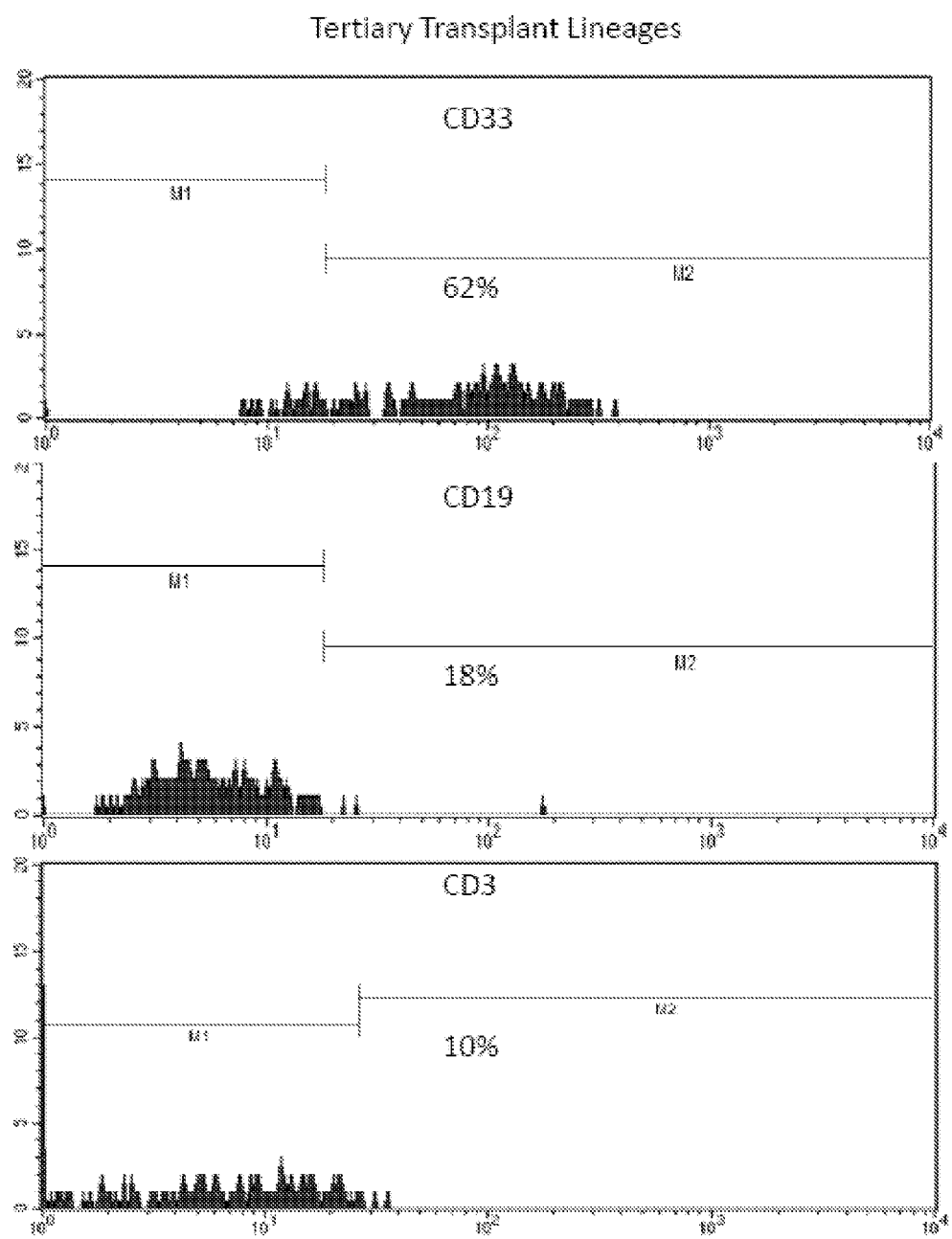
Figure 23:
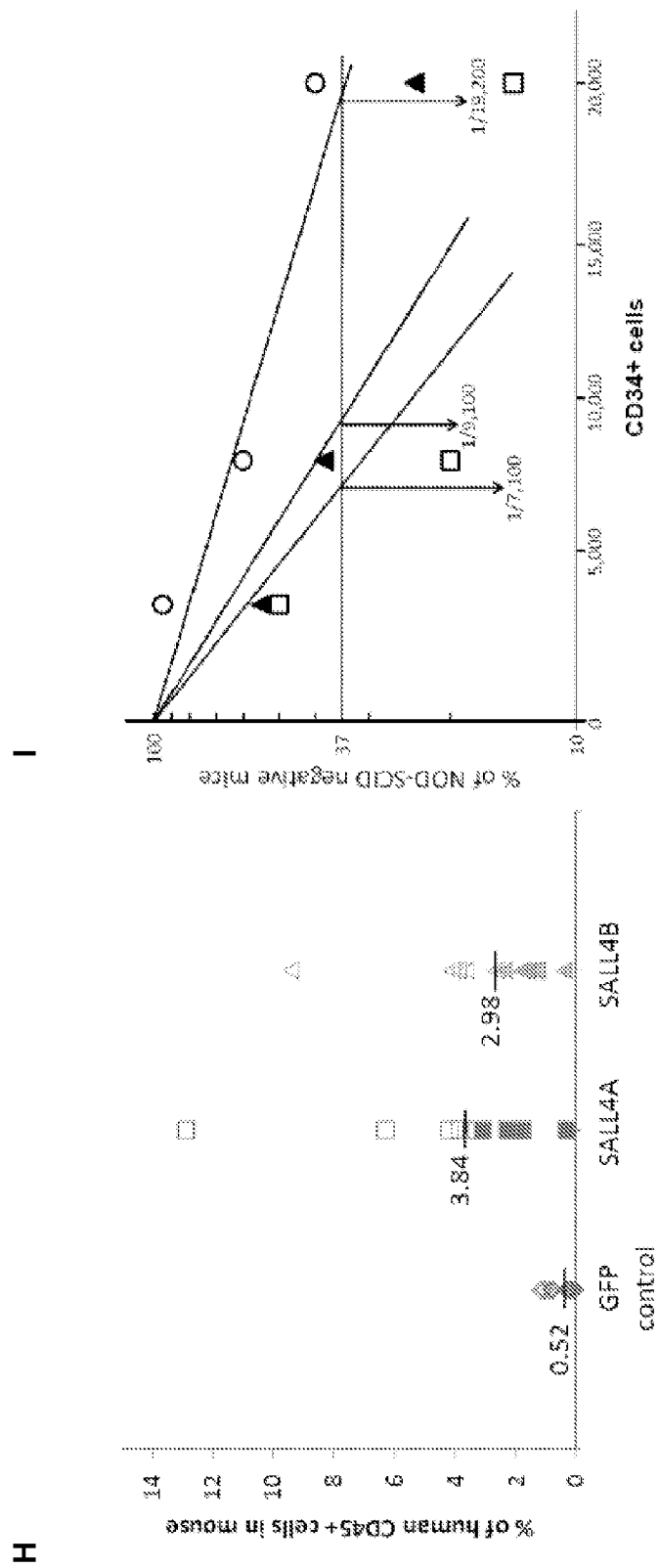

To further test whether the transfer of SALL4 can lead to the long term expansion of human hematopoietic progenitors, SALL4A- and SALL4B-transduced cells were cultured for one month. After 31 days of culture there was a 1780-fold increase for SALL4A and 1463-fold increase for SALL4B in total CD34+ cells numbers compared to controls (FIG. 23A) (control cells ceased to expand after 10 to 12 days). Furthermore, SALL4 transduced cells showed 9.32 fold increases for SALL4A and 8.88 fold increases for SALL4B versus controls for the total number of LTC-ICs after one month (FIG. 23B). Overall, SALL4A transduced cells had a total fold CD34+/CD38− stem cell expansion of 16700 over control while SALL4B transduced cells showed 13300 fold increases although there was not a statistically significant difference between the two SALL4 isoforms (FIG. 23C).

Example 8

Expansion was Associated with Enhanced Stem Cell Repopulation Capacity In vivo

Figure 24:
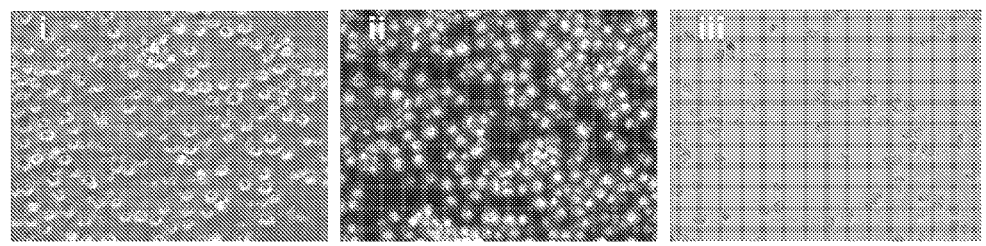
FIG. 24. SALL4-induced expansion of 32D cells proliferate after the removal of IL-3 and addition of G-CSF. Three days after the removal of IL-3 and addition of G-CSF to the growth media of the cells, the SALL4A- and SALL4B-induced cells continue to expand while the GFP induced cells exhibit a decrease in cell number. At 7 days, the SALL4A- (i) and SALL4B-induced (ii) cells continue to proliferate while the control cells (iii) have undergone cell death.

Xenotransplantation assays were transformed to test if SALL4 mediated cells are able to override the regulatory machinery in the marrow-niche to control their differentiation, repopulation capacity, and stem cell output. Phenotypic analysis revealed that both SALL4A- (n=9) and SALL4B-transduced (n=10) cells were capable of positive cell engraftment into NOD/SCID mice (FIG. 23D) 4 weeks post-injection. In addition, experimental animals (n=8) demonstrated myeloid (CD15+) and lymphoid (CD19+) lineages 4 weeks post-injection (FIG. 23E) indicative of a myeloid/lymphoid differentiation process. Bone marrow from animals (n=4) 15 weeks post-injection were analyzed using flow cytometry and still exhibited three lineage differentiation, including CD3+/CD19+ lymphoid, CD15+ myeloid, and Glycophorin-4A+ erythroid lineages (FIG. 24).

To further determine if SALL4-induced cells bear a long-term engraftable property, secondary and tertiary transplantations were conducted with bone marrow harvested from primary animals injected with human CD34+ cells. Flow analysis demonstrated that 8 weeks post-injection, animal marrows still had CD45+ cells (2.74%) but did not attain significant CD34+ cells (<0.24%) showing no leukemic effect.

In addition, the CD45+ population were positive for CD3+ (2.97%)/CD19+ (0.89%) lymphoid, CD15+ (14.1%) myeloid, and Glycophorin-4A+(5.6%) lineages. This showed that successful bone marrow transplantation from one animal to another was possible and that cells could differentiate properly in the bone marrow niche. In addition, tertiary transplantations were conducted with bone marrow harvested from secondary transplant animals. 10 weeks post transplant, the animals still exhibited CD45+ (3.29%) cells within their bone marrow (FIGS. 23F and 23G). Further analysis of the CD45+ population demonstrated the cells were positive for myeloid and lymphoid lineages similar to that of the second transplant (FIGS. 23F and 23G).

After 4 weeks of culture, the ability of SALL4A or SALL4B to increase the repopulating capacity of human cells into NOD/SCID was demonstrated by a strong enhancement in the level of chimerism in mice transplanted with SALL4A or SALL4B-transduced cells. The proportion of CD45+ cells with SALL4A was 3.84% (0.34-12.89%; n=12) and with SALL4B was 2.98% (0.41-9.41%; n=12) compared to 0.52% (0.03-1.18%; n=12) for control cells (FIG. 23H). Furthermore, long-term engraftment with SALL4A- or B-transduced cells was also evident by detecting human CD45+ cells in the mouse peripheral blood at 14 weeks (n=6) or 19 weeks (n=3).

To quantitatively measure the effects of SALL4-transduced CD34+ cells, we conducted limiting-dilution experiments to determine the NOD/SCID mice repopulating cell (SRC) frequency. At 7 weeks after injection, the SRC frequency increased from 1 in 19,200 CD34+ cells (range defined by +/−s.e.: 14,100-25,900) to, respectively, 1 in 7,100 (range defined by +/−s.e.: 5,200-9,800) for SALL4A and 1 in 9,100 (range defined by +/−s.e.: 6,700-12,400) for SALL4B. The total SRC content was expanded by 1080 fold for SALL4A and 844 fold for SALL4B (n=72) compared to uncultured cells by taking into account the increase in the SRC frequencies and total cell numbers (FIG. 23I). Without wishing to be bound by any scientific theory, these results may suggest that overexpression of SALL4 solely in HSCs does not override the regulatory mechanisms involved in the control of stem cell output in vivo.

Example 9

TAT-SALL4B Protein Induced CD34+ Cell Expansion

Figure 25:
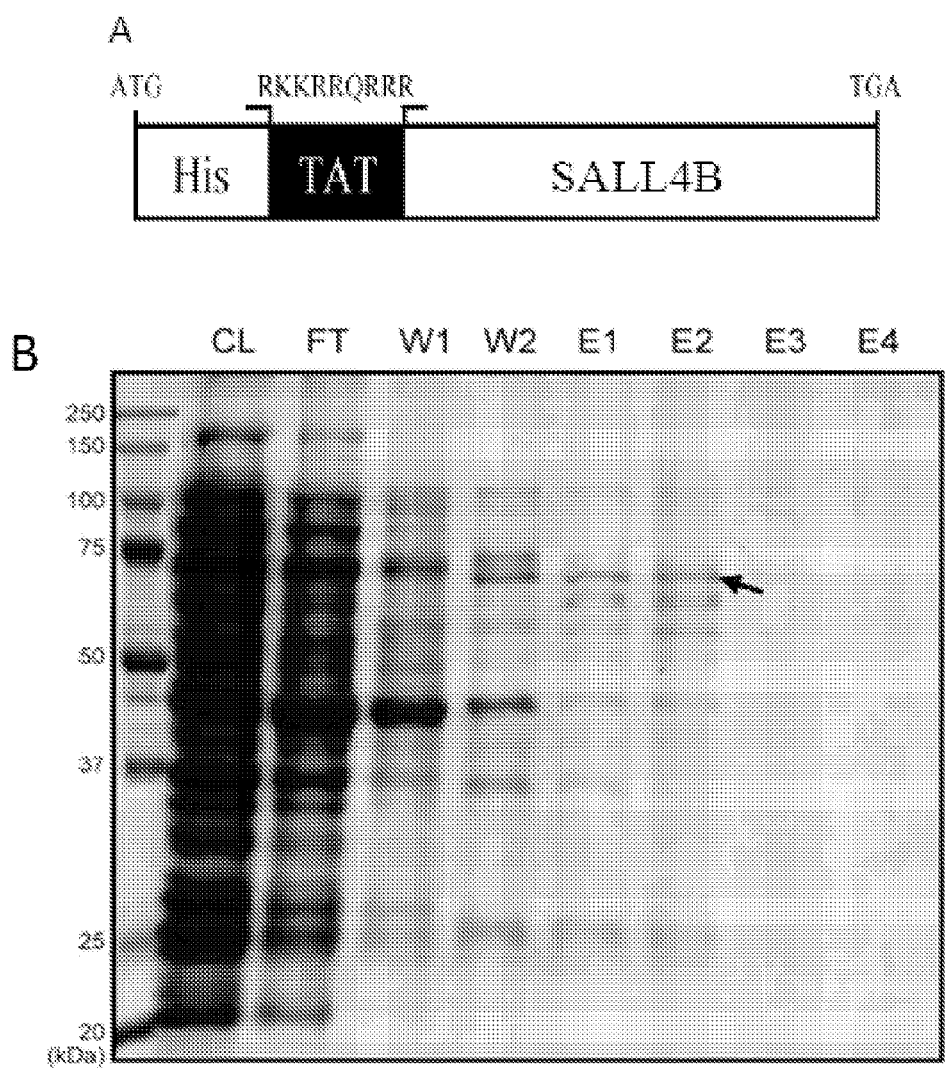
FIG. 25. (A) Schematic representation of human His-TAT-SALL4B construct. This construct was generated by cloning the human SALL4B cDNA into a pTAT-pET28b vector (gift from S. F. Dowdy, University of California, San Diego). (B) Affinity purification of His-TAT-SALL4B as detected by Coomassie blue-stained SDS-PAGE. CL, clear lysates with 0.1 mM IPTG induction for 3 h; FT, flow through; W, wash; E, eluates. The band indicated by the arrow was further identified by LC-MS/MS as shown in part (D). (C) Western blot of purified His-TAT-SALL4B by using anti-6×His tag mouse monoclonal antibodies. W, wash; E, eluates. (D) Identification of purified His-TAT-SALL4B protein by LC-MS/MS. A representation of sequence coverage with purified SALL4B in part (B). The peptides of His-TAT-SALL4B identified by LC-MS/MS are in black color. The percentage of sequence coverage in the specified band was 34% (58 peptides).
Figure 25:
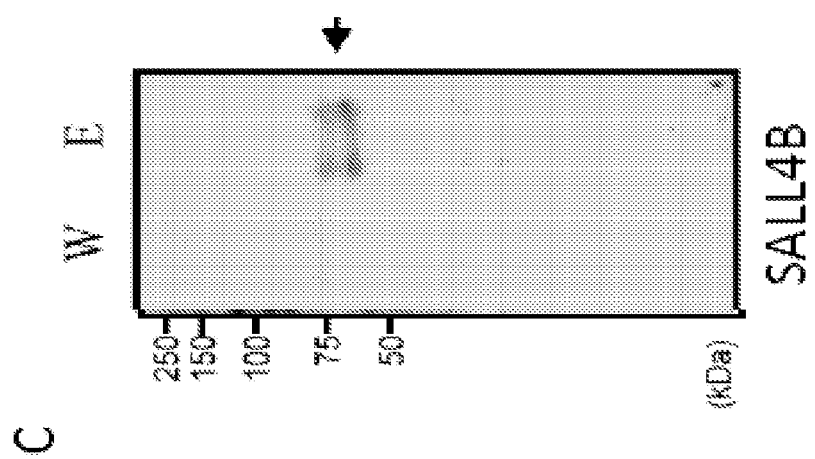
Figure 26:
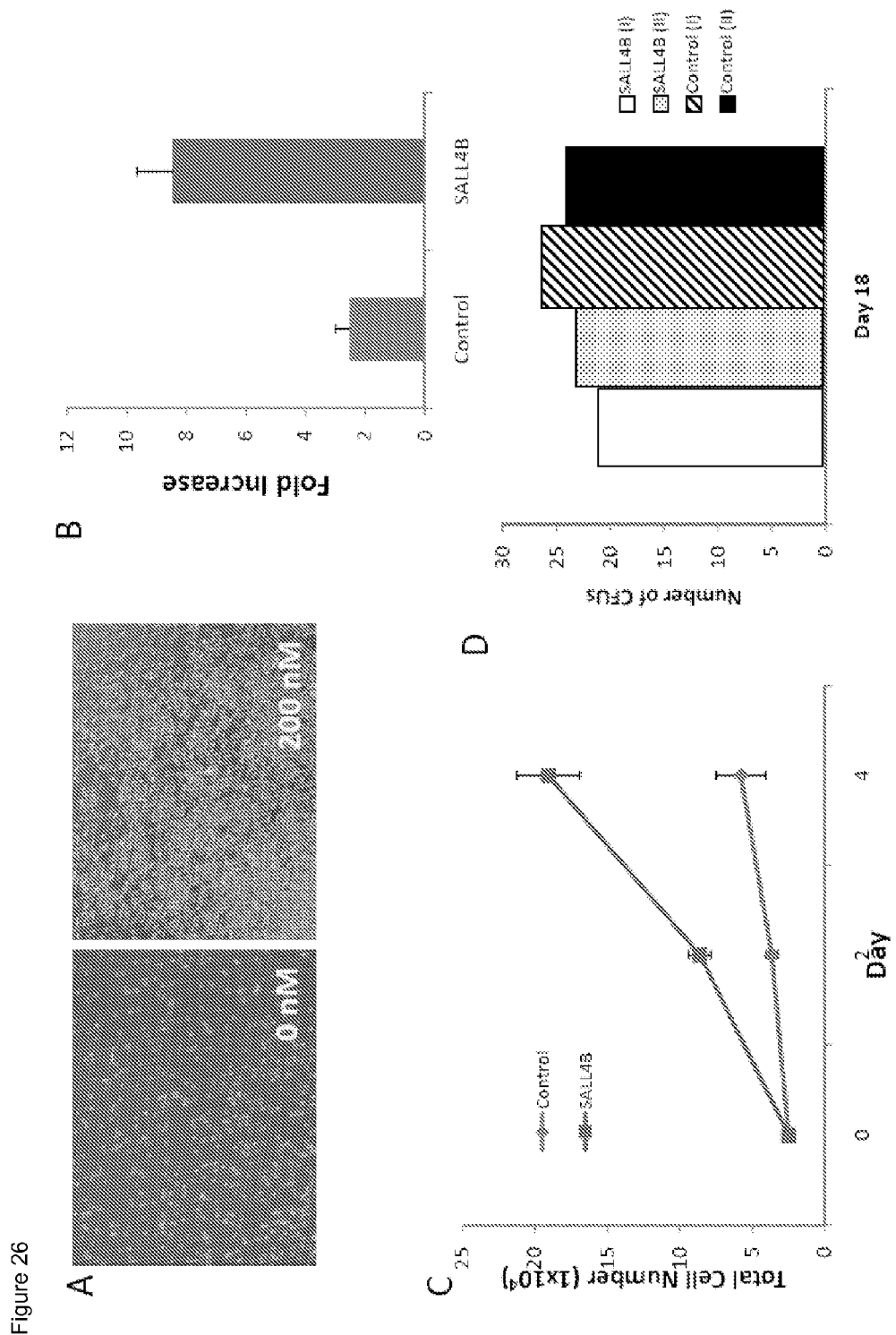
FIG. 26. Human bone marrow CD34+ cells expand at a higher rate when treated with TAT-SALL4B protein. (A) Brightfield images of CD34+ cells after 3 days of protein treatment. (B) Fold increase and total cell number (C) of TAT-SALL4B treated bone marrow cells versus control cells treated solely with BSA. (D) Number of CFU colonies formed from hematopoietic stem cells treated with TAT-SALL4B protein compared to unmanipulated CD34+ cells.
Figure 27:
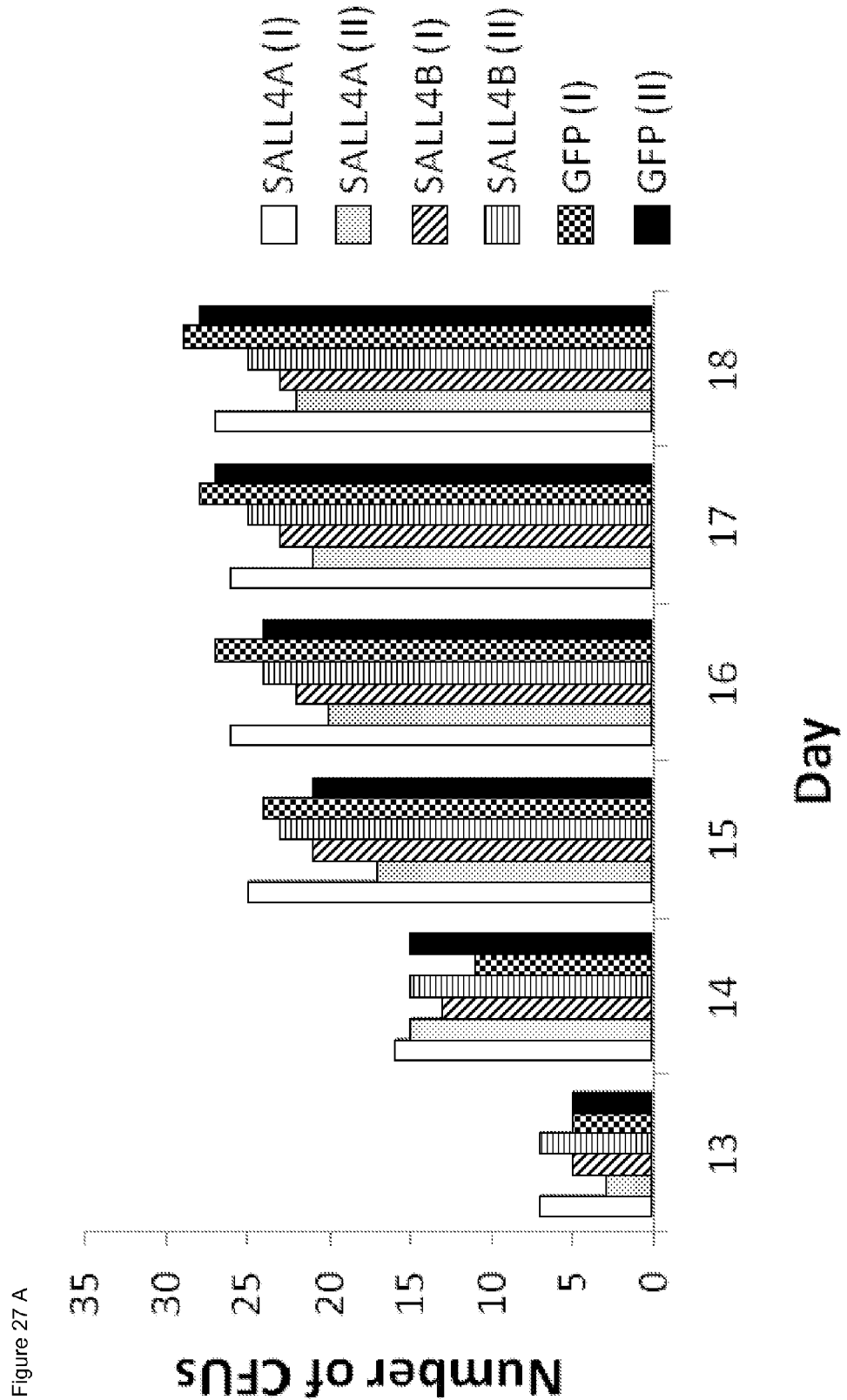
FIG. 27. Number of CFU colonies formed from SALL-4 induced hematopoeitic stem cells. The number and type of CFU colonies were counted 13-18 days after SALL-4 induced or GFP-induced cells were cultured in CFU methocult media.
Figure 27:
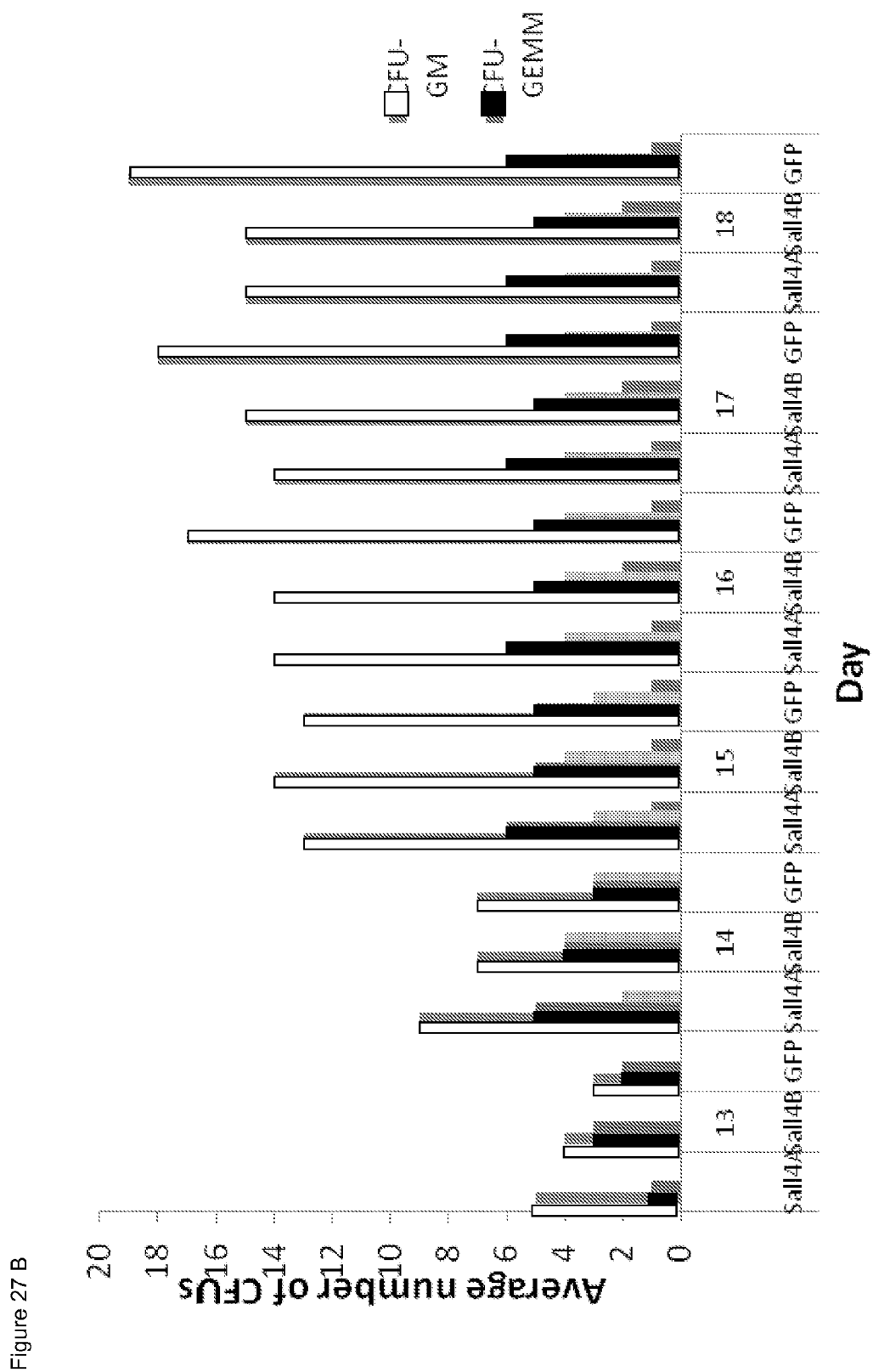
Figure 28:
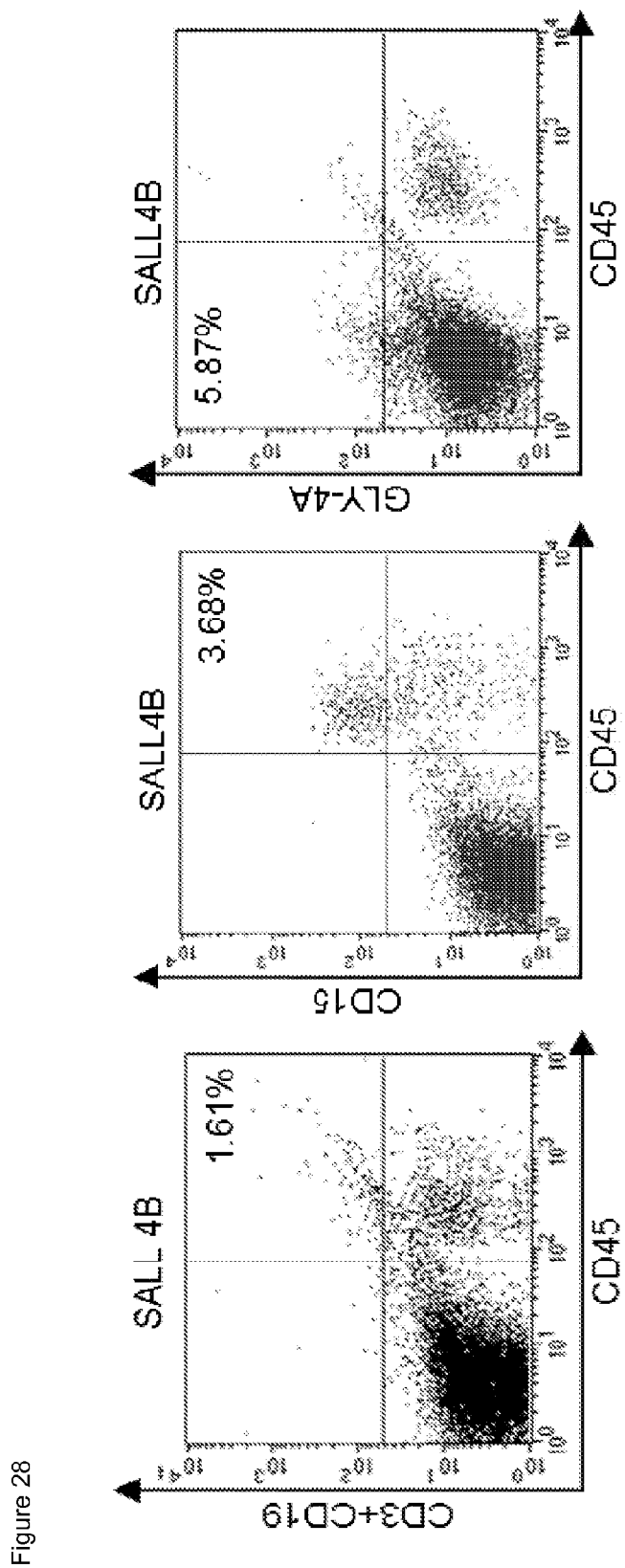
FIG. 28. Multilineage repopulation of engrafted human cells in NOD/SCID mice. Representative flow cytometry profile of mouse bone marrow exhibiting multilineage repopulation of human cells by engrafted cells. The experimental animals showed CD3+/CD19+ lymphoid, CD15+ myeloid, and Glycophorin-4A+ erythroid human cell engraftment 15 weeks post-injection.

Lentiviral expression of SALL4 is very efficient, but its clinical application is not ideal due to difficulties in controlling the level and duration of expression of the transgene in vivo as well as the potential for insertional leukemogenesis. In order to use a different approach to demonstrate the role of SALL4 in HSC expansion, a TAT-6×His-SALL4B protein expressed in $E.$ $coli$, and purified using Ni-NTA agarose (FIGS. 25A and 25B). The recombinant protein of TAT-SALL4B was confirmed by a Western blot with a anti-6×His tag mouse monoclonal antibody and mass spectrometry analysis (FIGS. 25C and 25D). SALL4B was focused on because it is a shorter form and expressed a high level of protein in $E.$ $coli$. After 3 days of TAT-SALL4B treatment, the CD34+ cells expanded rapidly (FIG. 26A). Human CD34+ cells cultured 3 to 4 days with SALL4 fusion protein (200 nM) along with TPO, SCF and Flt-3 ligand showed more than 10 and 8 fold increases of total mononuclear cells and CD34+ cells, respectively (FIGS. 26B and 26C). TAT-SALL4B protein (200 nM) was added twice a day and appeared to be sufficient to expand the cells. In addition, CFU assays demonstrated that these cells could form various colonies including CFU-GM, CFU-GEMM, and BFU-E (FIG. 26D). By taking the fold increase of the TAT-SALL4B treated cells versus control times the CFU numbers, it was noted that the overall CFU number increased by approximately ten fold.

Example 10

Expression and Purification of TAT-SALL4B Fusion Protein in SF9 Insect Cells

Figure 29:
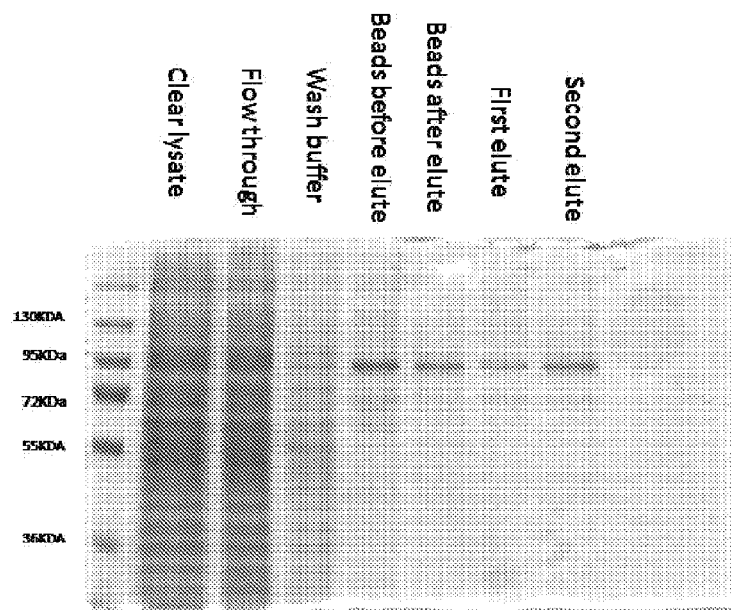
FIG. 29. Western blot of the purification of His-TAT SALL4β isolated from Sf9 cells infected with the baculovirus. Antibodies used were anti-SALL4, (Abnova, Taipei City, Taiwan) 1:2000; and anti-mouse HRP [goat], Abnova, 1:2000.
Figure 30:
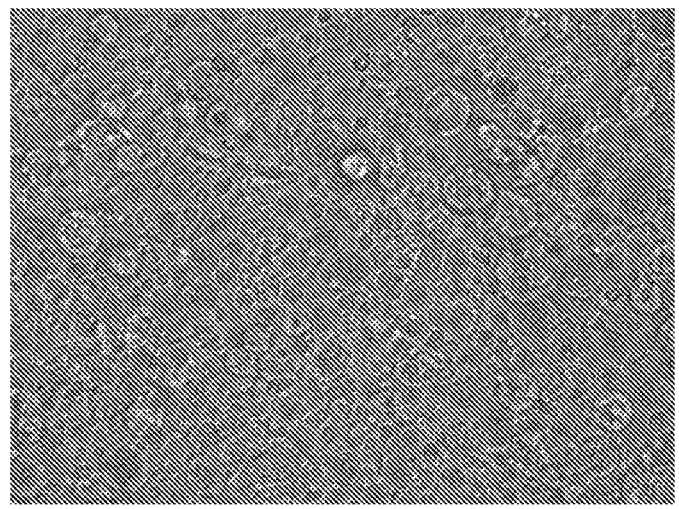
FIG. 30. Sf9 cells infected with baculovirus; 4th day.

Visual inspection of the SF9 cells at 4 days showed the presence of polyhedrins within the cells (FIG. 30), indicating virus production. The expression of hSALL4B protein was confirmed by Western blotting (FIG. 29). The blot also confirmed the presence of His-tagged SALL4B in the first elute and second elute from Ni-NTA beads.

Example 11

In vitro Expansion of Whole Mouse Bone Marrow Cells by TAT-SALL4B Protein

Figure 31:
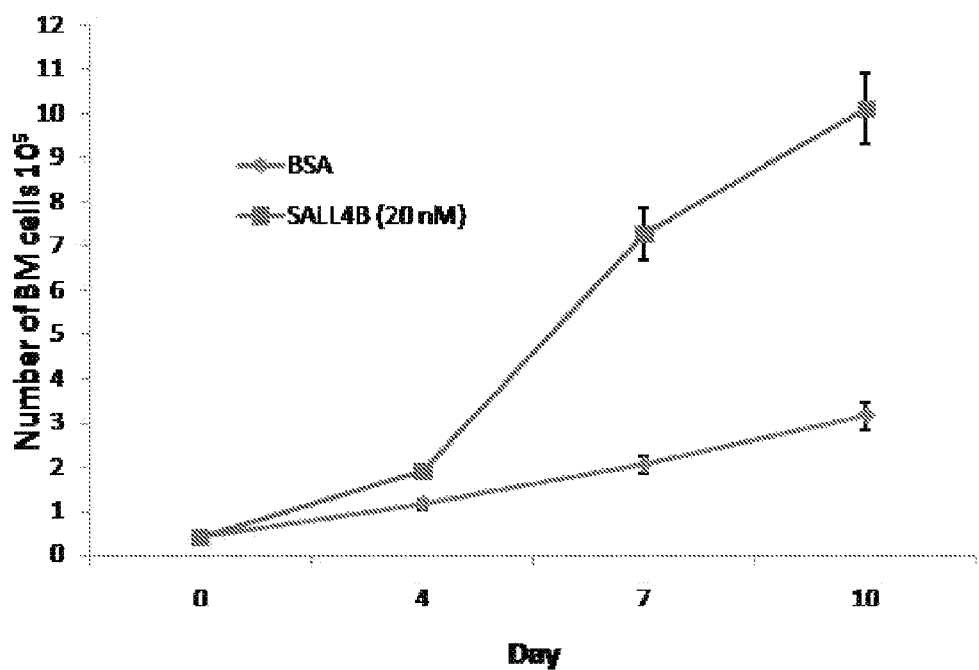
FIG. 31. TAT-SALL4B increase the proliferation of mouse whole bone marrow cells.

Mouse whole bone marrow cells were isolated as previously described. Cells starting at $0.4 \times 10^5$ were cultured in 20 ng/ml TAT-SALL4B protein or 20 ng/ml BSA. The numbers of cells were average at $1.16\times10^5$, $2.04\times10^5$ and $3.16\times10^5$ in BSA group and $1.89\times10^5$, $7.28\times10^5$ and $10.1\times10^5$ in SALL4B group on day 4, 7 and 10 (FIG. 31), showing that TAT-SALL4B can promote the proliferation of whole bone marrow cells in vitro.

Example 12

TAT-SALL4B Protein Promotes Marrow Cell Expansion and the Recovery of Bone Marrow TAT-SALL4B protein, G-CSF or PBS was intraperitoneally injected into mice for 7 consecutive days 24 hours after lethal irradiation. The dose of the lethal irradiation (7Gy, gamma-ray) is able to kill more than 99% of mouse bone marrow cells within one week. An average of $2\times10^7$ whole bone marrow nucleated cells could be obtained from flushing out tibia and femur of both sides in one wide type mouse. In the PBS group, the number of whole bone marrow cells was $1.32\times10^5$ (+/-$0.13\times10^5$; n=6) at day 8 after irradiation. In comparison, G-CSF animals had $4.51\times10^5$ (+/-$0.43\times105$; n=6) cells and the SALL4B treated group had $7.91\times10^5$ (+/-$0.75\times105$; n=7) cells. As consistent with previous reports, G-CSF could increase the number of the cells by 3.42 fold. The fold increases were 6.00 and 1.75 in SALL4B group as compared to PBS control and G-CSF group, respectively, suggesting SALL4B is even better than G-CSF regarding to boosting the proliferation of bone marrow cells after irradiation.

Figure 32:
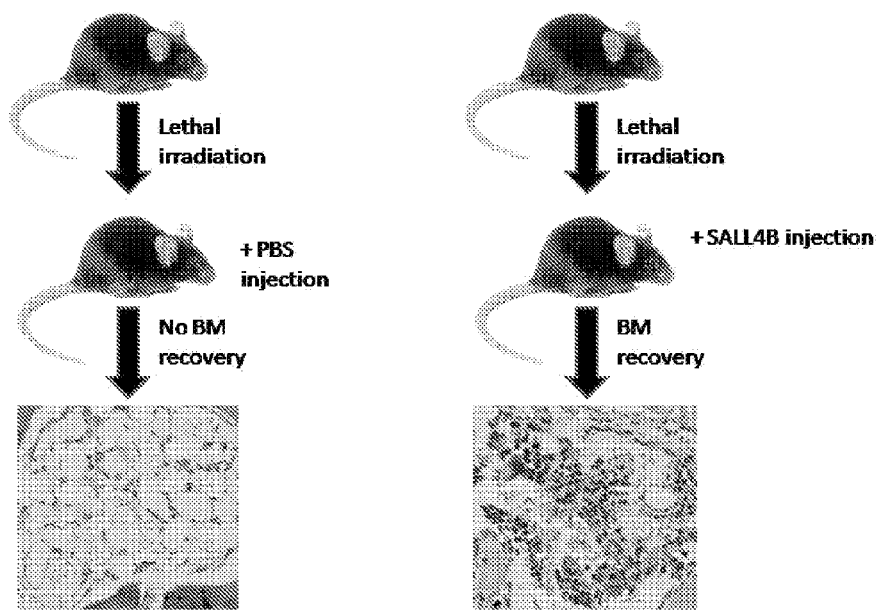
FIG. 32. Bone marrow recovery in SALL4 treated animals with expansion of marrow cells (experimental design).
Figure 33:
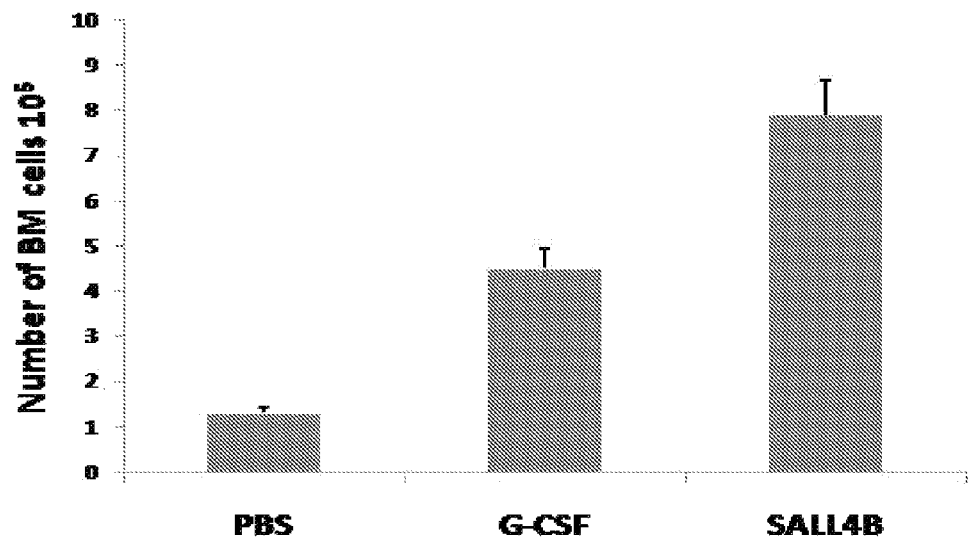
FIG. 33. Expansion of bone marrow cells after injection of TAT-SALL4B
Figure 34:
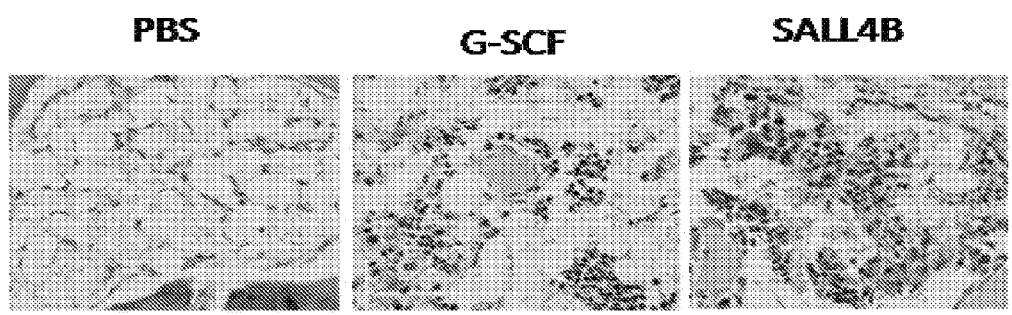
FIG. 34. Comparisons of bone marrow cell expansion after peritoneal injections of PBS, G-SCF and SALL4B in mice. Histological sections of bone marrow cavity showing expansion of marrow cells.

The histological sections from different group at day 8 after irradiation were analyzed. In contrast to PBS group in which only very few cells, mainly marrow stromal cells, left in mouse bone marrow cavity, the cellularization of the bone marrow was dramatically enhanced by G-CSF or SALL4B treatment (FIGS. 32-34). In addition, the majority of cells are identified as of hematopoietic cells. These data demonstrate that SALL4B is efficient in promoting the recovery of bone marrow by increasing the proliferation of bone marrow cells.

Example 13

Figure 35:
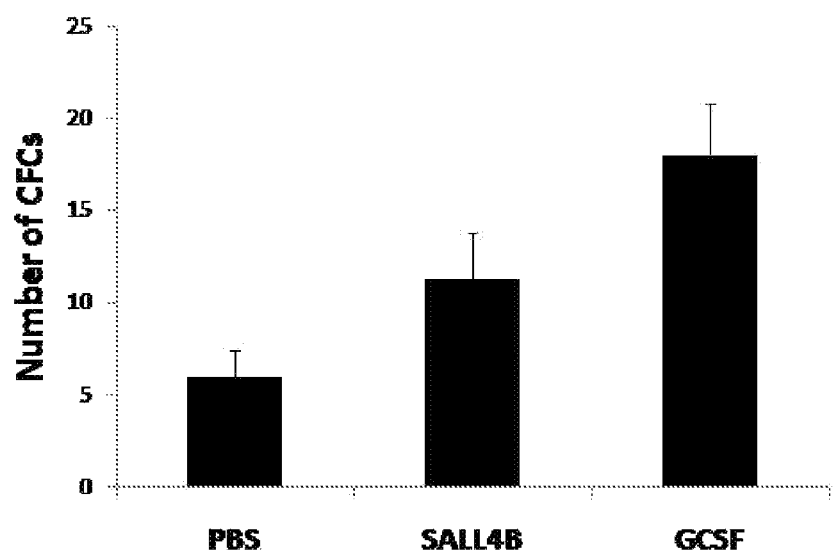
FIG. 35. CFC numbers of bone marrow cells from PBS, SALL4B or G-CSF treated mice. C57B/6 mice were lethally irradiated (7Gy) and received treatment from 24 hours after irradiation for 7 days. At day 8, mice bone marrow cells were isolated and cultured in MethoCult for CFC assays. Per 20,000 whole bone marrow cells, the day 7 CFCs of PBS, SALL4B and G-CSF group were 6±1.41, 11.3±2.51 and 18±2.82 respectively (P values of PBS vs SALL4B, PBS vs G-CSF, SALL4B vs G-CSF are <0.05).

SALL4B Increases Expansion of Hematopoietic Stem and Progenitor Cells in Mouse Bone Marrow With flow cytometry, the hematopoietic stem and progenitor cell content with a combination of Lin, c-Kit and Scal-1 staining for the whole bone marrow cells was detected. The percentage of HPCs (Lin-/c-Kit+Scal-) was increased to 14.7% in G-CSF group and 9.82% in SALL4B group as compared to 5.1% control. These results were correlated well with CFC (colony forming cell) assays (FIG. 35). CFC assays are well characterized assays that can detect an increase or decrease in the frequency of hematopoietic progenitor proliferation in response to stimulatory or inhibitory agents.

Figure 36:
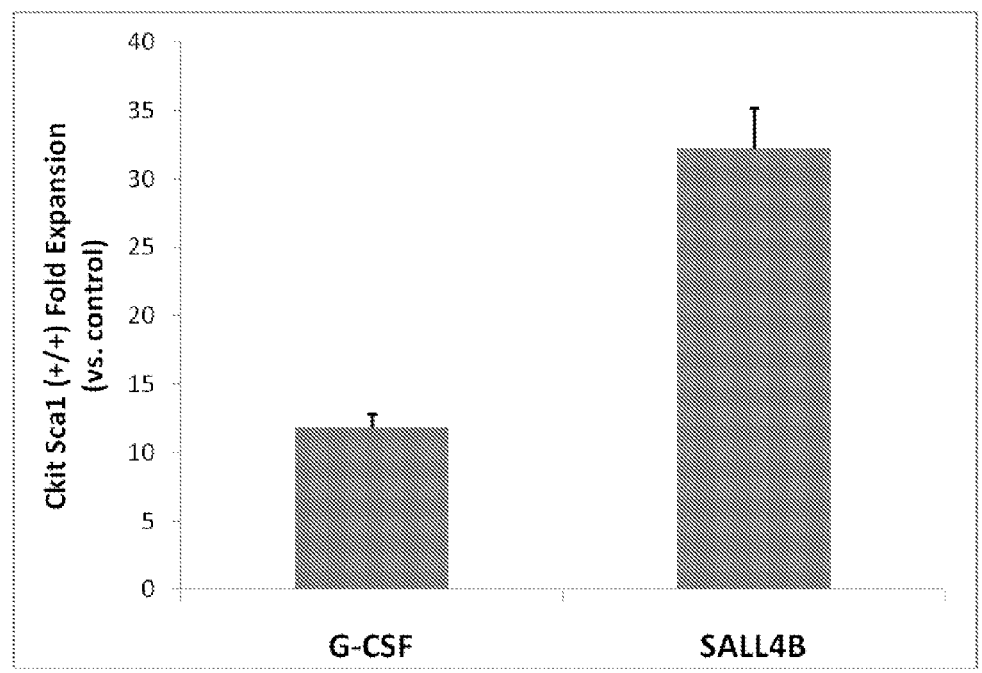
FIG. 36. Fold increase of HSCs (Sca1+/c-kit+) vs control (PBS) from animals treated with SALL4B, G-CSF, or PBS.

In addition, compared to control (1.24%), hematopoietic stem cells (HSCs) (Lin-/c-Kit+/Scal-1+) percentage were also significantly higher in GCSF group (FIG. 36). Importantly, the HSC percentage in SALL4B group was even higher than that in G-CSF group (approximately 2.7 fold increase). The total fold increases (vs. control) of HSCs number in mouse bone marrow were 11.8 (n=6) fold and 32.2 (n=7) fold in G-CSF and SALL4B, respectively.

Example 14

Figure 37:
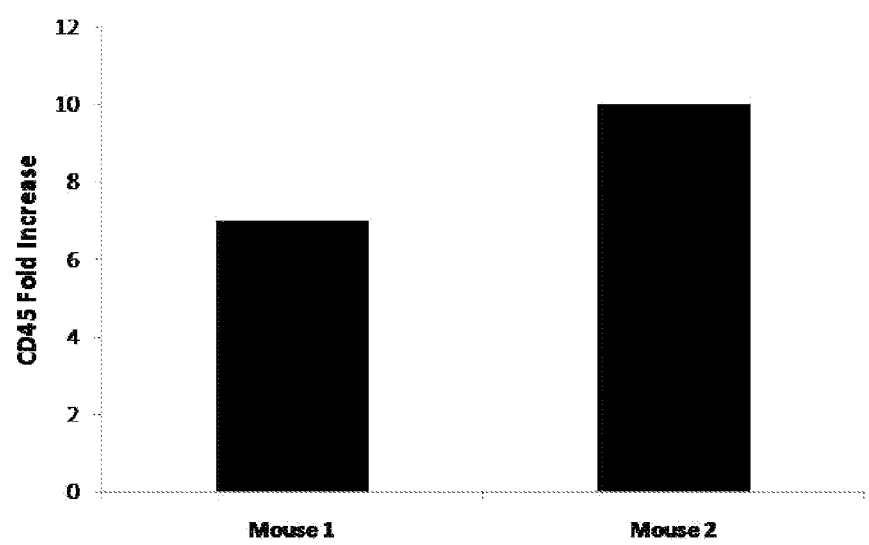
FIG. 37. Fold increase of long-term engraftment of human UCB in the peripheral blood of NOD-SCID mice. Approximately 20,000 cord blood derived-CD34+ cells were transplanted into sub-lethally irradiated NOD/SCID mice and treated with 2 μg/day SALL4B protein for 7 days and then 2 μg/day every other day for an additional week. CD45 cells (UCB cells) 16 weeks post-transplant compared to PBS treated controls will be measured by flow cytometry.
Figure 38:
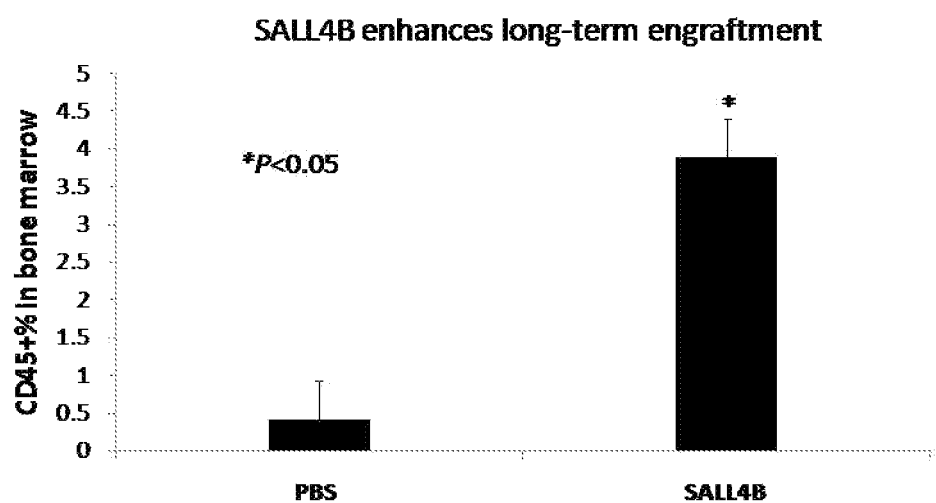
FIG. 38. SALL4B enhances long-term engraftment of human cord blood cells in NOD/SCID mouse. 20,000 human cord blood CD34+ cells were transplanted into NOD/SCID mice 24 hours after sub-lethal irradiation (2.5Gy). Mice were treated with 2 μg TAT-SALL4B protein or PBS for 2 weeks (once a day for the first week and once every other day for the second week). Mice bone marrow cells were collected 4 months post transplantation and analyzed by flow cytometry for CD45 positive cells (engrafted core blood cells).

Enhanced Long-Term Engraftment of Cord Blood Stem Cells and Progenitor Cells by TAT-SALL4B Protein The ability of TAT-SALL4B to increase the efficiency of bone marrow transplantation was tested using Umbilical Cord Blood (UCB) cells. 20,000 CD34+ UCB cells were transplanted into sub-lethally irradiated NOD/SCID mice and treated with 2 ug/day SALL4B protein for 7 days and then 2 ug/day every other day for an additional week (FIG. 37). Animals treated with TAT-SALL4B protein isolated from SF9 cells showed an 8.5 fold increase in the long-term engraftment of CD45+ cells (UCB cells) in the peripheral blood 16 weeks post-transplant compared to PBS treated controls. CD45 cells (UCB cells) 16 weeks post-transplant compared to PBS treated controls. The transplanted UCB cells in the marrow was further examined. As shown in FIG. 38, the level of donor cells, UCB in mice administrated with TAT-SALL4B, was increased by 10 fold compared with that of control mice injected with PBS and was measured four months post-transplant, demonstrating an achievement of long-term engraftment. These studies indicate that TAT-SALL4 protein is a robust factor in the promotion of stem cell engraftment.

Example 15

TAT-SALL4 Increases Yield of Stem and Progenitor Cells

Figure 39:
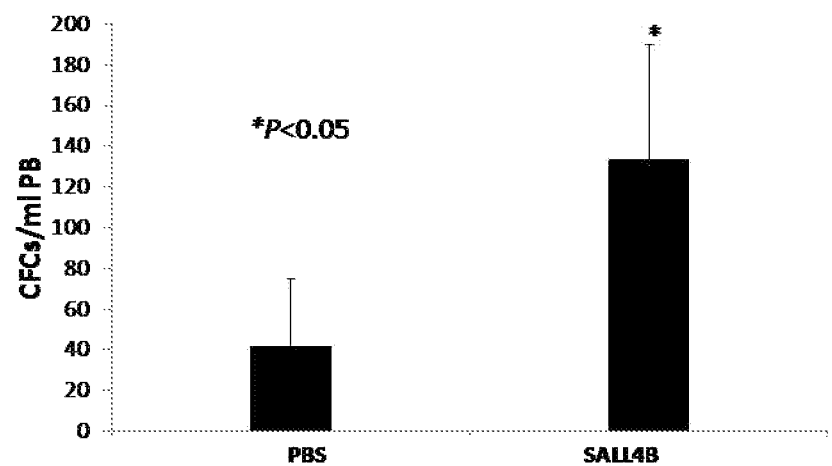
FIG. 39. SALL4B increases CFC numbers of peripheral blood (PB). Wild type C57B/6 mice received PBS or 6 μg TAT-SALL4B protein injection (intraperitoneal injection) for 5 days and PB were collected 2 hours after last injection. The nucleated cells from peripheral blood of injected mice were used for CFC (colony forming progenitor cell) assays. CFC numbers on Day 7 were counted under microscope.

Enumeration of hematopoietic colony-forming progenitor cells (CFC) is used to evaluate peripheral blood progenitor cell collections. CFC association with the day of neutrophils recovery, measured as the coefficient of correlation, is stronger than that of the total nuclear cells. SALL4B protein was intraperitoneally injected to wild type mice and then the peripheral blood was collected from injected mice to evaluate the number of CFC. As shown in FIG. 39, the CFC numbers in the peripheral blood from mice injected with SALL4B protein were increased by threefold compared to that of mice injected with PBS. This study indicated that TAT-SALL4 is able to increase the peripheral blood yield of stem and progenitor cells when TAT-SALL4 is administrated.

Discussion

As demonstrated herein, SALL4A and SALL4B are strong positive regulators of hematopoetic stem cell expansion. While previous attempts to expand HSCs using hematopoietic growth factors such as fetal liver tyrosine kinase (Flt3) ligand, stem cell factor, interleukins 6 and 11, HOXB4, OCT4 and Nanog show only a limited expansion of HSCs, HSCs receiving expression of SALL4A or SALL4B are able to achieve a high-level of ex vivo expansion. Cultures of SALL4-transduced cells results in extensive HSC expansion with over 1000-fold higher levels than controls within 2 to 3 weeks and expanded HSCs show no or very little maturation. Moreover, the expansion occurs quite rapidly with significant HSC growth in just a few days. In addition, SALL4-induced HSC expansion exhibits no impairment of hematopoietic cell differentiation. SALL4 appears to function in the maintenance of an undifferentiated proliferation state and block cell differentiation for HSCs.

A new therapeutic strategy is described herein, which in some embodiments uses cytokine-dependent SALL4 technology for the dramatic 10,000 to 15,000-fold ex vivo expansion of human HSCs without significant differentiation over 4 weeks. In some experiments, even after 8 weeks of cell culture, 37% of the CD34+ cells were still CD34+/CD38− (data not shown). In xenotransplantation models, the stem cell frequency of cells that had been induced by SALL4 for 4 weeks ex vivo was only 2-2.5-fold higher than fresh CD34+ cells (FIG. 26H). Without wishing to be bound by any scientific theory, the in vivo growth of SALL4-induced HSCs might be dissimilar to those in cell culture conditions (ex vivo) where an excess of special cytokines is present.

In some embodiments described herein the magnitude of HSC expansion is unprecedentedly high with 10,000 fold for CD34+/CD38− and CD34+/CD38+ populations. In addition, the expansion of engraftable long-term HSCs by the SALL4 approach described herein is achievable in embodiments of the invention and is supported by evidence of the secondary and tertiary transplantation studies described herein.

Massive ex vivo expansion of CD34+ cells can be achieved without differentiation using materials and methods described herein. These expanded cells retain long-term engraftment properties similar to those of un-manipulated cells in vivo. In experimental examples described herein, the SALL4-expanded cells sustained a long-term engraftment demonstrated by serial xenotransplant models and repopulation assays. Most critically, after transplantation they do not override the niche-induced regulatory controls, allowing these expanded stem cells to avoid leukemic formation. No evidence of leukemia was evident in transplanted mice in either serially xenotransplanted animals or by more than 10 months post-transplantation (data not shown). In addition, no leukemic formation was exhibited for 12 months post syngeneic transplantation when either SALL4A or B was expressed and introduced into mouse stem/progenitor hematopoietic cells (n=6).

REFERENCES

1. Ueda et al., Expansion of human NOD/SCID-repopulating cells by stem cell factor, Flk2/Flt3 ligand, thrombopoietin, IL-6, and soluble IL-6 receptor, J Clin Invest. (2000) 105 (7):1013-21.
2. Yonemura et al., In Vitro Expansion of Hematopoietic Progenitors and Maintenance of Stem Cells: Comparison Between FLT3/FLK-2 Ligand and KIT Ligand, Blood (1997) 89:1915-1921.
3. Peters et al., Ex vivo expansion of murine marrow cells with interleukin-3 (IL-3), IL-6, IL-11, and stem cell factor leads to impaired engraftment in irradiated hosts. Blood (1996) 87(1):30-7.
4. Antonchuk et al., HOXB4-induced expansion of adult hematopoietic stem cells ex vivo, Cell. 2002 109(1):39-45.
5. Elling U, Klasen C, Eisenberger T, Anlag K, Treier M (2006) Murine inner cell mass-derived lineages depend on Sall4 function. Proc Natl Acad Sci USA 103(44): 16319-24.
6. Hart A H, Hartley L, Ibrahim M, Robb L (2004) Identification, cloning and expression analysis of the pluripotency promoting Nanog genes in mouse and human. Dev Dyn 230(1): 187-98.
7. Zhang J, Tam W L, Tong G Q, Wu Q, Chan H Y, et al. (2006) Sall4 modulates embryonic stem cell pluripotency and early embryonic development by the transcriptional regulation of Pou5f1. Nat Cell Biol 8(10): 1114-23.
8. Li S S, Liu Y H, Tseng C N, Chung T L, Lee T Y, et al. (2006) Characterization and gene expression profiling of five new human embryonic stem cell lines derived in Taiwan. Stem Cells Dev 15(4): 532-55.
9. Wang J, Rao S, Chu J, Shen X, Levasseur D N, et al. (2006) A protein interaction network for pluripotency of embryonic stem cells. Nature 444(7117): 364-8.
10. Wu Q, Chen X, Zhang J, Loh Y H, Low T Y, et al. (2006) Sall4 interacts with Nanog and co-occupies Nanog genomic sites in embryonic stem cells. J Biol Chem 281 (34): 24090-4.
11. Zhou Q, Chipperfield H, Melton D A, Wong W H (2007) A gene regulatory network in mouse embryonic stem cells. Proc Natl Acad Sci USA 104(42): 16438-43.
12. Chen X, Vega V B, Ng H H (2008) Transcriptional regulatory networks in embryonic stem cells. Cold Spring Harb Symp Quant Biol 73: 203-9.
13. Lim C Y, Tam W L, Zhang J, Ang H S, Jia H, et al. (2008) Sall4 regulates distinct transcription circuitries in different blastocyst-derived stem cell lineages. Cell Stem Cell 3(5): 543-54.
14. Yang J, Chai L, Fowles T C, Alipio Z, Xu D, et al. (2008) Genome-wide analysis reveals Sall4 to be a major regulator of pluripotency in murine-embryonic stem cells. Proc Natl Acad Sci USA 105(50): 19756-61.
15. Futaki et al., Arginine-rich peptides and their internalization mechanisms Biochem Soc Trans, 2007 4:784-7.
16. Cronican et al., Potent Delivery of Functional Proteins into Mammalian Cells in Vitro and in Vivo Using a Supercharged Protein, ACS Chem Biol. 2010 Jun. 21. [Epub ahead of print]
17. Sieburg et al., The haematopoietic stem cell compartment consists of a limited number of discrete stem cell subsets. Blood, 2006 107:2311-6.
18. Schroeder T, Haematopoietic Stem Cell Heterogeneity: Subtypes, Not Unpredictable Behavior. Stem Cell, 2010.
19. Dykstra et al., Long-Term Propagation of Distinct Hematopoietic Differentiation Programs In Vivo. Cell Stem Cell 2007 1(2):218-229.

---

What is claimed is:

1. A method for expanding a hematopoietic stem cell population, the method comprising providing to the stem cell population a Sal-like 4 (SALL4) polypeptide attached to a transport moiety capable of crossing a cell membrane, in an amount effective to expand the stem cell population.

2. The method of claim 1, wherein the hematopoietic stem cell is an adult hematopoietic stem cell.

3. The method of claim 1, wherein the hematopoietic stem cell is in or derived from umbilical cord blood, peripheral blood, bone marrow, or spleen.

4. The method of claim 1, wherein the hematopoietic stem cell is a human stem cell.

5. The method of claim 1, wherein the transport moiety is a HIV-1transactivator of transcription (TAT) peptide, a Chariot protein, an arginine-rich peptide, an Antennapedia-derived penetratin peptide, a herpes simplex virus type 1 VP22 protein, or a +36 GFP.

6. The method of claim 1, wherein the SALL4 polypeptide comprises amino acids in the sequence set forth as SEQ ID No: 11 or 12.

7. The method of claim 1, wherein the stem cell population is expanded 10-fold, 20-fold, 50-fold, 100-fold, or 1000-fold.

8. A method for expanding a hematopoietic stem cell population ex vivo, the method comprising providing to the ex vivo stem cell population Sal-like 4 (SALL4) polypeptide in an amount effective to expand the stem cell population.

9. The method of claim 8, wherein the cell population is cultured in media comprising 50 ng/ml FMS-like tyrosine kinase-3 (FLT-3), 50 ng/ml Thrombopoietin (TPO), and/or 50 ng/ml Stem cell factor (SCF) or in media comprising 25 ng/ml FMS-like tyrosine kinase-3 (FLT-3), 25 ng/ml Thrombopoietin (TPO), and/or 25 ng/ml Stem cell factor (SCF).

10. The method of claim 8, wherein the SALL4 polypeptide is encoded by a nucleotide sequence comprising the sequence set forth as SEQ ID No: 5 or 6.

11. The method of claim 8, wherein a stem cell in the population is transduced with a viral vector comprising nucleotides encoding the SALL4 polypeptide, thereby providing the SALL4 polypeptide to the stem cell population.

12. The method of claim 11, wherein expression of said SALL4 polypeptide is under the control of an inducible promoter.

13. The method of claim 8, wherein the hematopoietic stem cell population is an adult hematopoietic stem cell population.

14. The method of claim 8, wherein the hematopoietic stem cell population is in or derived from umbilical cord blood, peripheral blood, bone marrow, or spleen.

15. A method for treatment of a disorder in a subject requiring a hematopoietic stem cell or an expanded hematopoietic stem cell, the method comprising:
   a) obtaining a hematopoietic stem cell population,
   b) providing to the stem cell population a composition comprising a Sal-like 4 (SALL4) polypeptide in an effective amount for the expansion of the stem cell population, and
   c) transplanting the expanded stem cell population to the subject in an amount effective for the treatment of said disorder.

* * * * *